United States Patent
Mori et al.

(10) Patent No.: US 10,709,898 B2
(45) Date of Patent: Jul. 14, 2020

(54) LIGHT IRRADIATING DEVICE AND PHOTOTHERAPY MACHINE

(71) Applicant: SHARP KABUSHIKI KAISHA, Sakai, Osaka (JP)

(72) Inventors: Jun Mori, Sakai (JP); Hiroya Sato, Sakai (JP); Masatsugu Masuda, Sakai (JP); Katsuji Iguchi, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 84 days.

(21) Appl. No.: 16/065,038

(22) PCT Filed: Sep. 29, 2016

(86) PCT No.: PCT/JP2016/078862
§ 371 (c)(1),
(2) Date: Jun. 21, 2018

(87) PCT Pub. No.: WO2017/110194
PCT Pub. Date: Jun. 29, 2017

(65) Prior Publication Data
US 2019/0009102 A1    Jan. 10, 2019

(30) Foreign Application Priority Data

Dec. 24, 2015  (JP) .................................. 2015-252576
Feb. 9, 2016    (JP) .................................. 2016-023093

(51) Int. Cl.
*H01L 33/50*    (2010.01)
*H01L 25/075*   (2006.01)
*A61N 5/06*     (2006.01)

(52) U.S. Cl.
CPC .......... *A61N 5/0616* (2013.01); *A61N 5/062* (2013.01); *A61N 2005/0643* (2013.01);
(Continued)

(58) Field of Classification Search
CPC ....... H01L 33/50; H01L 25/00; H01L 25/075; H01L 25/0753; H01L 25/50;
(Continued)

(56) References Cited

U.S. PATENT DOCUMENTS

2007/0129613 A1  6/2007  Rochester et al.
2013/0178919 A1  7/2013  McNeill
(Continued)

FOREIGN PATENT DOCUMENTS

JP   H09-038221 A   2/1997
JP   H11-192315 A   7/1999
(Continued)

OTHER PUBLICATIONS

Toshiyuki Ozawa et al. "A New Treatment for MRSA Infection that Does Not Cause Resistant Bacteria" https://www.osaka-cu.ac.jp/ja/news/2014/files/setumei_140819.pdf.

*Primary Examiner* — Jon Eric C Morales
(74) *Attorney, Agent, or Firm* — ScienBiziP, P.C.

(57) ABSTRACT

Light irradiation that is suitable for treatment for a relatively small diseased part and is performed almost uniformly and efficiently for the entirety of an affected part even when the affected part is not flat is realized. Light output from a plurality of LED chips includes first wavelength region light whose light-emission intensity peak is in a wavelength range of 380 nm or more and 430 nm or less and second wavelength region light whose light-emission intensity peak is in a wavelength range of more than 430 nm and 635 nm or less, and a group of LED light sources has uniform in-plane intensity of light irradiation.

15 Claims, 34 Drawing Sheets

(52) U.S. Cl.
CPC ............... *A61N 2005/0652* (2013.01); *A61N 2005/0663* (2013.01); *A61N 2005/0666* (2013.01)

(58) Field of Classification Search
CPC ......... H01L 2924/3025; H01L 2924/00; H01L 2224/48091; H01L 2924/00014; F21K 99/00; F21K 9/60; F21V 29/00; F21V 29/74; A01G 7/045; Y02P 60/149; F21Y 2115/10

See application file for complete search history.

(56) References Cited

U.S. PATENT DOCUMENTS

| | | | |
|---|---|---|---|
| 2014/0340890 A1* | 11/2014 | Hata | ............... A01G 7/045 362/231 |
| 2014/0350454 A1 | 11/2014 | Klem | |

FOREIGN PATENT DOCUMENTS

| | | |
|---|---|---|
| JP | 2007-518467 A | 7/2007 |
| JP | 2010-284399 A | 12/2010 |
| JP | 2013-532503 A | 8/2013 |
| JP | 2015-500717 A | 1/2015 |
| JP | 2015-24060 A | 2/2015 |
| JP | 2015-115241 A | 6/2015 |
| WO | 2015/190335 A1 | 12/2015 |

* cited by examiner

| FIGURE NUMBER | WAVELENGTH OF EXCITATION LED (nm) | LIGHT-EMISSION PEAK WAVELENGTH (nm) | FULL WIDTH AT HALF MAXIMUM (nm) |
|---|---|---|---|
| 4 | 405 | 495.5 | 31 |
| 5 | 405 | 515 | 20 |
| 6 | 405 | 530 | 65 |
| 7 | 405 | 520 | 80 |
| 8 | 405 | 540 | 50 |
| 9 | 405 | 545 | 65 |
| 10 | 405 | 555 | 115 |
| 11 | 405 | 595 | 85 |
| 12 | 405 | 620 | 85 |
| 13 | 405 | 630 | 90 |
| 14 | 405 | 650 | 95 |
| 15 | 405 | 660 | 100 |
| 16 | 450 | 540 | 100 |
| 17 | 450 | 540 | 110 |
| 18 | 450 | 630 | 10 |

LIGHT IRRADIATING DEVICE AND PHOTOTHERAPY MACHINE

TECHNICAL FIELD

The present invention relates to a light irradiating device and a phototherapy machine.

BACKGROUND ART

Photo Dynamic Therapy (PDT) is a method of treatment in which active oxygen or the like is generated by a chemical reaction that arises when a photosensitive substance with an affinity for an abnormal cell or a tumor is irradiated with light of a specific wavelength and the abnormal cell or the tumor is necrotized by a bactericidal activity of the active oxygen. Much attention has been recently drawn from a viewpoint of QOL (Quality Of Life) because a normal cell is not damaged.

Meanwhile, laser is mainly used as a light source used for the PDT. A reason therefor is, for example, that the laser is monochromatic light and is able to effectively excite a photosensitive substance having a narrow absorption band, that the laser has high light intensity density, and that the laser is able to generate pulse light. However, laser light is normally spot light, has a narrow radiation coverage, and hence is not suitable for treatment of skin disease or the like.

In recent years, a group of Professor Daisuke Tsuruta, Instructor Toshiyuki Ozawa, et al. of Osaka City University Graduate School of Medicine has presented the first success in the world in treatment of a Methicillin-resistant *Staphylococcus aureus* (MRSA) infected skin ulcer by conducting systemic administration of 5-aminolevulinic acid (ALA) that is natural amino acid and the PDT using LED light with a wavelength of 410 nm (refer to NPL 1). The ALA is a precursor of a porphyrin-based compound in a heme biosynthetic pathway, and does not provide photosensitizing properties by itself. When a given amount of hemes is produced, physiologically, biosynthesis of the ALA is inhibited by a negative feedback mechanism. However, when exogenous ALA is excessively administered, the negative feedback mechanism is invalid, ferrochelatase that is a rate limiting enzyme in heme biosynthesis is depleted, and a large amount of biologically-inherent porphyrin-based compounds, particularly, protoporphyrin IX (PpIX) is accumulated in a cell. In the PDT using the ALA, the PpIX is used as a photosensitizing substance. Such a method of treatment does not cause new resistant bacteria, and is hence expected as a new method of treating bacterial infection in the modern medicine in which there is difficulty in treatment of resistant bacteria.

Meanwhile, NPL 1 discloses an absorption spectrum of PpIX. It is described that light absorption peaks of the PpIX are at positions with wavelengths of 410 nm, 510 nm, 545 nm, 580 nm, and 635 nm.

The phototherapy is generally utilized for various objects of treatment for disease such as neonatal jaundice, psoriasis, or acne, alleviation of pain, cosmetics, and the like. Green light and blue-white light are used for treatment for neonatal jaundice, ultraviolet light is used for treatment for psoriasis, and blue light, red light, and yellow light are used for treatment for acne. Red light is used for treatment for early-stage lung cancer (stage 0 or stage 1 lung cancer), superficial esophageal cancer, superficial early-stage gastric cancer, initial cervical cancer, and dysplasia. In this manner, various light sources are used in accordance with intended use.

In order to spread such a technique, a light irradiating device capable of uniformly radiating light to affected parts having various three-dimensional shapes and sizes is required.

A device using a light source such as an excimer lamp or an arc lamp, a device using laser as a light source, a device of a system in which therapeutic light is radiated planarly by using an optical fiber, and the like have been known as the existing light irradiating device.

CITATION LIST

Patent Literature

PTL 1: Japanese Unexamined Patent Application Publication No. 9-38221 (published on Feb. 10, 1997)
PTL 2: Japanese Unexamined Patent Application Publication No. 11-192315 (published on Jul. 21, 1999)
PTL 3: Japanese Unexamined Patent Application Publication (Translation of PCT Application) No. 2007-518467 (published on Jul. 12, 2007)
PTL 4: Japanese Unexamined Patent Application Publication (Translation of PCT Application) No. 2013-532503 (published on Aug. 19, 2013)
PTL 5: Japanese Unexamined Patent Application Publication No. 2015-24060 (published on Feb. 5, 2015)

Non Patent Literature

NPL 1: https://www.osaka-cu.ac.jp/ja/news/2014/files/setumei_140819.pdf

SUMMARY OF INVENTION

Technical Problem

However, particularly, in a case where phototherapy is applied to topical disease having a relatively small area of about several cm, the existing light irradiating device described above has a problem as follows.

In a case where a light source of a lamp type, such as an excimer lamp or an arc lamp, is used, an irradiation area is too large and a part other than an affected part is irradiated with light, so that there is a concern about various side effects on a normal part. Thus, some shielding countermeasures need to be taken to prevent irradiation to the normal part with therapeutic light, and treatment takes time and effort. For example, in a case where disease developed in a part of a face is treated, a mask for eyes (blindfold) with which eyes that are normal parts are protected is necessary, and, furthermore, a mask by which only an affected part of the face is exposed is also necessary in order to protect normal parts of the face. Moreover, for the treatment, a patient is required to keep his/her posture without moving for several tens of minutes in a state where his/her body is restrained, and such an experience is not pleasant even for the treatment. In a case where an affected part has a curved surface, for example, such as an arm, a foot, a face, or a buttock, the irradiating device of the lamp type may force a patient to take an unnatural posture depending on a part such as a front part, a rear part, or a side part. In addition, in accordance with an angle or a distance to the lamp of the affected part having the curved part, irradiation intensity varies depending on a position of the affected part, so that it is difficult to irradiate the entirety of the affected part with uniform therapeutic light in some cases. Further, the device using such a light source of the lamp type has many accompanying devices such as a power source and a cooling device and is large-sized, so that a large space is required for installation and a price of the device becomes high. Thus, the device is able to be installed only in a therapeutic facility and it is necessary to go to the facility regularly.

In a device using laser as a light source, since irradiation light thereof is spot light whose irradiation area is small, scanning of the spot light is necessary for irradiation to the entirety of an affected part having a large area with therapeutic light, so that the device becomes complicated and expensive.

In a device of a system in which therapeutic light is radiated planarly by using an optical fiber, since efficiency of sending light to the optical fiber is relatively low, irradiation power with therapeutic light cannot be prevented from becoming low, so that the device is suitable only for treatment for a relatively long time.

Thus, a flexible substrate that is able to keep a constant distance from an affected part (make contact with the affected part, in some cases) and cover the affected part along a shape of the affected part and that includes a light source capable of uniform light irradiation has been demanded.

Note that, for such a demand, some techniques as described below have been proposed.

PTL 1 discloses a phototherapy machine that is formed in a shape of a planar light source belt (girdle) or clothing such as a gown, and has a free shape and is also bendable with multiple LEDs being mounted on a flexible substrate. However, PTL 1 does not disclose using light with two wavelengths for treatment or does not include specific disclosure about performing efficient and uniform light irradiation for an affected part.

PTL 2 discloses a thermotherapy machine in which near infrared LEDs are mounted on a flexible substrate. However, there is no disclosure about using light with two wavelengths for treatment or specific disclosure about performing efficient and uniform light irradiation for an affected part.

PTL 3 discloses a therapeutic machine in which organic EL that emits light with two or more wavelengths is mounted on a flexible substrate. There is disclosure about using LED light with two wavelengths for treatment, but there is no specific disclosure about performing efficient and uniform light irradiation for an affected part.

PTL 4 discloses a medical apparatus that has a disposable adhesive sheet and uses light. However, there is no disclosure about using LED light with two wavelengths for treatment or specific disclosure about performing efficient and uniform light irradiation for an affected part.

PTL 5 discloses a phototherapy machine for treatment for jaundice, in which a blue LED and a green LED are combined. There is disclosure about using LED light with two wavelengths for treatment, but the LEDs are not flexible LEDs and there is no specific disclosure about performing efficient and uniform light irradiation for an affected part.

That is, none of the techniques solve the problem to be solved in the present application or is being widely used.

The invention was made in view of the aforementioned problems and an object thereof is to provide a light irradiating device and a phototherapy machine that are able to realize light irradiation with two wavelengths that is suitable for treatment for a relatively small diseased part and is performed almost uniformly and efficiently for the entirety of an affected part even when the affected part is not flat.

Solution to Problem

In order to solve the aforementioned problems, a light irradiating device according to an aspect of the invention includes a group of LED light sources that has at least one LED light source two-dimensionally arranged on a flexible substrate, in which light output by the group of LED light sources includes first wavelength region light whose light-emission intensity peak is in a wavelength range of 380 nm or more and 430 nm or less, and second wavelength region light whose light-emission intensity peak is in a wavelength range of more than 430 nm and 635 nm or less, and the group of LED light sources has uniform in-plane intensity of light irradiation.

Note that, in the present specification, uniform in-plane intensity of light irradiation is achieved, for example, in an area surrounded by center lines of LED chips 5 in an outermost peripheral part as illustrated in FIG. 21, 1. in a case where in-plane uniformity $U_1$ of first wavelength region light and in-plane uniformity $U_2$ of second wavelength region light satisfy $$U_1 = 0.5 \leq \int P_1(\lambda)/\int P_{1max}(\lambda)d\lambda \leq 1 \qquad \text{formula (1) and}$$

$$U_2 = 0.5 \leq \int P_2(\lambda)d\lambda/\int P_{2max}(\lambda)d\lambda \leq 1 \qquad \text{formula (2),}$$

where irradiance (mW/cm²) of (first wavelength region) light in a wavelength range of 380 nm or more and 430 nm or less is $P_1(\lambda)$, irradiance of (second wavelength region) light whose wavelength range is more than 430 nm and 635 nm or less is $P_2(\lambda)$, maximum in-plane irradiance of the first wavelength region light is $P_{1max}(\lambda)$, maximum in-plane irradiance of the second wavelength region light is $P_{2max}(\lambda)$, and an absorption coefficient of PpIX is $\alpha(\lambda)$.

In a case where $U_1$ and $U_2$ are smaller than 0.5, minimum irradiance $P_{min}$, is indicated by $$P_{min} = J_{min}/t,$$

where minimum light energy density is $J_{min}$ (that is decided by a type of a photosensitizing substance and a target disease) and a light irradiation time is t. In order to perform light irradiation with the minimum irradiance or more in a plane of an irradiated object, irradiance that is greater than at least twice the minimum irradiance is required. In a case where light is too strong in phototherapy, pain unbearable for all people is considered to be provided depending on a type of a photosensitizing substance. Thus, $U_1$ and $U_2$ are desirably 0.5 or more.

Most desirably, $U_1$ and $U_2$ are 0.7 or more, because in a case where $U_1$ and $U_2$ are 0.5 or more and smaller than 0.7, it is considered that some people suffer from unbearable pain. Thus, it is more desirable that $U_1$ and $U_2$ are 0.7 or more.

Alternatively, uniform in-plane intensity of light irradiation is achieved, 2. in a case where uniformity $U_3$ of energy density of first wavelength region light and uniformity $U_4$ of energy density of second wavelength region light satisfy $$U_3 = 0.5 \leq \int J_1(\lambda)/\int J_{1max}(\lambda)d\lambda \leq 1 \qquad \text{formula (3) and}$$

$$U_4 = 0.5 \leq \int J_2(\lambda)d\lambda/\int J_{2max}(\lambda)d\lambda \leq 1 \qquad \text{formula (4),}$$

where the energy density $J_1(\lambda)$ of the first wavelength region light and the energy density $J_2(\lambda)$ of the second wavelength region light are respectively expressed as $J_1(\lambda) = \int P_1(\lambda)dt$ and $J_2(\lambda) = \int P_2(\lambda)dt$, and maximum in-plane energy density of the first wavelength region light is $J_{1max}(\lambda)$ and maximum in-plane energy density of the second wavelength region light is $J_{2max}(\lambda)$.

In a case where $U_3$ and $U_4$ are smaller than 0.5, energy density, that is, irradiance that is greater than at least twice minimum light energy density is required in a plane of an irradiated object (affected part). In a case where light is too strong in phototherapy, pain unbearable for all people is considered to be provided depending on a type of a photosensitizing substance. Thus, $U_3$ and $U_4$ are desirably 0.5 or more.

Most desirably, $U_3$ and $U_4$ are 0.7 or more, because in a case where $U_3$ and $U_4$ are 0.5 or more and smaller than 0.7, it is considered that some people suffer from unbearable pain. Thus, it is more desirable that $U_3$ and $U_4$ are 0.7 or more.

Alternatively, uniform in-plane intensity of light irradiation is achieved, 3. in a case where in-plane light uniformity $U_5$ of first wavelength region light and in-plane light uniformity $U_6$ of second wavelength region light satisfy $$U_5 = 0.5 \leq \int P_1(\lambda)\alpha(\lambda)d\lambda / \int P_{1max}(\lambda)\alpha(\lambda)d\lambda \leq 1 \quad \text{formula (5)}$$

and $$U_6 = 0.5 \leq \int P_2(\lambda)\alpha(\lambda)d\lambda / \int P_{2max}(\lambda)\alpha(\lambda)d\lambda \leq 1 \quad \text{formula (6),}$$

where, in a case where a photosensitizing substance such as porphyrin IX (PpIX) is used, an absorption coefficient of the PpIX is $\alpha(\lambda)$.

In a case where $U_5$ and $U_6$ are smaller than 0.5, in order to perform light irradiation with minimum irradiance or more in a plane of an irradiated object, irradiance that is greater than at least twice the minimum irradiance is required. In a case where light is too strong in phototherapy, pain unbearable for all people is considered to be provided depending on a type of a photosensitizing substance. Thus, $U_5$ and $U_6$ are desirably 0.5 or more.

Most desirably, $U_5$ and $U_6$ are 0.7 or more, because in a case where $U_5$ and $U_6$ are 0.5 or more and smaller than 0.7, it is considered that some people suffer from unbearable pain. Thus, it is more desirable that $U_5$ and $U_6$ are 0.7 or more.

Alternatively, uniform in-plane intensity of light irradiation is achieved, 4. in a case where in-plane energy uniformity $U_7$ of first wavelength region light and in-plane energy uniformity $U_8$ of second wavelength region light satisfy $$U_7 = 0.5 \leq \int J_1(\lambda)\alpha(\lambda)d\lambda / \int J_{1max}(\lambda)\alpha(\lambda)d\lambda \leq 1 \quad \text{formula (7)}$$

and $$U_8 = 0.5 \leq \int J_2(\lambda)\alpha(\lambda)d\lambda / \int J_{2max}(\lambda)\alpha(\lambda)d\lambda \leq 1 \quad \text{formula (8),}$$

where a photosensitizing substance is used similarly to the case of "3".

In a case where $U_7$ and $U_8$ are smaller than 0.5, energy density, that is, irradiance that is greater than at least twice minimum light energy density is required in a plane of an irradiated object (affected part). In a case where light is too strong in phototherapy, pain unbearable for all people is considered to be provided depending on a type of a photosensitizing substance. Thus, $U_7$ and $U_8$ are desirably 0.5 or more.

Most desirably, $U_7$ and $U_8$ are 0.7 or more, because in a case where $U_7$ and $U_8$ are 0.5 or more and smaller than 0.7, it is considered that some people suffer from unbearable pain. Thus, it is more desirable that $U_7$ and $U_8$ are 0.7 or more.

In order to solve the aforementioned problems, a phototherapy machine according to another aspect of the invention includes the light irradiating device according to the one aspect of the invention.

Advantageous Effects of Invention

According to each aspect of the invention, it is possible to realize light irradiation that is suitable for treatment for a relatively small diseased part and is performed almost uniformly and efficiently for the entirety of an affected part even when the affected part is not flat.

DESCRIPTION OF EMBODIMENTS

Hereinafter, embodiments of the invention will be described in detail. Note that, dimensions, materials, shapes, relative positions, processing processes, and the like of constituents described in the embodiments below are merely embodiments, and should not be considered as limiting the scope of the invention only to them. Furthermore, drawings are schematically illustrated, and ratios of dimensions and shapes are different from actual ones.

Embodiment 1

An embodiment of the invention will be described as follows with reference to FIGS. 1 to 3. Note that, description will be given below by setting that a surface of a light irradiating substrate, on which an LED (light-emitting diode) is mounted, is a front surface (first surface) and a surface opposite to the surface on which an LED chip is mounted is a rear surface (second surface).

(Light Irradiating Substrate 1)

Figure 1:
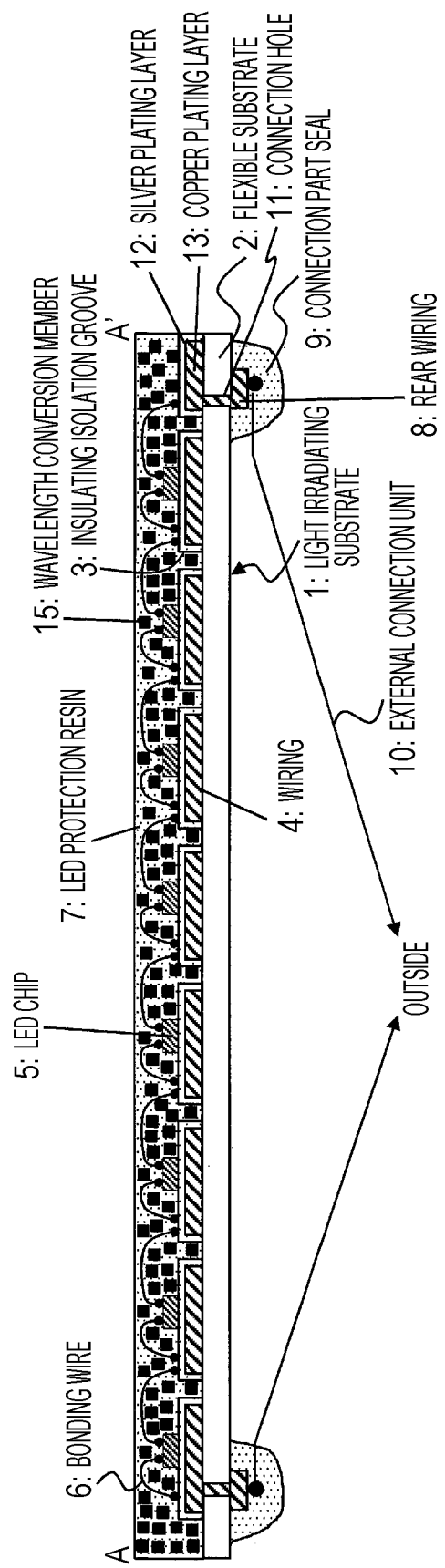
FIG. 1 is a schematic sectional view illustrating a configuration of a light irradiating substrate according to Embodiment 1 of the invention.

FIG. 1 is a schematic sectional view illustrating a configuration of a light irradiating substrate (light irradiating device) 1 according to the present embodiment. FIG. 2 is a schematic front surface view illustrating the configuration of the light irradiating substrate 1 according to the present embodiment. FIG. 3 is a schematic front surface view illustrating the configuration of the light irradiating substrate 1 according to the present embodiment.

Figure 2:
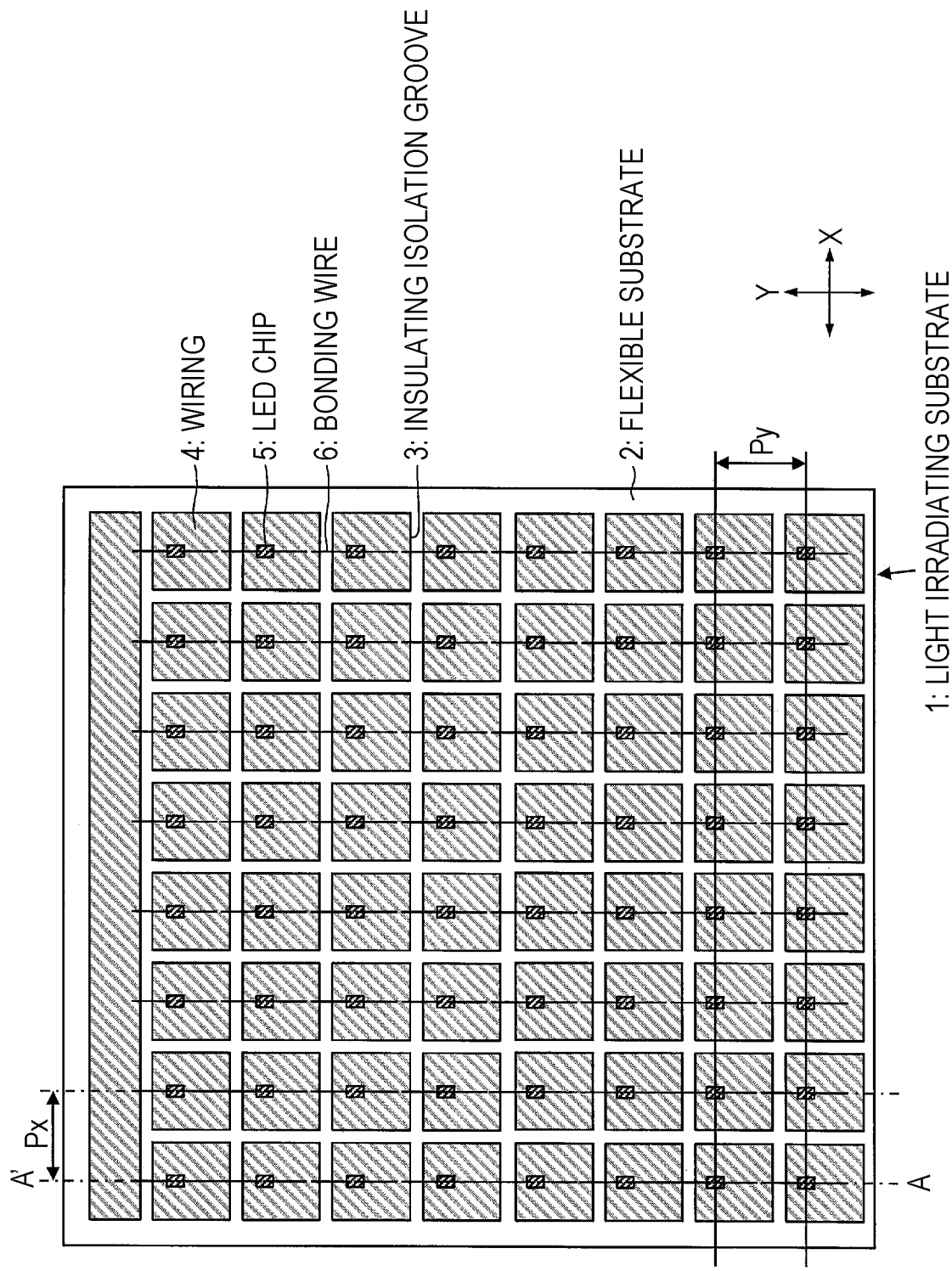
FIG. 2 is a schematic front surface view illustrating the configuration of the light irradiating substrate according to Embodiment 1 of the invention.

FIG. 1 corresponds to a sectional view taken along a line A-A' of the light irradiating substrate 1, which is illustrated in FIG. 2. Note that, for convenience of illustration, illustration of LED protection resin 7 is omitted in FIG. 2.

Figure 3:
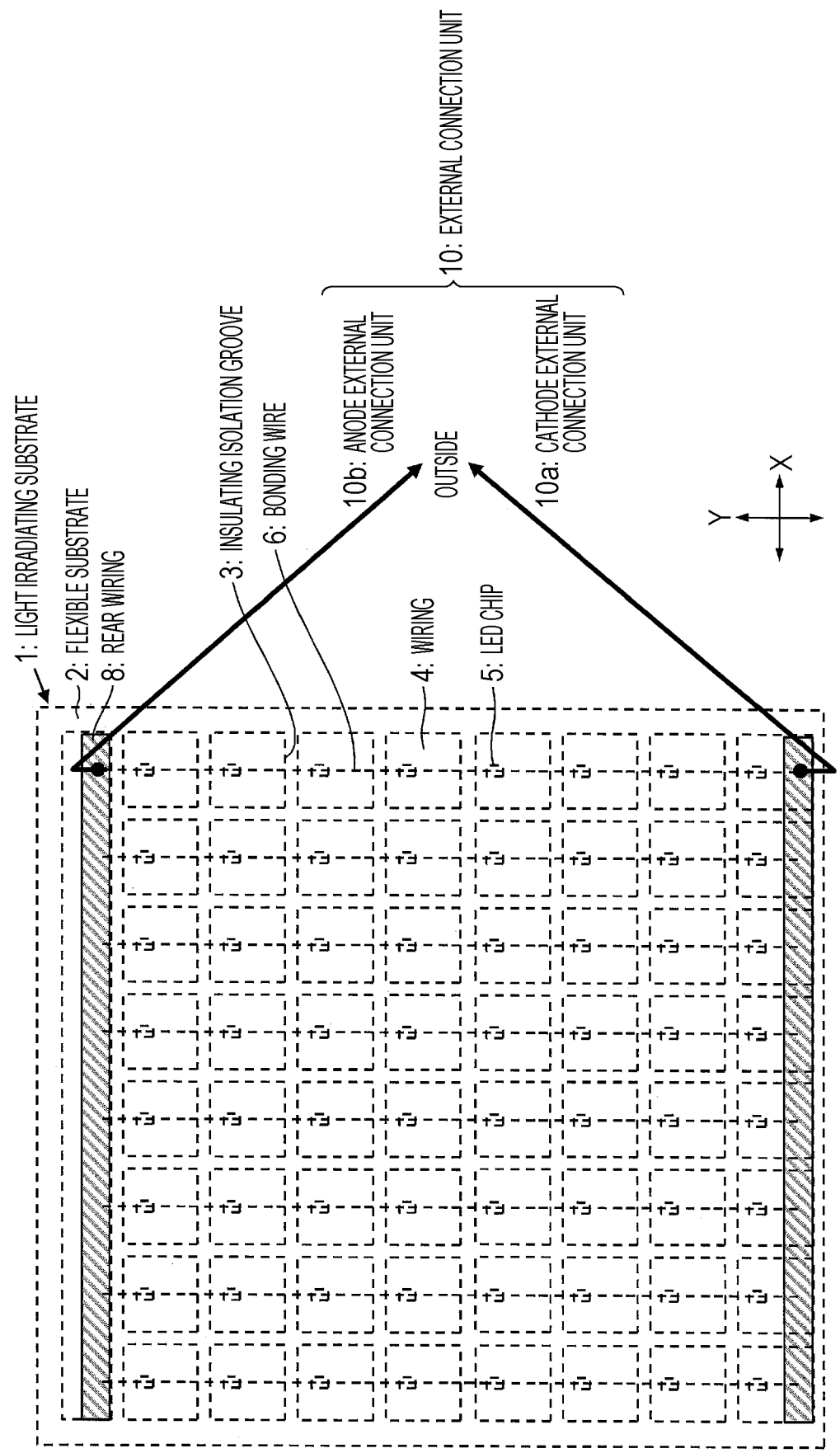
FIG. 3 is a schematic rear surface view illustrating the configuration of the light irradiating substrate according to Embodiment 1 of the invention.

As illustrated in FIGS. 1 to 3, the light irradiating substrate 1 includes a flexible substrate 2, a plurality of wirings (wiring pattern, first surface wirings) 4 that are insulated and isolated from each other by an insulating isolation groove 3, a plurality of LED chips (LED elements) 5, a plurality of bonding wires 6, the LED protection resin 7, a wavelength conversion member 15, a plurality of rear wirings 8, a connection part seal 9, and an external connection unit 10. A set of all the LED chips 5 corresponds to a group of LED light sources according to the invention.

The wirings 4 are formed on one main surface (front surface, first surface) of the flexible substrate 2. The LED chips 5 each serving as a light source are mounted on the wirings 4. The respective wirings 4 are insulated and isolated by the insulating isolation groove 3, and one LED chip 5 is mounted on one wiring 4. Each of the LED chips 5 is connected by the bonding wires 6 to a wiring 4 on which the LED chip 5 is mounted and to another wiring 4 which is adjacent to the wiring 4 in a Y direction via the insulating isolation groove 3. The plurality of LED chips 5 are two-dimensionally arranged on the flexible substrate 2 as described below.

The LED chips 5 and the bonding wires 6 are covered with the LED protection resin 7 serving a protective film. The LED protection resin 7 includes the wavelength conversion member 15 that absorbs first wavelength region light output from the LED chips 5 and thereby outputs second wavelength region light. The first wavelength region light and the second wavelength region light will be described in detail below.

On the other hand, the rear wirings 8 are formed on the other main surface (rear surface, second surface) of the flexible substrate 2.

Connection holes 11 that pass through the flexible substrate 2 are formed in the flexible substrate. The wirings 4 and the rear wirings 8 are connected via the connection holes 11. The wirings 4 are electrically connected to the external connection unit 10 via the rear wirings 8. Wire connection parts between the external connection unit 10 and the rear wirings 8 are insulated and isolated by the connection part seal 9.

Next, each constituent of the light irradiating substrate 1 will be described in more detail.

(Flexible Substrate 2)

The flexible substrate 2 is an insulating substrate, and is formed of an insulating film, for example, such as polyimide. However, a material of the flexible substrate 2 is not necessarily limited to the polyimide, and any material is able to be used as long as being an insulating material and having necessary strength and flexibility. In addition to a polyimide resin film, various materials, for example, such as a film of fluororesin, silicone resin, polyethylene terephthalate resin, or the like, a highly reflective resin film obtained by applying resin (white resin, white resist, or the like) including a white pigment to a surface of such a film, and a highly reflective resin film in which a white pigment is mixed are able to be used as the aforementioned flexible substrate 5. A highly reflective material is expensive, but has high reflectivity of a substrate and achieves improvement of efficiency of light irradiation. For inexpensive transparent resin, a measure against light leaking out to a rear surface of a substrate is required in some cases.

Affected parts to which phototherapy is applied have various shapes, sizes, and areas. Accordingly, neither a size of the flexible substrate 2 nor a shape of the flexible substrate 2 is particularly limited. Since the flexible substrate 2 is required only to have a size that allows covering an affected part, when the light irradiating substrate 1 has a size that allows light irradiation with only the affected part covered, it is possible to make a patient less restrained and suppress a burden of the patient to a minimum.

The light irradiating substrate 1 is suitably used for topical disease having a relatively small area of about several cm. It is desired that the flexible substrate 2 is formed to have a size corresponding to the topical disease.

A thickness of the flexible substrate 2 is not particularly limited as long as necessary strength and flexibility are provided. In the present embodiment, a film having a thickness of 50 μm is used, but may have a different thickness.

(Wiring 4)

The wirings 4 each of which is formed of a silver plating layer 12 and a copper plating layer 13 (copper plating wiring, first electrical conducting material) whose front surface is covered with the silver plating layer 12 are formed on the flexible substrate 2.

The wirings 4 are able to be formed, for example, by applying copper plating to the front surface of the flexible substrate 2 formed of a polyimide film, forming the insulating isolation groove 3 to thereby form the copper plating layer 13 which has been patterned, and applying silver plating to a front surface of the copper plating layer 13.

A material of the wirings is required to have a low resistance and have high reflectance of front surfaces thereof. Particularly, in order to reduce a loss during light irradiation, it is necessary to minimize an energy loss due to reflection. Thus, total light flux reflectance needs to be at least 80%, and desirably 90% or more. In this case, the total light flux reflectance does not indicate reflectance of specular reflection but a ratio of light energy obtained by integrating all reflected light, which is diffused and reflected, to energy of incident light.

Accordingly, at least for the front surfaces of the wirings 4 on a front side of the flexible substrate 2, a reflecting material (hereinafter, referred to as "high reflectance material") having total light flux reflectance of 80% or more, desirably a high reflectance material having total light flux reflectance of 90% or more is used, so that light reflected by an affected part is reflected as much as possible to be returned to the affected part and a loss of light is suppressed to a minimum.

In a case where the wirings 4 do not have the silver plating layer 12 on the front surfaces thereof, there is a case where light absorption by the copper plating layer 13 is caused and irradiation time by the light irradiating substrate 1 needs to be made 1.2 times longer.

Note that, for the aforementioned high reflectance material, a material of regular reflection may be used, or a material of diffuse reflection may be used. In the present embodiment, copper wirings which are formed of the copper plating layer 13 to the front surface of which the silver plating is applied are used as the wirings 4 as described above, but a material such as aluminum may be used for the wirings 4 or the front surfaces of the wirings 4, for example.

Hereinafter, a wiring pattern formed by the wirings 4 is referred to as a first electrical conducting material pattern 14. In the present embodiment, for improving efficiency of light irradiation, it is important that the first electrical conducting material pattern 14 covers the front surface of the flexible substrate 2 over an area as large as possible.

(LED Chip 5 and Bonding Wire 6)

The LED chips 5 need to be selected in accordance with an object of treatment. In the present embodiment, an LED chip having a peak (light-emission intensity peak) wavelength of 405 nm is selected. The peak wavelength is not limited to 405 nm as long as the wavelength conversion member 15 is able to be excited.

In order to uniformly perform light irradiation for an affected part having a fixed size as in phototherapy, arranging a large number of LED chips 5 which are relatively small is better than using a small number of high-power (large-sized) LED chips 5. In the present embodiment, 64 LED chips each of which has a size of 440 μm×550 μm are mounted on the flexible substrate 2 as the plurality of LED chips 5.

As illustrated in FIG. 2, the LED chips 5 are arranged in a two-dimensional array (two-dimensional arrangement) in which 8 pieces×8 pieces are provided along an X direction (first direction) and a Y direction (second direction) which is in the same plane as the X direction and orthogonal to the X direction. As illustrated in FIG. 2, when it is set that each pitch between the LED chips 5 that are adjacent to each other in the X direction is Px and each pitch between the LED chips 5 that are adjacent to each other in the Y direction which is orthogonal to the X direction is Py, the LED chips 5 are arranged in a two-dimensional array at almost constant pitch (Px, Py).

Note that, the X direction and the Y direction here are array directions of the LED chips 5, and, in the present embodiment, the LED chips 5 are arrayed in parallel to each side of the flexible substrate 2 that is in a rectangular shape (for example, a square shape). Moreover, the pitch between the LED chips 5 that are adjacent to each other in the X direction or the Y direction indicates a distance between the centers of the LED chips 5 that are adjacent to each other in the X direction or the Y direction.

In this manner, by arranging the LED chips 5 in the two-dimensional array at almost constant pitch (Px, Py) in an inside of the light irradiating substrate 1, it is possible to improve uniformity of intensity of light irradiation in the inside of the light irradiating substrate 1.

Note that, although Px=Py is satisfied generally, light output distribution may be different between the X direction and the Y direction depending on shapes of the LED chips 5. In such a case, it is desired that the pitches (Px, Py) between the LED chips 5 are made different between the X direction and the Y direction. For example, in an LED chip 5 that has a long and narrow shape, there is a tendency that light is easily output in a direction perpendicular to a long side thereof and a little light is output in a direction perpendicular to a short side thereof. In a case where the long side of the LED chip 5 is, for example, parallel to the X direction, it is desired that Px<Py is satisfied. For maximum simplification, it is desired that an LED chip 5 whose shape is nearly a square is used and Px=Py is satisfied. Note that, the above-described tendency may be affected by arrangement of electrodes of the LED chips 5. Accordingly, it is desired that optimization is performed in accordance with actual light-emitting characteristics of the LED chips 5.

In the present embodiment, an average pitch between the LED chips 5 is set to be about 5 mm to 10 mm. As the LED chips 5 having such a size, LED chips each having the most common structure in which a nitride semiconductor layer is grown epitaxially on a sapphire substrate and a cathode electrode and an anode electrode are formed on the same plane have the best light-emitting efficiency.

In the present embodiment, the above-described LED chips 5 in each of which the cathode electrode and the anode electrode are formed on the same plane are bonded onto the wirings 4 with transparent die bond paste, and the cathode electrode and the anode electrode of each of the LED chips 5, which are not illustrated, are connected (wired) to the wiring 4 with each of the bonding wires 6 as illustrated in FIGS. 1 to 3.

For the bonding wire 6, gold (gold bonding wire) is used. However, the bonding wire 6 is not necessarily formed of gold, and a publicly known bonding wire formed of silver, aluminum, or the like may be used.

Note that, in a case where the LED chip 5 has a so-called vertical electrode structure, that is, in a case where the LED chip 5 in which the cathode electrode and the anode electrode have the vertical electrode structure is used, a lower surface of the LED chip 5, which serves as a lower electrode of the LED chip 5, is bonded onto the wiring 4 with an electrical conducting material such as silver paste, and an upper electrode is connected to the wiring 4, which is different from the wiring 4 onto which the LED chip 5 is mounted, with the bonding wire 6.

(LED Protection Resin 7 and Wavelength Conversion Member 15)

In order to protect the LED chips 5 and the bonding wires 6, the LED chips 5 and the bonding wires 6 are covered with the LED protection resin 7. The wavelength conversion member 15 is uniformly mixed in the LED protection resin 7. In the present embodiment, the LED protection resin 7 and the wavelength conversion member 15 are stirred and defoamed in advance, and then, sealing is performed.

When a general formula $BaSi_2(O,Cl)_2N_2:Eu$, $(Ba,Sr)MgAl_{10}O_{17}:Eu,Mn$, $(Ba,Sr)Si_2O_4:Eu$, $Sr_4Al_{14}O_{25}:Eu$, $SrAl_2O_4:Eu$, $(Sr,Al)_6(O,N)_8:Eu$, $(Lu,Y,Gd)_3(Al,Ga)_5O_{12}:Ce$, $(Ca_{1.7}Si_{8.2})Al_{3.8}O_{0.3}N_{15.7}:Eu$, $La_3Si_6N_{11}:Ce$, $(Sr,Ca)AlSiN_3:Eu$, or $K_2SiF_6:Mn$ is used as the wavelength conversion member 15, the wavelength conversion member 15 is able to be excited efficiently by light with a wavelength of 405 nm, which is emitted from the LED chip 5. It is also possible to further add the LED chip 5 with a peak wavelength of 450 nm, for example.

Figure 4:
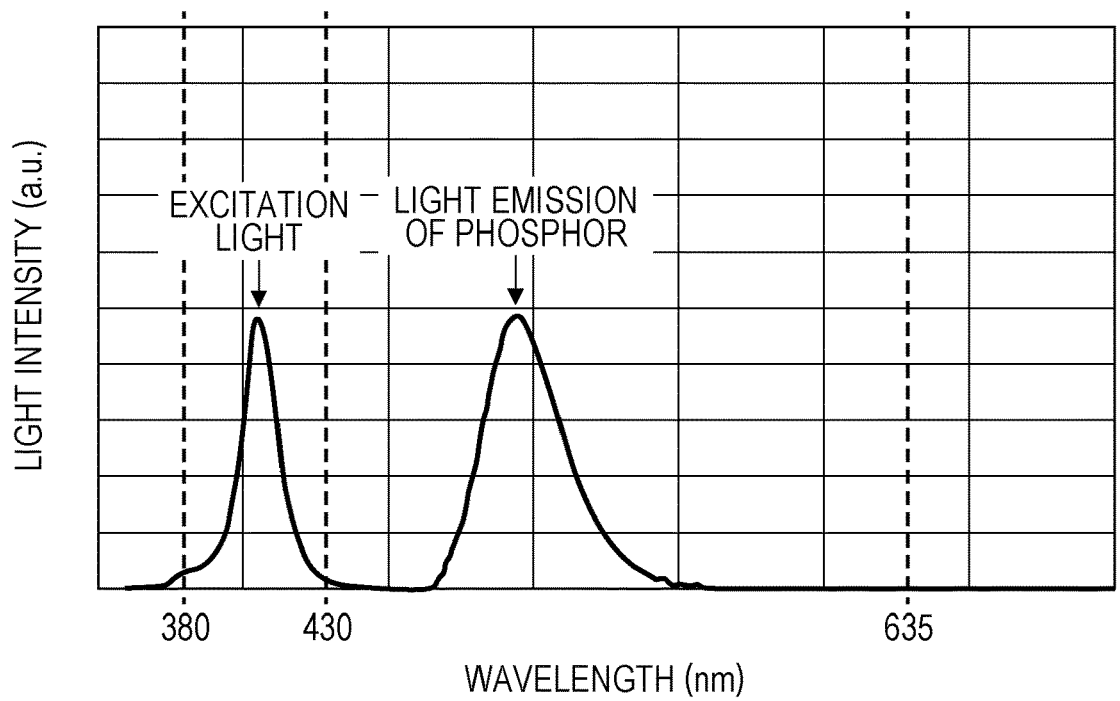
FIG. 4 is a graph illustrating a first example of an emission spectrum of the light irradiating substrate according to Embodiment 1 of the invention.

FIG. 4 illustrates an emission spectrum in a case where a phosphor of $BaSi_2(O,Cl)_2N_2:Eu$ is used.

Figure 5:
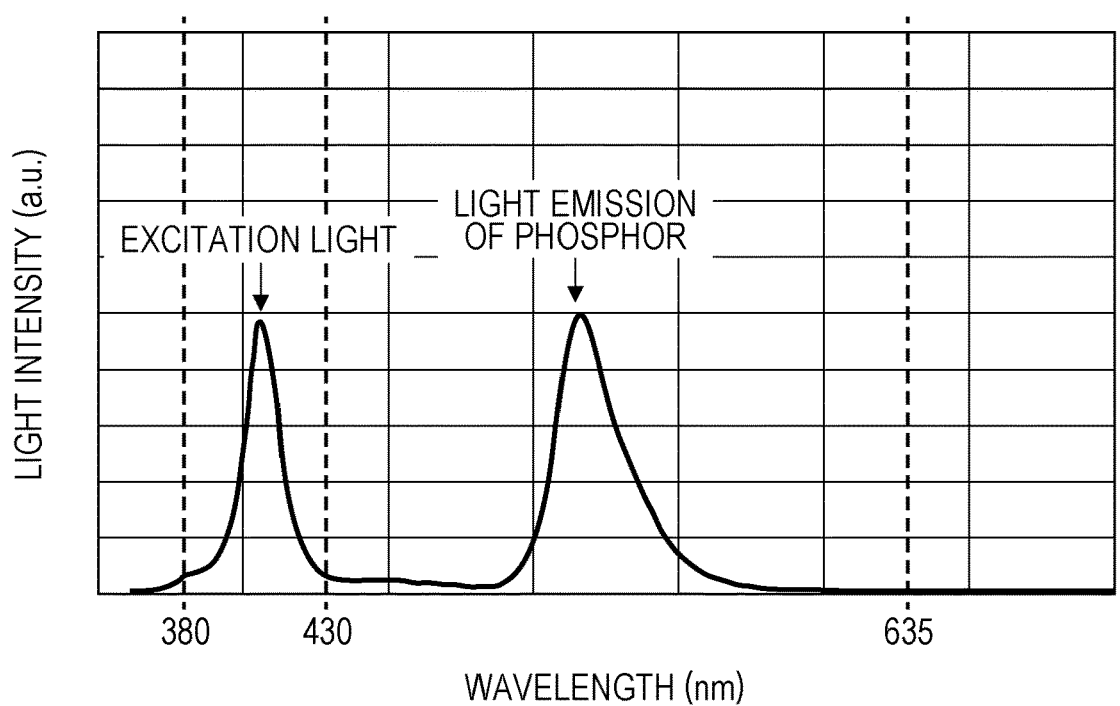
FIG. 5 is a graph illustrating a second example of the emission spectrum of the light irradiating substrate according to Embodiment 1 of the invention.

FIG. 5 illustrates the emission spectrum in a case where a phosphor of $(Ba,Sr)MgAl_{10}O_{17}:Eu,Mn$ is used.

Figure 6:
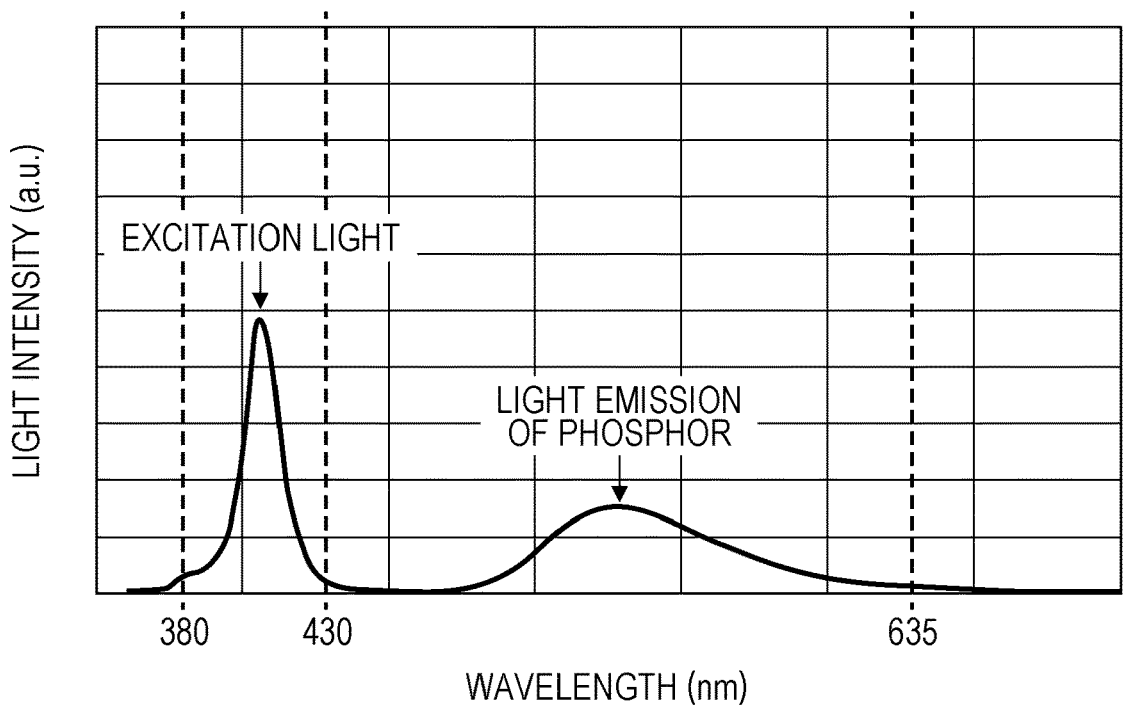
FIG. 6 is a graph illustrating a third example of the emission spectrum of the light irradiating substrate according to Embodiment 1 of the invention.

FIG. 6 illustrates the emission spectrum in a case where a phosphor of $(Ba,Sr)Si_2O_4:Eu$ is used.

Figure 7:
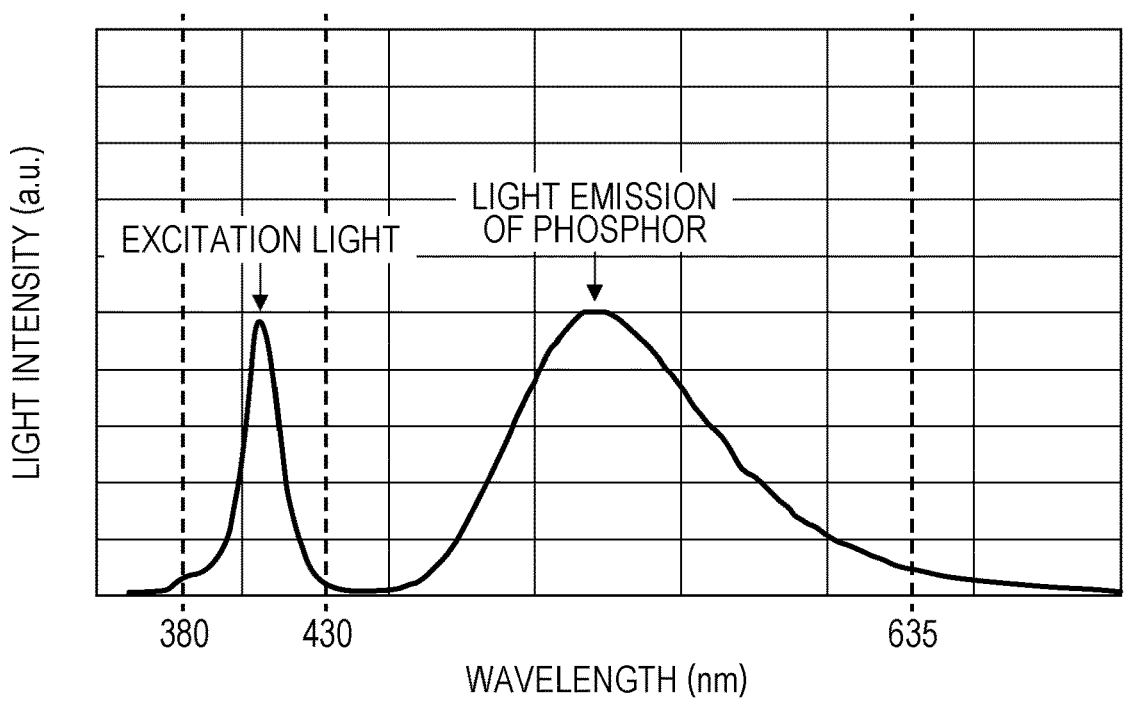
FIG. 7 is a graph illustrating a fourth example of the emission spectrum of the light irradiating substrate according to Embodiment 1 of the invention.

FIG. 7 illustrates the emission spectrum in a case where a phosphor of $SrAl_2O_4:Eu$ is used.

Figure 8:
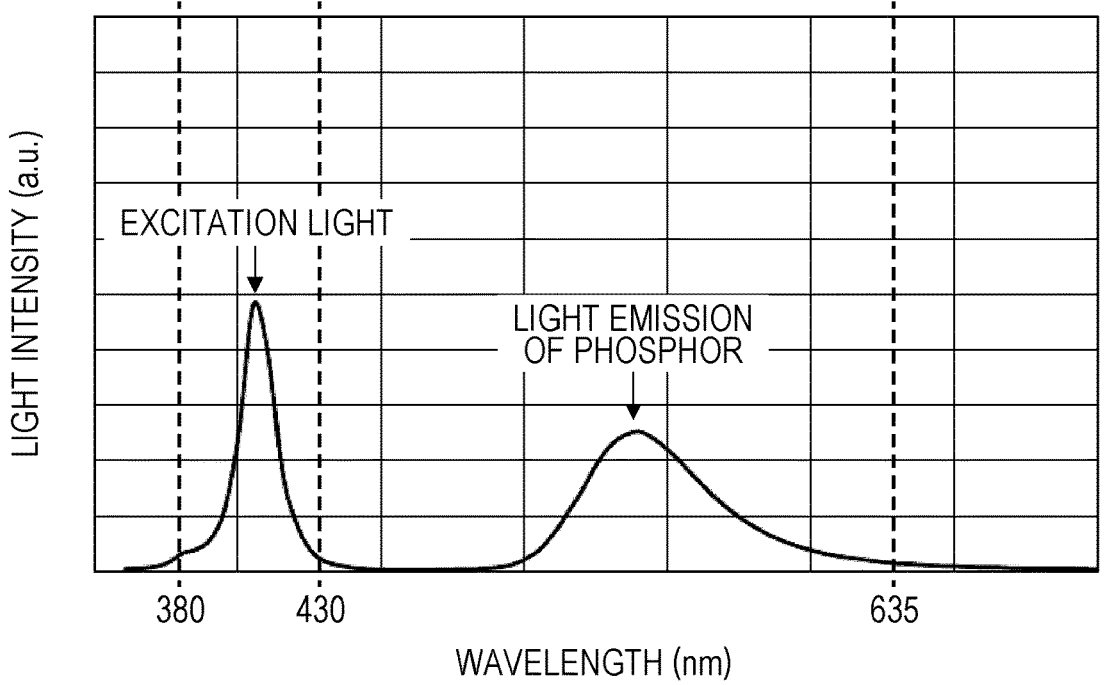
FIG. 8 is a graph illustrating a fifth example of the emission spectrum of the light irradiating substrate according to Embodiment 1 of the invention.

FIG. 8 illustrates the emission spectrum in a case where a phosphor of $(Sr,Al)_6(O,N)_8:Eu$ is used.

Figure 9:
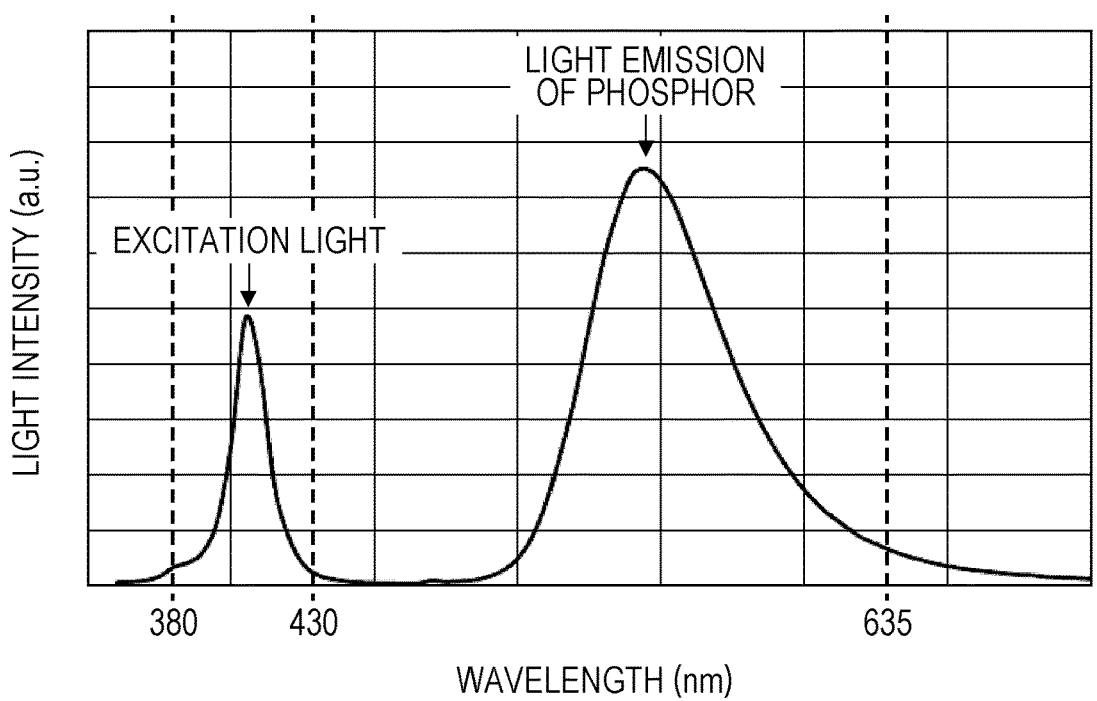
FIG. 9 is a graph illustrating a sixth example of the emission spectrum of the light irradiating substrate according to Embodiment 1 of the invention.

FIG. 9 illustrates the emission spectrum in the case where the phosphor of $(Sr,Al)_6(O,N)_8:Eu$ is used.

Figure 10:
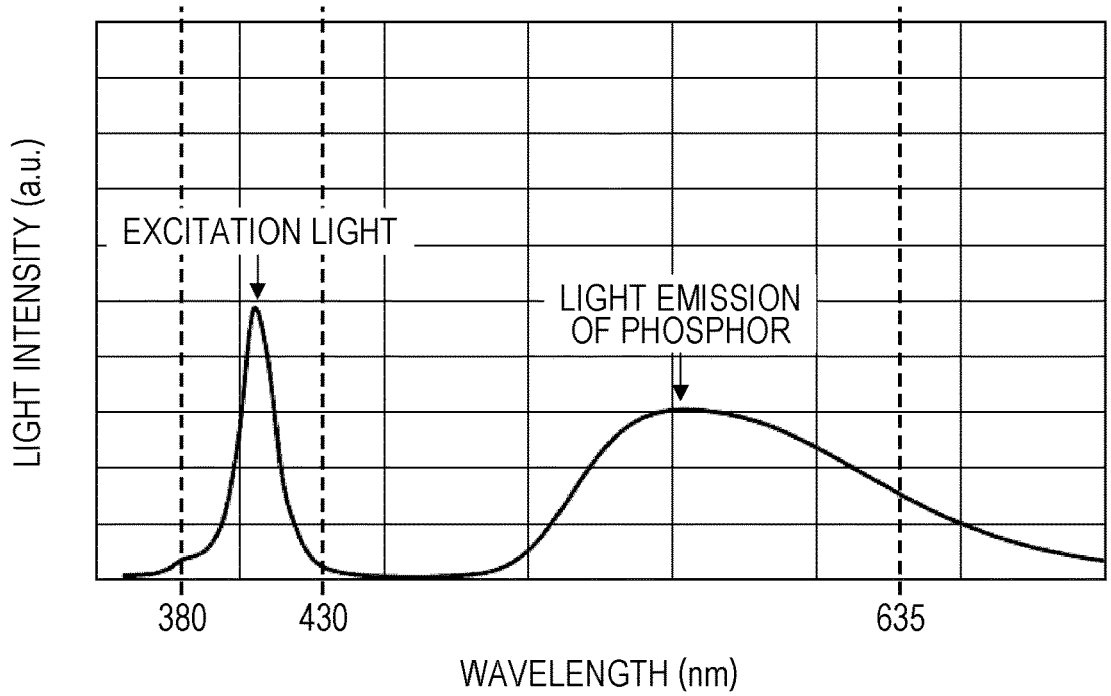
FIG. 10 is a graph illustrating a seventh example of the emission spectrum of the light irradiating substrate according to Embodiment 1 of the invention.

FIG. 10 illustrates the emission spectrum in a case where a phosphor of $(Lu,Y,Gd)_3(Al,Ga)_5O_{12}:Ce$ is used.

Figure 11:
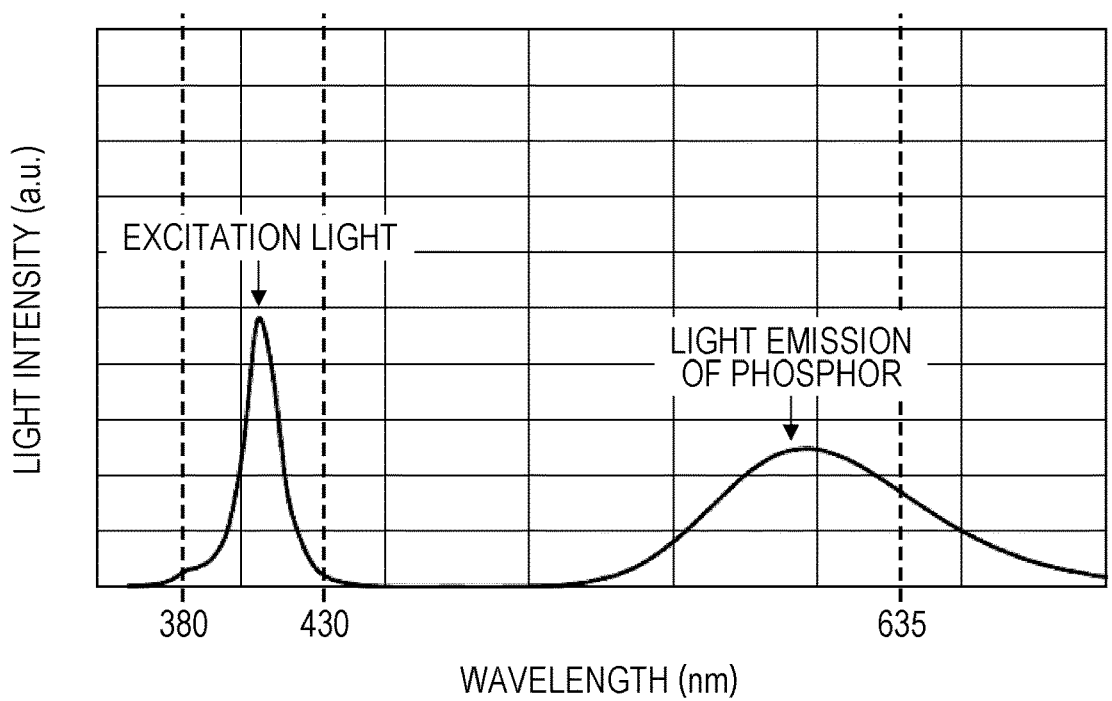
FIG. 11 is a graph illustrating an eighth example of the emission spectrum of the light irradiating substrate according to Embodiment 1 of the invention.

FIG. 11 illustrates the emission spectrum in a case where a phosphor of $(Ca_{1.7}Si_{8.2})Al_{3.8}O_{0.3}N_{15.7}:Eu$ is used.

Figure 12:
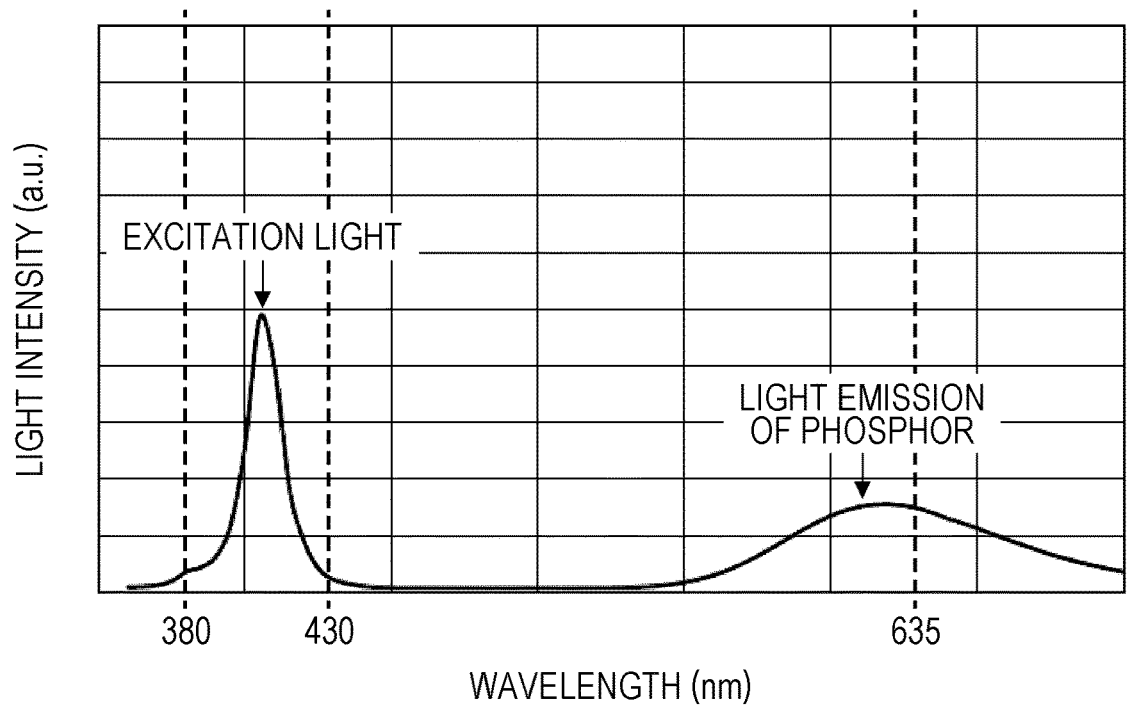
FIG. 12 is a graph illustrating a ninth example of the emission spectrum of the light irradiating substrate according to Embodiment 1 of the invention.

FIG. 12 illustrates the emission spectrum in a case where a phosphor of $(Sr,Ca)AlSiN_3:Eu$ is used.

Figure 13:
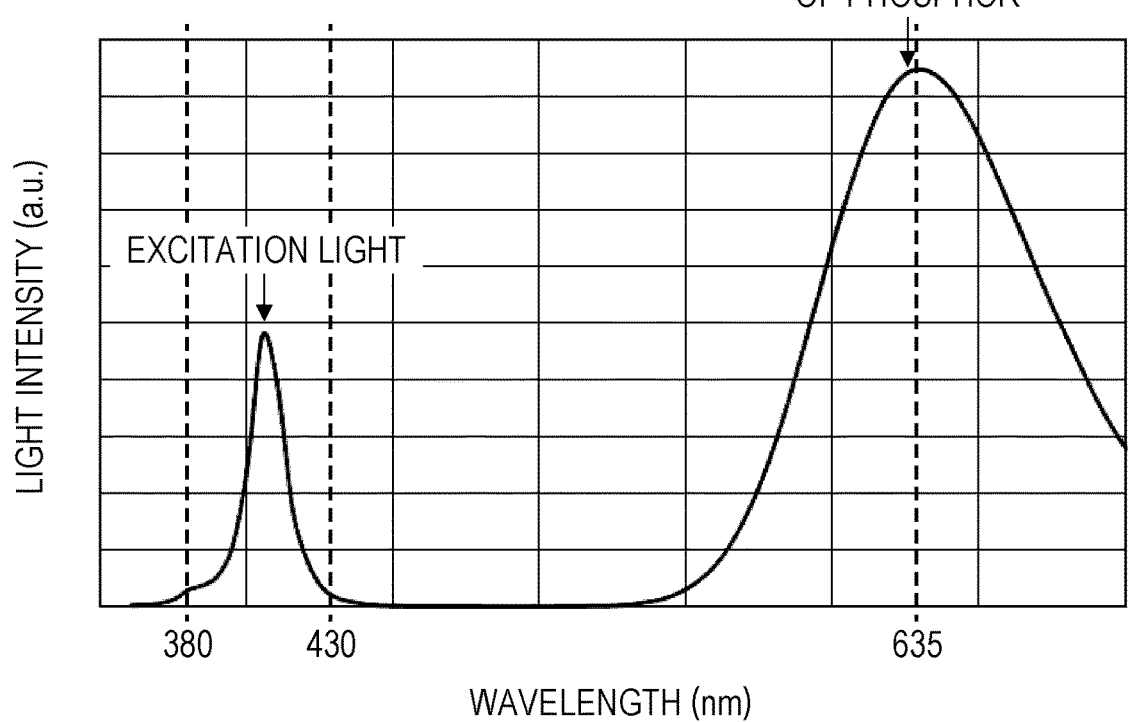
FIG. 13 is a graph illustrating a tenth example of the emission spectrum of the light irradiating substrate according to Embodiment 1 of the invention.

FIG. 13 illustrates the emission spectrum in the case where the phosphor of $(Sr,Ca)AlSiN_3:Eu$ is used.

Figure 14:
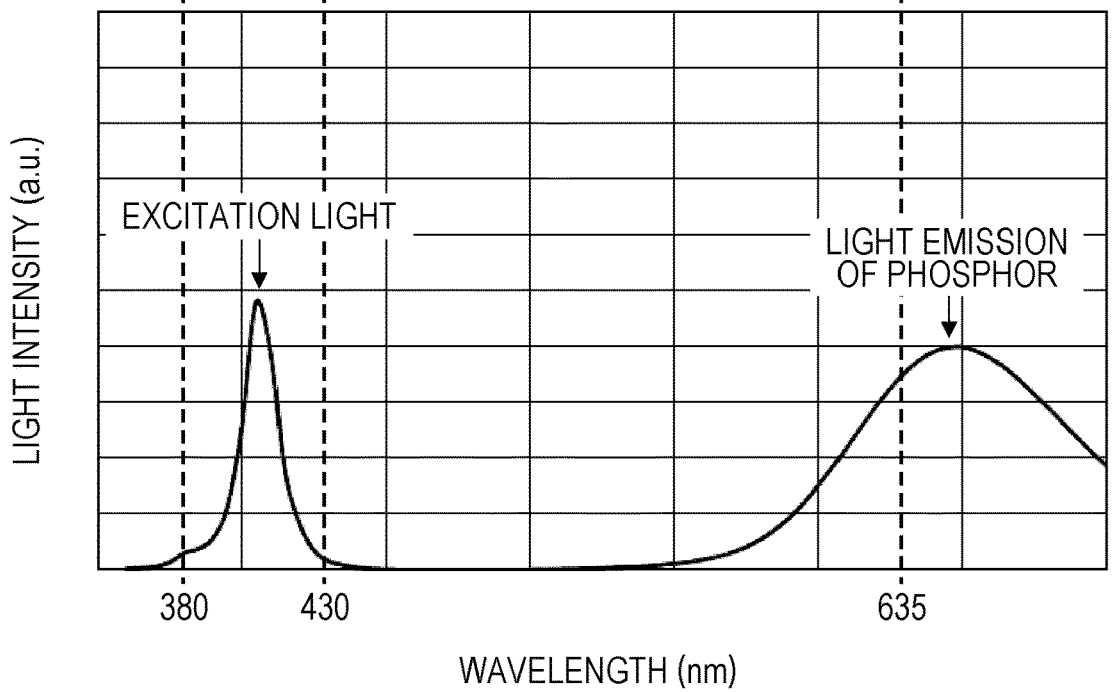
FIG. 14 is a graph illustrating an eleventh example of the emission spectrum of the light irradiating substrate according to Embodiment 1 of the invention.

FIG. 14 illustrates the emission spectrum in the case where the phosphor of $(Sr,Ca)AlSiN_3:Eu$ is used.

Figure 15:
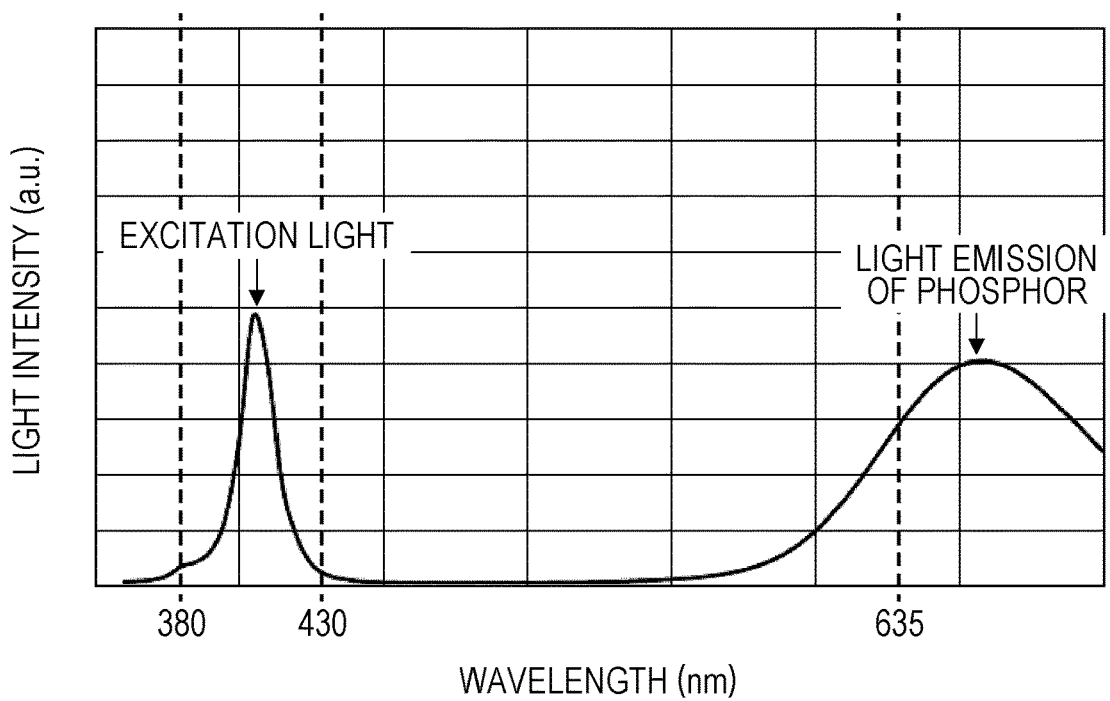
FIG. 15 is a graph illustrating a twelfth example of the emission spectrum of the light irradiating substrate according to Embodiment 1 of the invention.

FIG. 15 illustrates the emission spectrum in the case where the phosphor of $(Sr,Ca)AlSiN_3:Eu$ is used.

Figure 16:
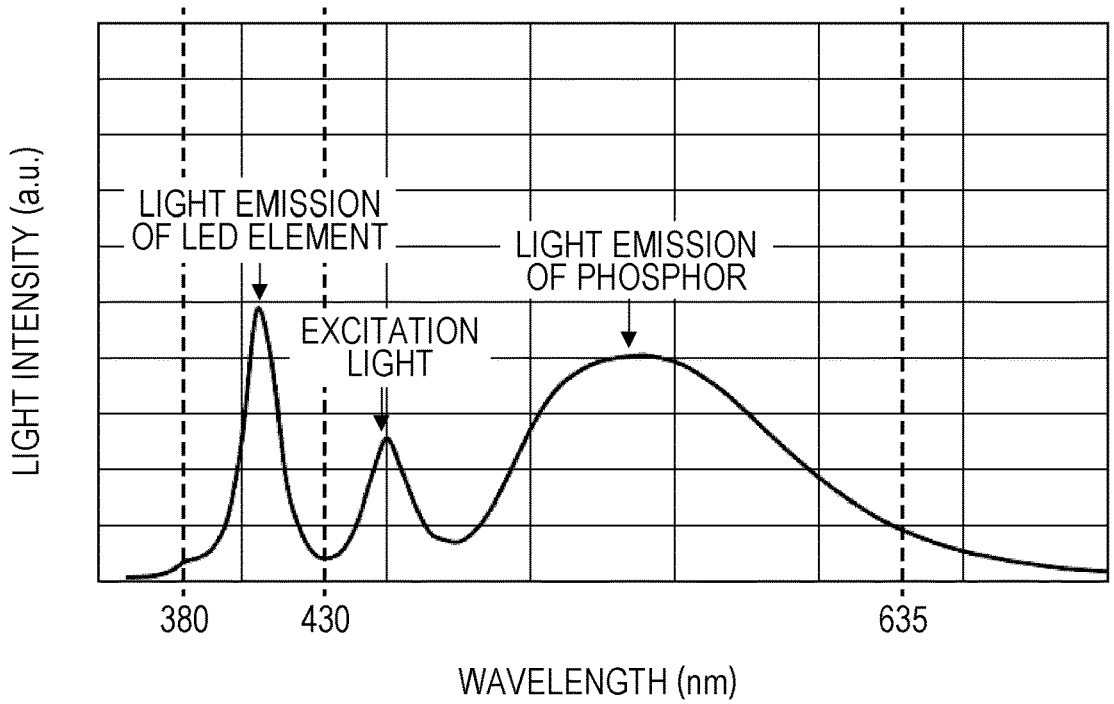
FIG. 16 is a graph illustrating a thirteenth example of the emission spectrum of the light irradiating substrate according to Embodiment 1 of the invention.

FIG. 16 illustrates the emission spectrum in the case where the phosphor of $(Lu,Y,Gd)_3(Al,Ga)_5O_{12}:Ce$ is used.

Figure 17:
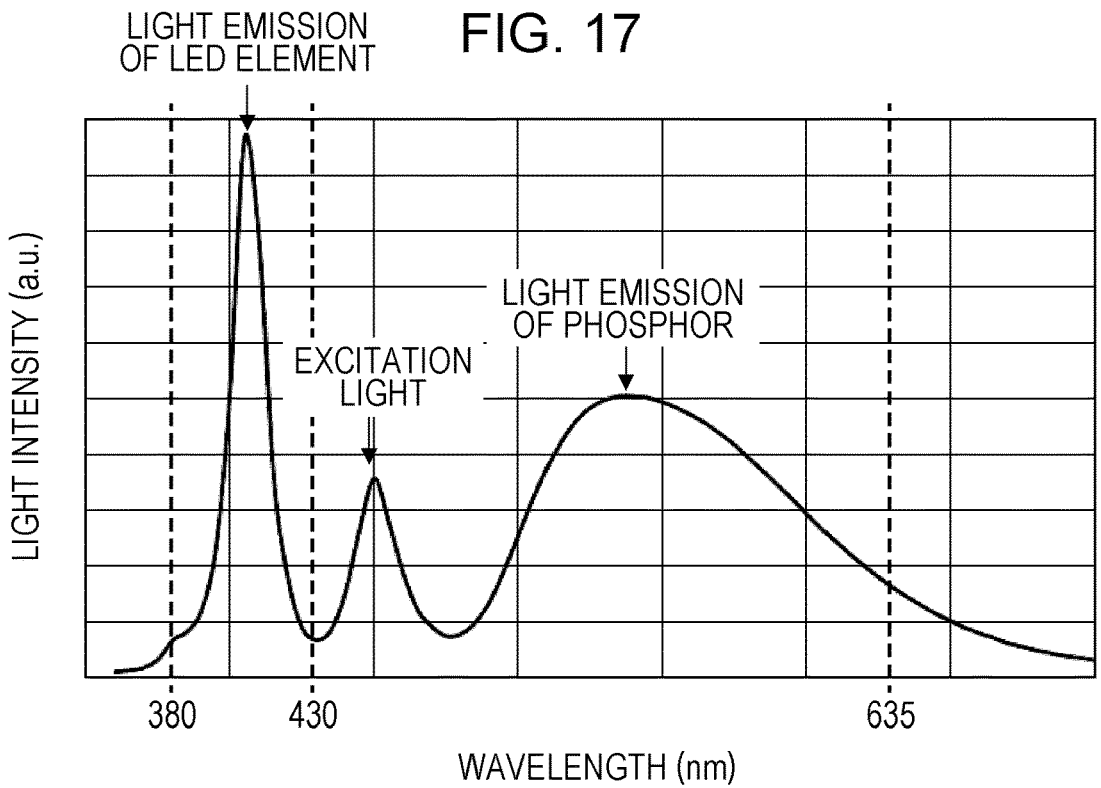
FIG. 17 is a graph illustrating a fourteenth example of the emission spectrum of the light irradiating substrate according to Embodiment 1 of the invention.

FIG. 17 illustrates the emission spectrum in the case where the phosphor of $(Lu,Y,Gd)_3(Al,Ga)_5O_{12}:Ce$ is used.

Figures 18, 19:
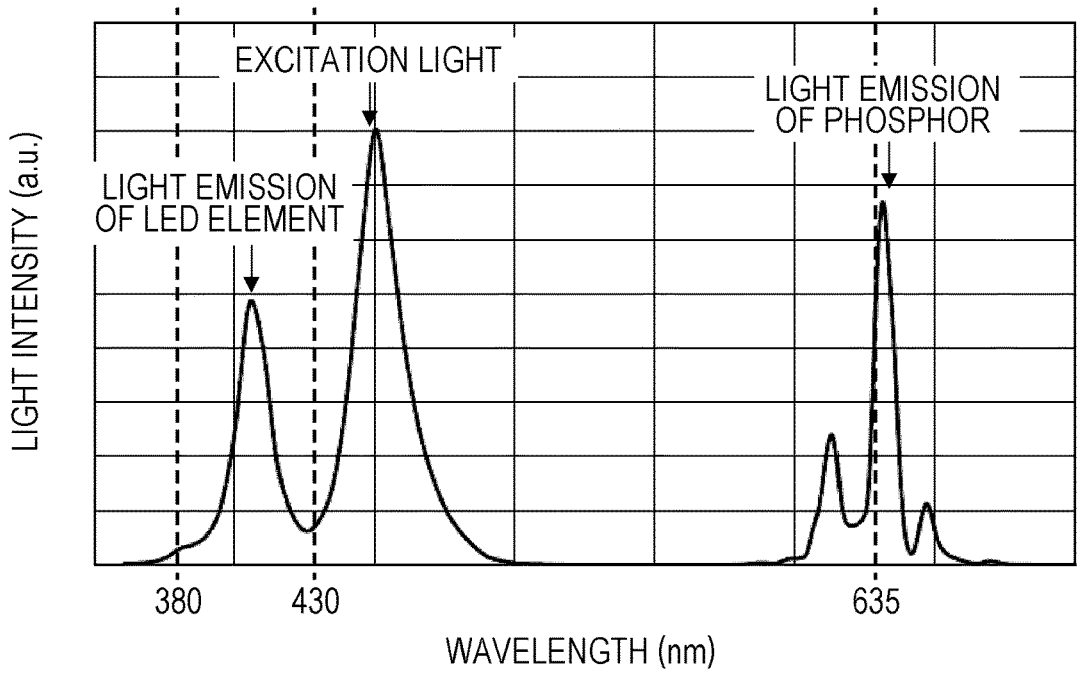
FIG. 18 is a graph illustrating a fifteenth example of the emission spectrum of the light irradiating substrate according to Embodiment 1 of the invention.
FIG. 19 is a comparison table of phosphors according to Embodiment 1 of the invention.

FIG. 18 illustrates the emission spectrum in a case where a phosphor of $K_2SiF_6:Mn$ is used.

As illustrated in FIGS. 4 to 18, each of the emission spectra includes the first wavelength region light and the second wavelength region light.

In the emission spectra illustrated in FIGS. 16 to 18, the LED chip 5 having light with the peak wavelength of 450 nm is added and light emission of the LED chip 5 exists in both of the peak wavelengths of 405 nm and 450 nm. Light with the peak wavelength of 450 nm mainly contributes to excitation of the phosphor.

Features of trials using the phosphors are indicated in FIG. 19. As each of the phosphors, a phosphor according to characteristics required for therapeutic light is able to be freely selected to customize the emission spectrum.

Note that, in order to secure flexibility of the light irradiating substrate 1 as much as possible, resin that is flexible as much as possible is desired to be used for the LED protection resin 7. This is because hard resin may cause breakage of the bonding wire 6 when the light irradiating substrate 1 is bent.

(External Connection Unit 10 and Rear Wiring 8)

The external connection unit 10 is a wiring unit by which the light irradiating substrate 1 is connected to an external power source that supplies an electric current to the light irradiating substrate 1. The external connection unit 10 supplies electrical power to the LED chips 5 from an outside via the wirings 4.

In the present embodiment, the external connection unit 10 is provided on a rear surface side of the flexible substrate 2 as illustrated in FIGS. 1 and 3. The external connection unit 10 is wired to the rear wirings 8 by solder connection or the like. The rear wirings 8 are connected to a part of the wirings 4 on the front side via the connection holes 11. The rear wirings 8 and the wirings 4 are electrically connected to each other in this manner, so that the external connection unit 10 is electrically connected to the wirings 4 via the rear wirings 8.

The external connection unit 10 includes, for example, a lead wire, a connector with which the lead wire is connected to the flexible substrate 2, and the like. Moreover, it is preferable that the external connection unit 10 is configured to be terminated with a socket, a plug, or the like for enhancing convenience of connection with the power source and to be able to be easily connected to the power source. Thus, although the lead wire is illustrated as the external connection unit 10 in FIG. 3, this is mere exemplification, and the connector or the like with which the lead wire is connected may be actually provided on the rear surface side of the flexible substrate 2.

Moreover, the external connection unit 10 includes a cathode external connection unit 10a and an anode external connection unit 10b as illustrated in FIG. 3. FIG. 3 is the schematic rear surface view illustrating the configuration of the light irradiating substrate 1 according to the present embodiment. It is preferable that each of the rear wirings 8 is covered with the connection part seal 9, which is made of insulating resin, so that the wire connection part between the external connection unit 10 and the rear wiring 8 is covered. By covering each of the rear wirings 8 (wire connection parts) with the connection part seal 9 in this manner, it is possible to insulate and isolate the rear wirings 8 from each other and secure an insulating property of the rear surface of the light irradiating substrate 1.

A spacer 21 (refer to FIG. 20) that keeps a distance to an affected part constant and fixes a positional relation between the light irradiating substrate 1 and an affected part 20 is provided on a front surface side of the light irradiating substrate 1, as described below. It is therefore difficult to provide the external connection unit 10 with respect to the wirings of the light irradiating substrate 1 on the front surface side of the light irradiating substrate 1, but it is possible to provide the external connection unit 10 on the front surface side.

(Spacer 21)

Figure 20:
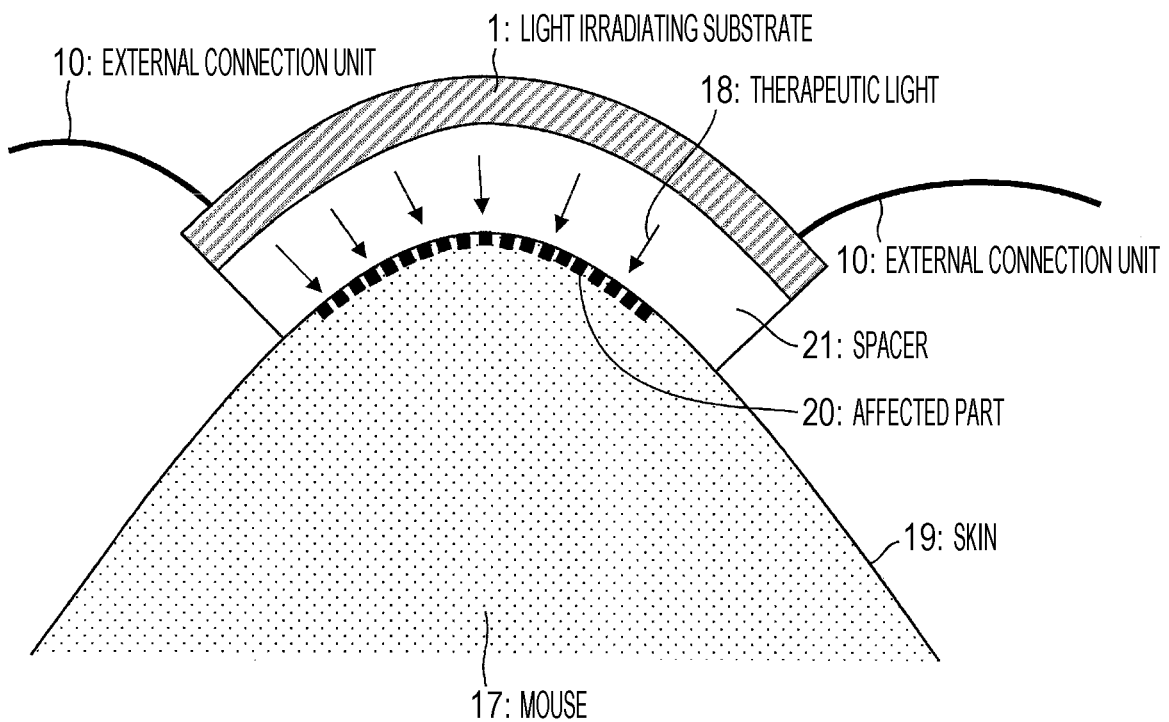
FIG. 20 is a schematic sectional view illustrating a form of a light irradiating substrate as a phototherapy machine, according to each of Embodiments 1 to 8 of the invention.

As illustrated in FIG. 20, in actual treatment, the spacer 21 is required in order to keep a distance between the front surface (specifically, front surfaces of the LED chips 5) of the light irradiating substrate 1 and the affected part 20 of a skin 19 of, for example, a mouse 17 or the like at a time of light irradiation with therapeutic light 18 and fix a positional relation between the light irradiating substrate 1 and the affected part 20, particularly, a positional relation between the LED chips 5 and the affected part 20.

As the spacer 21, various forms such as one obtained by filling a plastic bag, which is processed so as to keep a constant thickness, with water or air, an epoxy or polyurethane resin plate which is transparent and flexible, a water-absorbing polymer processed in a plate shape are able to be used.

The spacer 21 and the light irradiating substrate 1 may be integrated with each other, or may be used as different members.

The spacer 21 is able to adhere closely to the affected part 20, for example, by thinly applying white Vaseline to the affected part 20 and a periphery thereof. Similarly, for example, by thinly applying white Vaseline between the light irradiating substrate 1 and the spacer 21, it is possible to cause the light irradiating substrate 1 and the spacer 21 to adhere closely to each other.

However, for example, by bonding the spacer 21 to the front surface side of the light irradiating substrate 1 in advance, it is possible to facilitate a process of attaching the light irradiating substrate 1 to the affected part 20.

For the bonding of the spacer 21 to the light irradiating substrate 1, for example, various publicly known adhesives are able to be used.

That is, the light irradiating substrate 1 may be a light irradiating substrate with a spacer, and may further include, for example, a not-illustrated adhesive layer and the spacer 21 on the LED protection resin 7. In other words, the light irradiating substrate with a spacer according to the present embodiment may include the light irradiating substrate 1 according to FIGS. 1 to 3, the spacer 21, and the adhesive layer that bonds the light irradiating substrate 1 and the spacer 21.

It is desired that a material having rubber hardness of about 10 to 20 is used for the spacer 21. This enables bending along a curved surface such as an arm, a foot, a face, or a buttock without difficulty. The spacer 21 also has a function of reducing stress applied to the light irradiating substrate 1 when the light irradiating substrate 1 is pressed in treatment.

In order to uniformize intensity of light irradiation to the affected part 20, a relation between a thickness of the spacer 21 and pitches between the centers of the LED chips 5 (that is, the pitch Px and the pitch Py) is important.

Then, when an average value of the pitches between the adjacent LED chips 5 is D and an average thickness of the spacer 21 (to be exact, a distance from the front surface of each of the LED chips 5 to the spacer 21) is T, T/D preferably satisfies T/D≥0.5, more preferably satisfies T/D≥0.8. Generally, in a case where T/D is smaller than 0.5, a difference of intensity of light irradiation between a part immediately under the LED chip 5 and a part immediately under a middle part between the LED chips 5 is likely to be great, so that T/D is preferably set to be 0.5 or more.

Note that, in the present embodiment, for example, a resin plate obtained by molding CEP-10A which is manufactured by NISSIN RESIN Co., Ltd. and is epoxy transparent low-viscosity resin into a square of about 40 mm having a thickness of about 7 mm was used as the spacer 21, and T/D was set to be 7 mm/5 mm=1.4.

Note that, in terms of uniformity of the intensity of light irradiation, an upper limit of a value of T/D is not particularly set. However, as to facility of use at a time of actual treatment, handleability is improved as the spacer 21 is thinner. Thus, in terms of handleability, it is desired that the thickness of the spacer 21 is set so that T/D becomes, for example, 2.0 or less.

In the following embodiment, only description of D and T and a configuration in which T/D=1.4 is satisfied will be explained.

(Effect)

According to the present embodiment, it is possible to provide the light irradiating substrate 1 capable of realizing light irradiation that is suitable for treatment for a relatively small diseased part and is performed almost uniformly and efficiently even for an affected part that is not flat.

In the present embodiment, $U_1=0.75$ and $U_2=0.8$ were obtained.

Use of another substance as a photosensitizing substance is able to be derived also by similar relational expressions.

A simplest method to realize an LED that includes first wavelength region light and second wavelength region light is combining an LED element that emits the first wavelength region light and an LED element that emits the second wavelength region light. Compared with such a method, the light irradiating substrate 1 in the present embodiment has the following superiority.

(1) Since light emitted from a phosphor is propagated in all directions, there is an advantage in terms of in-plane uniformity of irradiance (mW/cm$^2$) of a first wavelength region and in-plane uniformity of irradiance of a second wavelength region in the light irradiating substrate 1.

(2) By changing a concentration of the phosphor, it is possible to freely change a ratio of intensity of light irradiation of the first wavelength region to intensity of light irradiation of the second wavelength region. This is advantageous also in terms of yield in mass production and ease of an operation. Such an advantage is difficult to be achieved by the method of simply combining two types of LED elements as described above, because an operating current needs to be controlled.

FIG. 20 is a schematic view illustrating an example in which the light irradiating substrate 1 according to the present embodiment is applied to treatment.

In the treatment using the light irradiating substrate 1, while the LED chips 5 were opposed to the affected part 20, the external connection unit 10 was connected to the external power source to perform light irradiation.

Next, an electric current of 200 mA was supplied to the light irradiating substrate 1 from the external power source via the external connection unit 10 for 8 minutes, and intensity of light irradiation was measured. Note that, although an output was slightly reduced over time, since irradiance was about 210 mW/cm$^2$ on average in each of a first short wavelength region and a second long wavelength region, supplying time (light irradiation time) was decided as 8 minutes in order to achieve a target dose of about 100 J/cm$^2$.

After repeating topical administration of "METVIXA" and the light irradiation, which are described above, five times, reduction in the number of cancer cells was confirmed. Since the cancer cells were annihilated as a whole, it is possible to presume that there is an effect of almost uniformly annihilating the cancer cells in a whole surface of the affected part 20. As a result, it was demonstrated that use of the light irradiating substrate 1 enabled performing light irradiation almost uniformly for the relatively small affected part 20 that had a curved surface and was not flat like a back of the affected part 20 as illustrated in FIG. 20.

Moreover, in terms of waste of energy when an end of the flexible substrate 2 protrudes outside the spacer 21 or prevention of light irradiation to a normal part, it is desired that the spacer 21 is formed so as to have the same size as that of the light irradiating substrate 1 or so as to be larger than the light irradiating substrate 1. However, even in a case where the spacer 21 is smaller than the light irradiating substrate 1, compared with a current phototherapy machine that irradiates an affected part with light all at once by a large lamp, a loss is far less.

According to the light irradiating substrate 1, it is possible to realize efficient and uniform light irradiation while suppressing a side effect due to the light irradiation to a minimum, so that a phototherapeutic effect with a burden of a patient and his/her family suppressed is able to be achieved. According to the light irradiating substrate 1, it is possible to provide a phototherapy machine that is able to be cut in accordance with a size of an affected part.

Note that, description as the aforementioned phototherapy machine will be omitted in the following exemplary embodiments.

Embodiment 2

Another embodiment of the invention will be described as follows with reference to FIGS. 22 to 24. Note that, in the present embodiment, description will be given for a different point from Embodiment 1, the same reference signs will be assigned to constituents having the same functions as those of the constituents described in Embodiment 1, and description thereof will be omitted.

Figure 22:
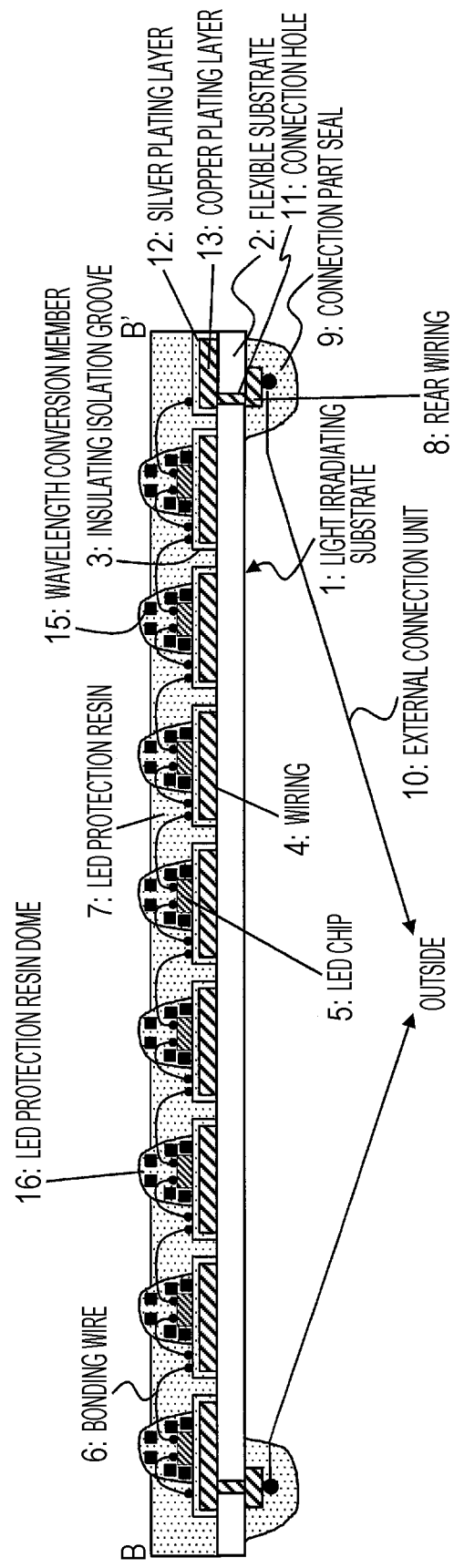
FIG. 22 is a schematic sectional view illustrating a configuration of a light irradiating substrate according to Embodiment 2 of the invention.

FIG. 22 is a schematic sectional view illustrating a configuration of the light irradiating substrate (light irradiating device) 1 according to the present embodiment. FIG. 23 is a schematic front surface view illustrating the configuration of the light irradiating substrate 1 according to the present embodiment. FIG. 24 is a schematic rear surface view illustrating the configuration of the light irradiating substrate 1 according to the present embodiment.

Figure 23:
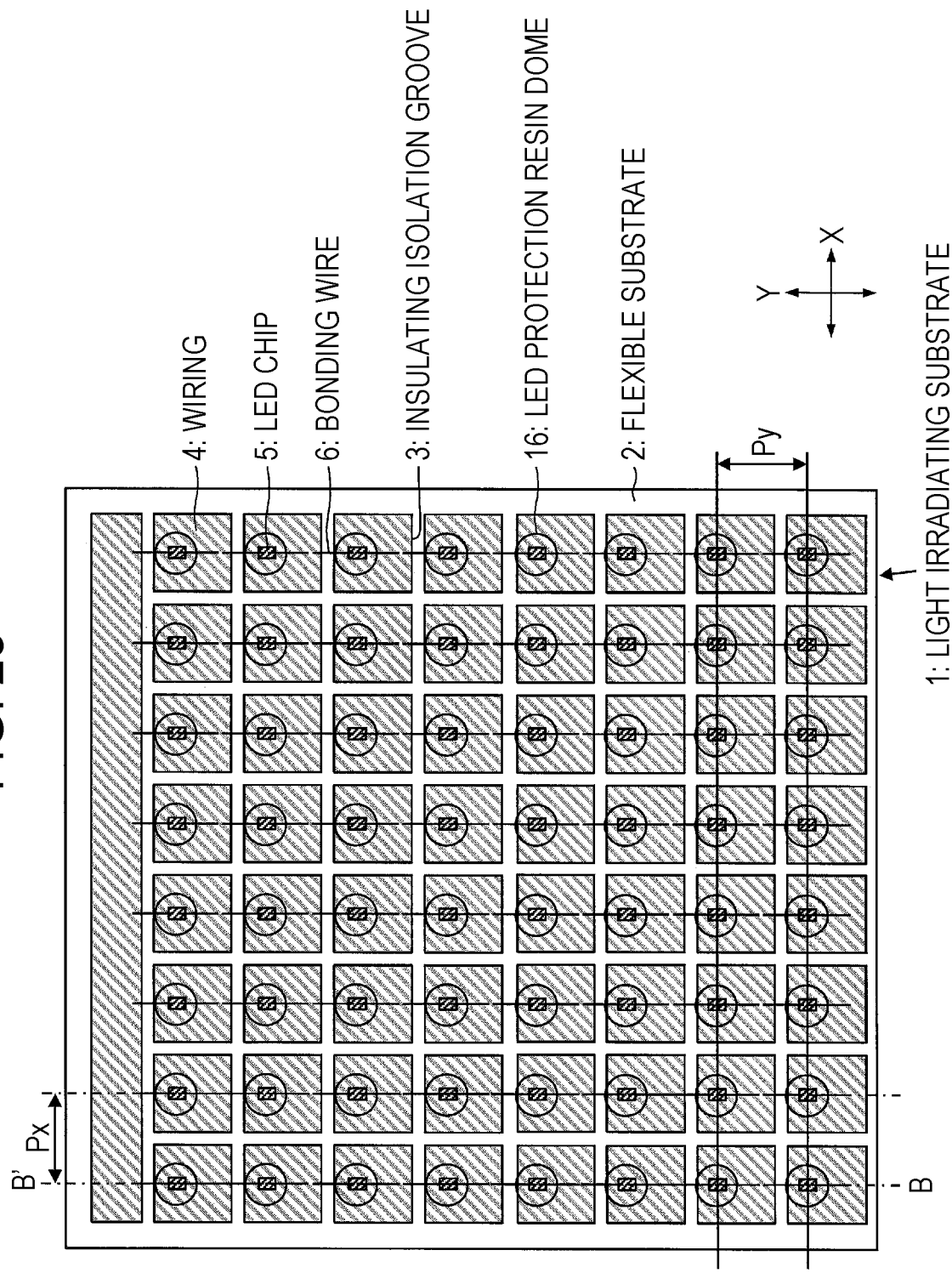
FIG. 23 is a schematic front surface view illustrating the configuration of the light irradiating substrate according to Embodiment 2 of the invention.

Note that, FIG. 22 corresponds to a sectional view taken along a line B-B' of the light irradiating substrate 1, which is illustrated in FIG. 23.

(Schematic Configuration of Light Irradiating Substrate 1)

Figure 24:
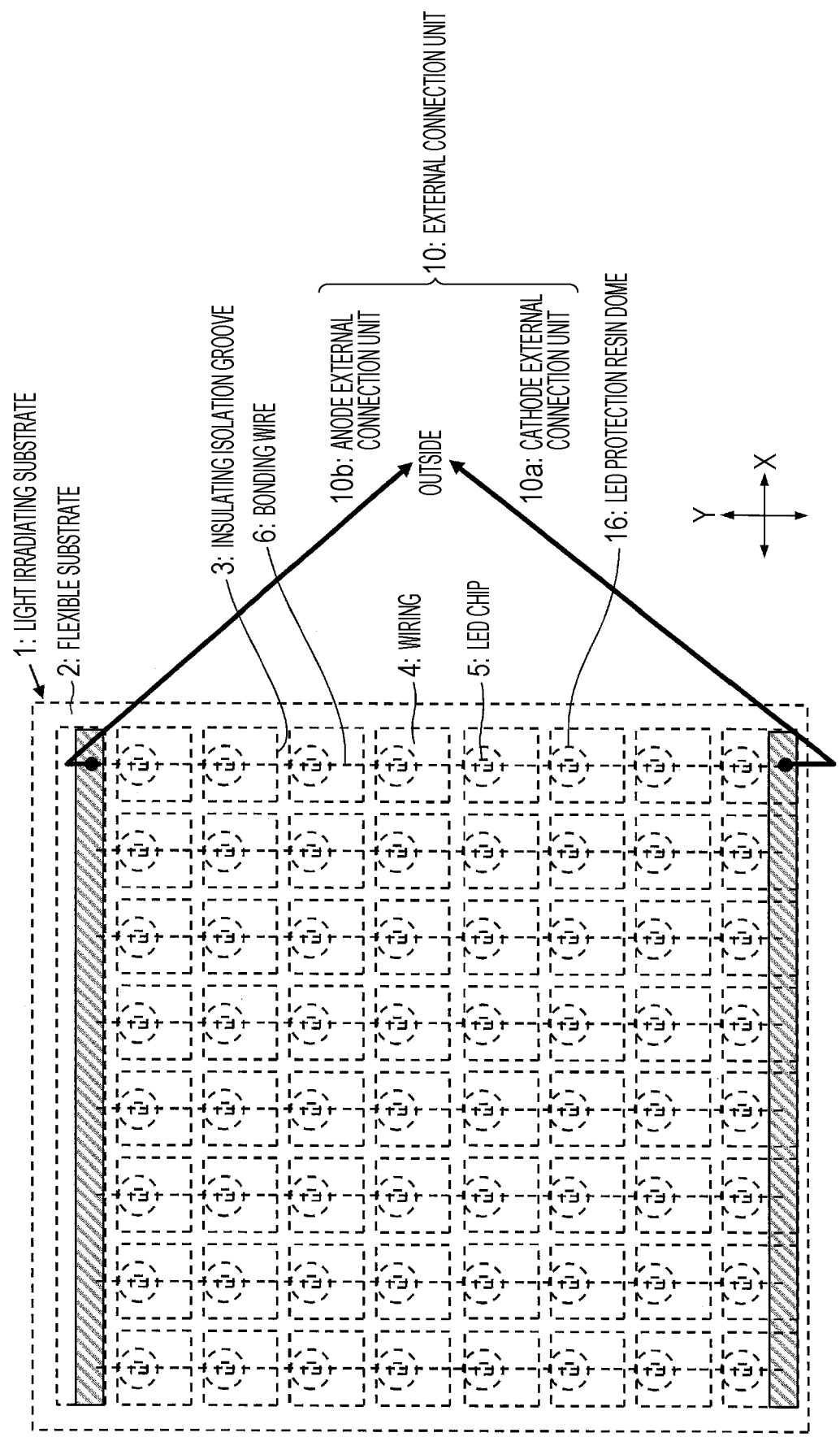
FIG. 24 is a schematic rear surface view illustrating the configuration of the light irradiating substrate according to Embodiment 2 of the invention.

As illustrated in FIGS. 22 to 24, the light irradiating substrate 1 includes the flexible substrate 2, the plurality of wirings 4 which are insulated and isolated from each other by the insulating isolation groove 3, the plurality of LED chips (LED elements) 5, the plurality of bonding wires 6, the LED protection resin 7, LED protection resin domes 16, the external connection unit 10, the rear wirings 8, the connection holes 11, the connection part seal 9, and the wavelength conversion member 15.

A difference from Embodiment 1 lies in that the LED protection resin domes 16 in which the wavelength conversion member 15 is mixed are formed as illustrated in FIGS. 22 and 23.

Each of the LED protection resin domes 16 is able to be formed by potting with the use of a dispenser, for example, but is better to be resin-molded with the use of a die in order to secure reproducibility of the shape.

By forming the LED protection resin 7 in a part that is not covered by the LED protection resin domes 16, an amount of the wavelength conversion member 15 to be used is able to be reduced and costs are able to be reduced, compared to Embodiment 1.

(Emission Spectrum)

In the present embodiment, for the LED chip 5 having the wavelength of 405 nm, the phosphor of $(Ba,Sr)MgAl_{10}O_{17}$:Eu,Mn which is the same as that of FIG. 5 of Embodiment 1 was used as the wavelength conversion member 15. A spectrum similar to that of FIG. 5 was obtained.

(Spacer 21)

In the present embodiment, a thickness T of the spacer 21 was set to be the same as that of Embodiment 1.

(Effect)

In the present embodiment, $U_1=0.74$ and $U_2=0.78$ which are almost the same as those of Embodiment 1 were obtained.

Embodiment 3

Another embodiment of the invention will be described as follows with reference to FIGS. 25 to 27. The same reference signs will be assigned to constituents having the same functions as those of the constituents described in Embodiment 1 and description thereof will be omitted.

Figure 25:
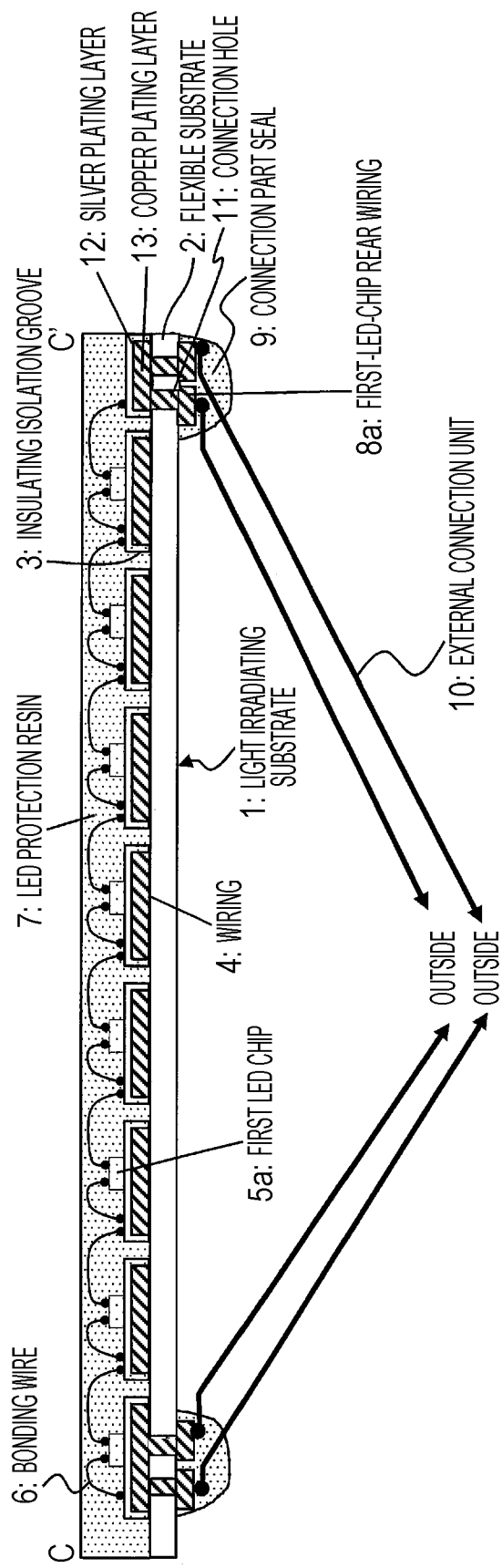
FIG. 25 is a schematic sectional view illustrating a configuration of a light irradiating substrate according to Embodiment 3 of the invention.

FIG. 25 is a schematic sectional view illustrating a configuration of the light irradiating substrate (light irradiating device) 1 according to the present embodiment. FIG. 26 is a schematic front surface view illustrating the configuration of the light irradiating substrate 1 according to the present embodiment. FIG. 27 is a schematic rear surface view illustrating the configuration of the light irradiating substrate 1 according to the present embodiment.

Figure 26:
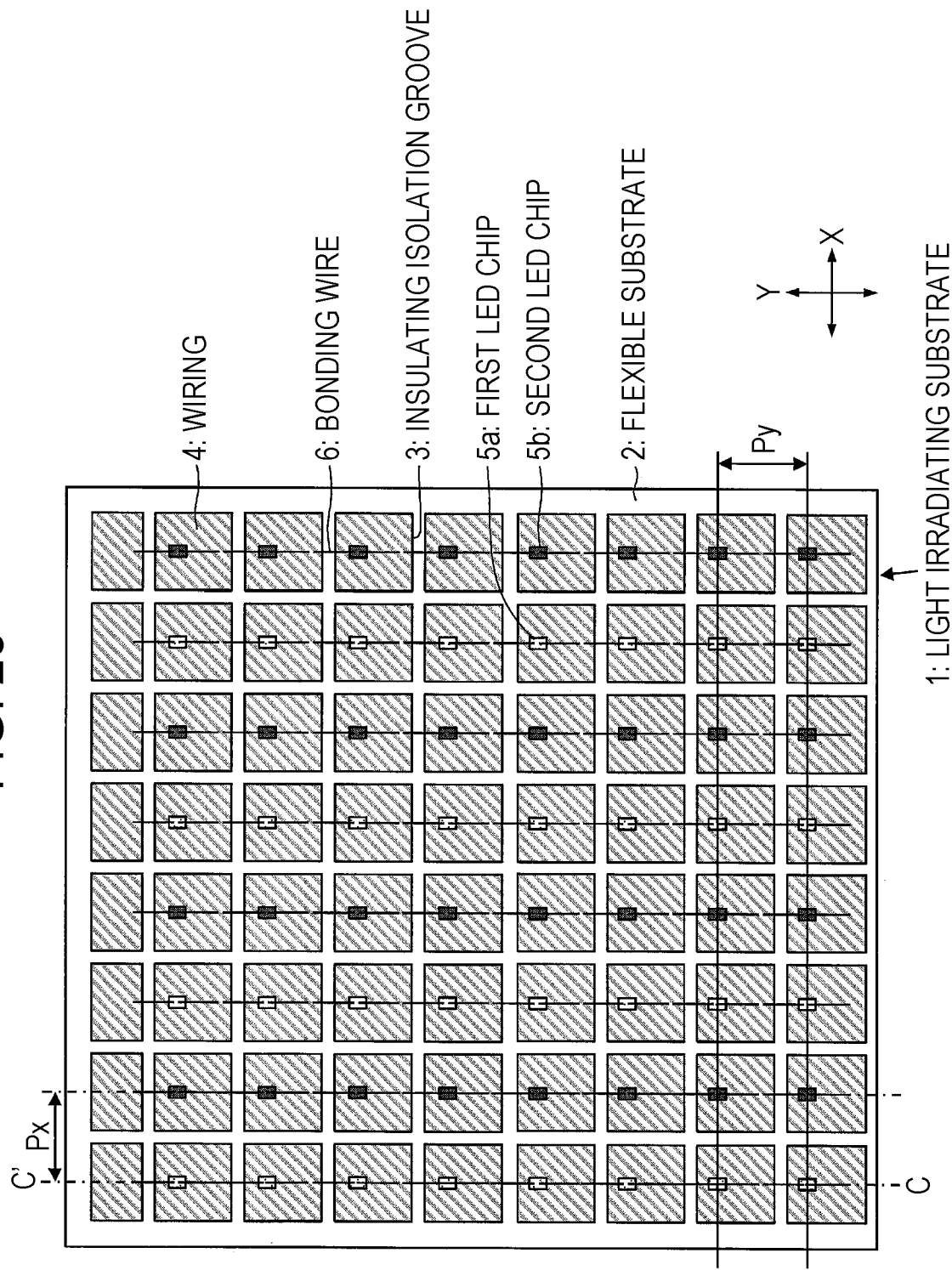
FIG. 26 is a schematic front surface view illustrating the configuration of the light irradiating substrate according to Embodiment 3 of the invention.

Note that, FIG. 25 corresponds to a sectional view taken along a line C-C' of the light irradiating substrate 1, which is illustrated in FIG. 26.

Figure 27:
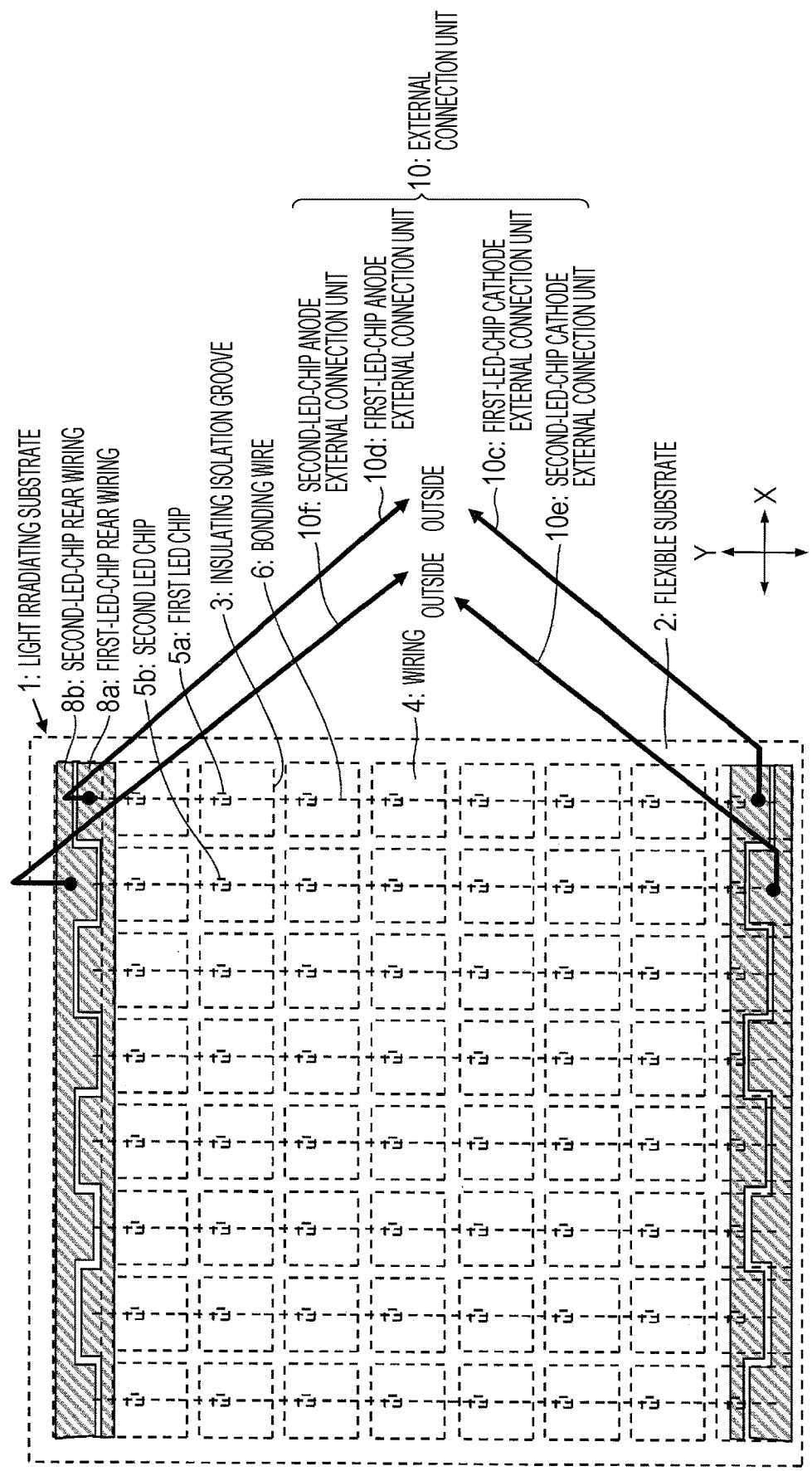
FIG. 27 is a schematic rear surface view illustrating the configuration of the light irradiating substrate according to Embodiment 3 of the invention.

As illustrated in FIGS. 25 to 27, the light irradiating substrate 1 includes the flexible substrate 2, the plurality of wirings (wiring pattern, first surface wirings) 4 which are insulated and isolated from each other by the insulating isolation groove 3, a plurality of first LED chips (LED elements) 5a, a plurality of second LED chips (LED elements) 5b, the plurality of bonding wires 6, the LED protection resin 7, the plurality of rear wirings 8, the connection part seal 9, and the external connection unit 10. A set of all the first LED chips 5a and the second LED chips 5b corresponds to the group of LED light sources according to the invention.

The wirings 4 are formed on one main surface (front surface, first surface) of the flexible substrate 2. The first LED chips 5a and the second LED chips 5b each serving as a light source are mounted on the wirings 4. The respective wirings 4 are insulated and isolated by the insulating isolation groove 3, and one first LED chip 5a or one second LED chip 5b is mounted on one wiring 4. Each of the first LED chips 5 is connected by the bonding wires 6 to a wiring 4 on which the LED chip 5 is mounted and to another wiring 4 which is adjacent to the wiring 4 in the Y direction via the insulating isolation groove 3, and the same is applied to the second LED chip 5.

In the light irradiating substrate illustrated in FIG. 26, the first LED chips 5a are arrayed in a first left column, the second LED chips 5b are arrayed in a column on a right side thereof, and the first LED chips 5a are arrayed in a column on a right side thereof in the same manner.

The first LED chips 5a, the second LED chips 5b, and the bonding wires 6 are covered with the LED protection resin 7 serving as the protective film.

On the other hand, the rear wirings 8 are formed on the other main surface (rear surface, second surface) of the flexible substrate 2.

The connection holes 11 that pass through the flexible substrate 2 are formed in the flexible substrate. The wirings 4 and first-LED-chip rear wirings 8a are connected via the connection holes 11, and the wirings 4 and second-LED-chip rear wirings 8b are connected via the connection holes 11. The wirings 4 are electrically connected to a first-LED-chip cathode external connection unit 10c and a first-LED-chip anode external connection unit 10d via the first-LED-chip rear wirings 8a. The wirings 4 are electrically connected to a second-LED-chip cathode external connection unit 10e and a second-LED-chip anode external connection unit 10f via the second-LED-chip rear wirings 8b. Wire connection parts between the external connection unit 10 and the rear wirings 8 are insulated and isolated by the connection part seal 9.

Next, constituents of the light irradiating substrate 1 will be described in more detail.

(First LED Chip 5a, Second LED Chip 5b, and Bonding Wire 6)

In the present embodiment, an LED chip having the peak wavelength of 405 nm is selected as the first LED chip 5a and an LED chip having the peak wavelength of 505 nm is selected as the second LED chip 5b.

In order to uniformly perform light irradiation for an affected part having a fixed size as in phototherapy, arranging a large number of first LED chips 5a and second LED chips 5b that are relatively small is better than using a small number of high-power (large-sized) first LED chips 5a and second LED chips 5b. In the present embodiment, 32 LED chips each of which has a size of 440 μm×550 μm are mounted on the flexible substrate 2 as the first LED chips 5a in the same manner as Embodiment 1. As the second LED chips 5b, 32 LED chips each of which has a size of 440 μm×550 μm are mounted on the flexible substrate 2.

As illustrated in FIG. 26, the first LED chips 5a and the second LED chips 5b are arranged in a two-dimensional array (two-dimensional arrangement) in which 8 pieces×8 pieces are provided along the X direction (first direction) and the Y direction (second direction) which is in the same plane as the X direction and orthogonal to the X direction. As illustrated in FIG. 26, when it is set that each pitch between the first LED chips 5a or the second LED chips 5b that are adjacent to each other in the X direction is Px and each pitch between the first LED chips 5a or the second LED chips 5b that are adjacent to each other in the Y direction which is orthogonal to the X direction is Py, the first LED chips 5a and the second LED chips 5b are arranged in a two-dimensional array at almost constant pitch (Px, Py).

In the present embodiment, an average pitch between the LED chips 5 is set to be about 5 mm to 10 mm. As the LED chips 5 having such a size, LED chips each having the most common structure in which a nitride semiconductor layer is grown epitaxially on a sapphire substrate and a cathode electrode and an anode electrode are formed on the same plane have the best light-emitting efficiency.

(External Connection Unit 10 and Rear Wiring 8)

In general, operating voltages of the first LED chips 5a and the second LED chips 5b are not always the same. As illustrated in FIG. 27, in a case where a voltage to drive eight first LED chips 5a and a voltage to drive eight second LED chips 5b are different, the first-LED-chip rear wirings 8a and the second-LED-chip rear wirings 8b are required.

As illustrated in FIG. 27, the external connection unit 10 includes the first-LED-chip cathode external connection unit 10c, the first-LED-chip anode external connection unit 10d, the second-LED-chip cathode external connection unit 10e, and the second-LED-chip anode external connection unit 10f. FIG. 27 is the schematic rear surface view illustrating the configuration of the light irradiating substrate 1 according to the present embodiment. It is preferable that each of the rear wirings 8 is covered with the connection part seal 9, which is formed of insulating resin, so that the wire connection parts between the external connection unit 10 and the rear wirings 8 are covered. In this manner, by covering each of the rear wirings 8 (wire connection parts) with the connection part seal 9, the rear wirings 8 are able to be insulated and isolated from each other and an insulating property of the rear surface of the light irradiating substrate 1 is able to be secured.

(Emission Spectrum)

Figure 28:
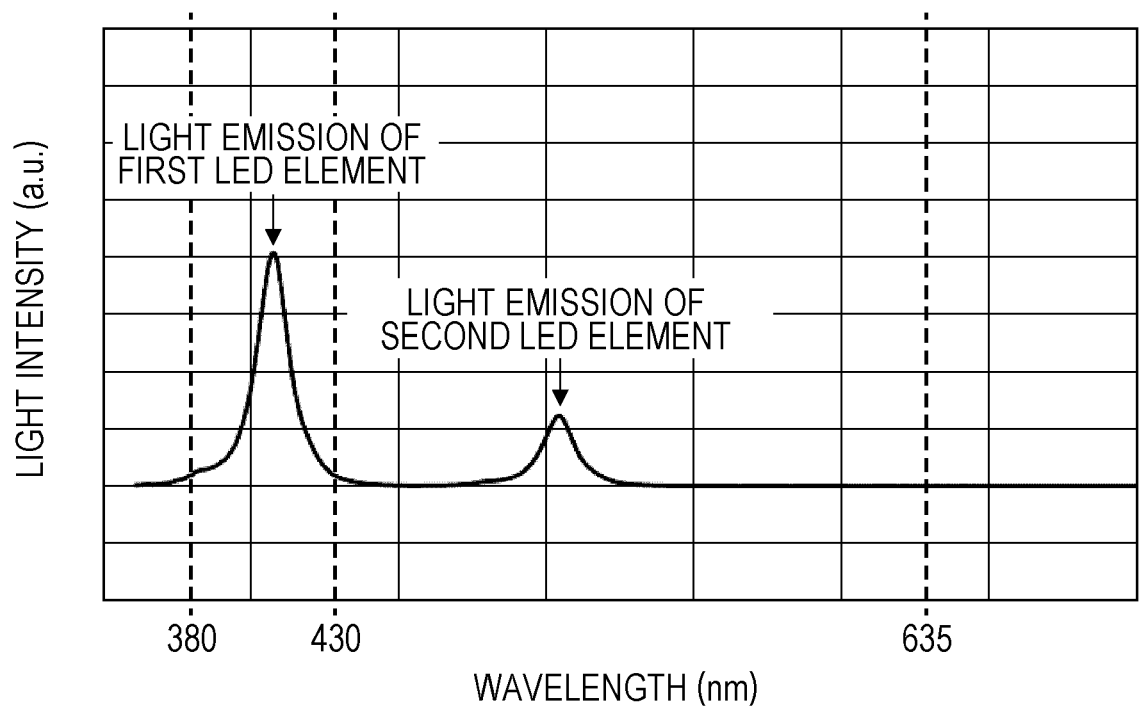
FIG. 28 is a graph illustrating an example of an emission spectrum of the light irradiating substrate according to Embodiment 3 of the invention.

As illustrated in FIG. 28, light emission from the first LED chips 5a was observed when the wavelength was 405 nm and light emission from the second LED chips 5b was observed when the wavelength was 505 nm. Flexible LEDs that have both of the first wavelength region light and the second wavelength region light were achieved as intended.
(Spacer 21)

In the present embodiment, an average pitch D between the LED chips is a repetitive cycle of the first LED chips 5a and the second LED chips 5b and is twice that of Embodiment 1. Thus, the thickness T of the spacer 21 was set to be twice that of Embodiment 1.
(Effect)

In the present embodiment, $U_1$=0.71 and $U_2$=0.72 were obtained.

Embodiment 4

Another embodiment of the invention will be described as follows with reference to FIGS. 29 to 31. In the present embodiment, a difference from Embodiment 3 will be mainly described, the same reference signs will be assigned to constituents having the same functions as those of the constituents described in Embodiment 3, and description thereof will be omitted.

Figure 29:
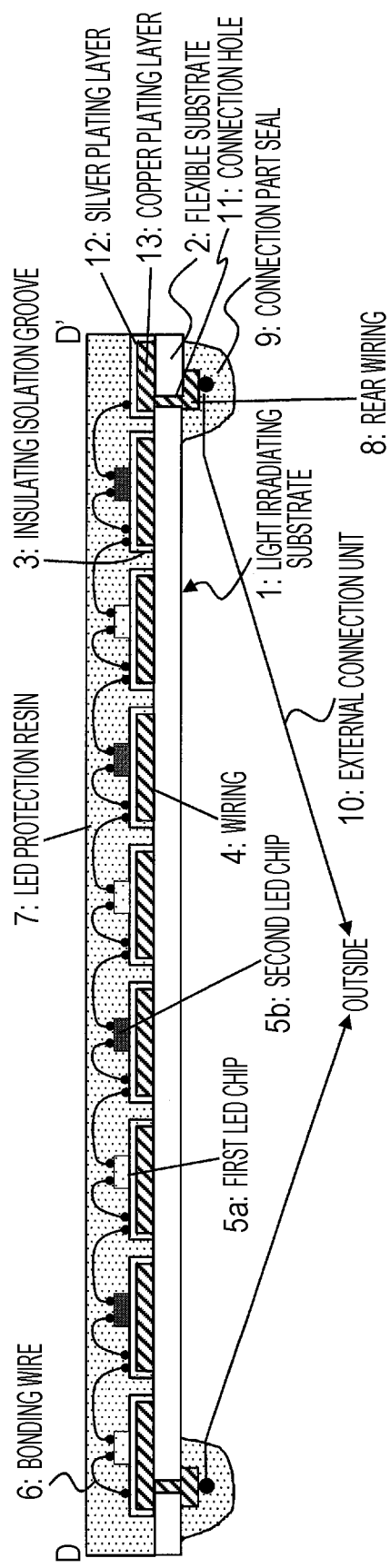
FIG. 29 is a schematic sectional view illustrating a configuration of a light irradiating substrate according to Embodiment 4 of the invention.

FIG. 29 is a schematic sectional view illustrating a configuration of the light irradiating substrate (light irradiating device) 1 according to the present embodiment. FIG. 30 is a schematic front surface view illustrating the configuration of the light irradiating substrate 1 according to the present embodiment. FIG. 31 is a schematic rear surface view illustrating the configuration of the light irradiating substrate 1 according to the present embodiment.

Figure 30:
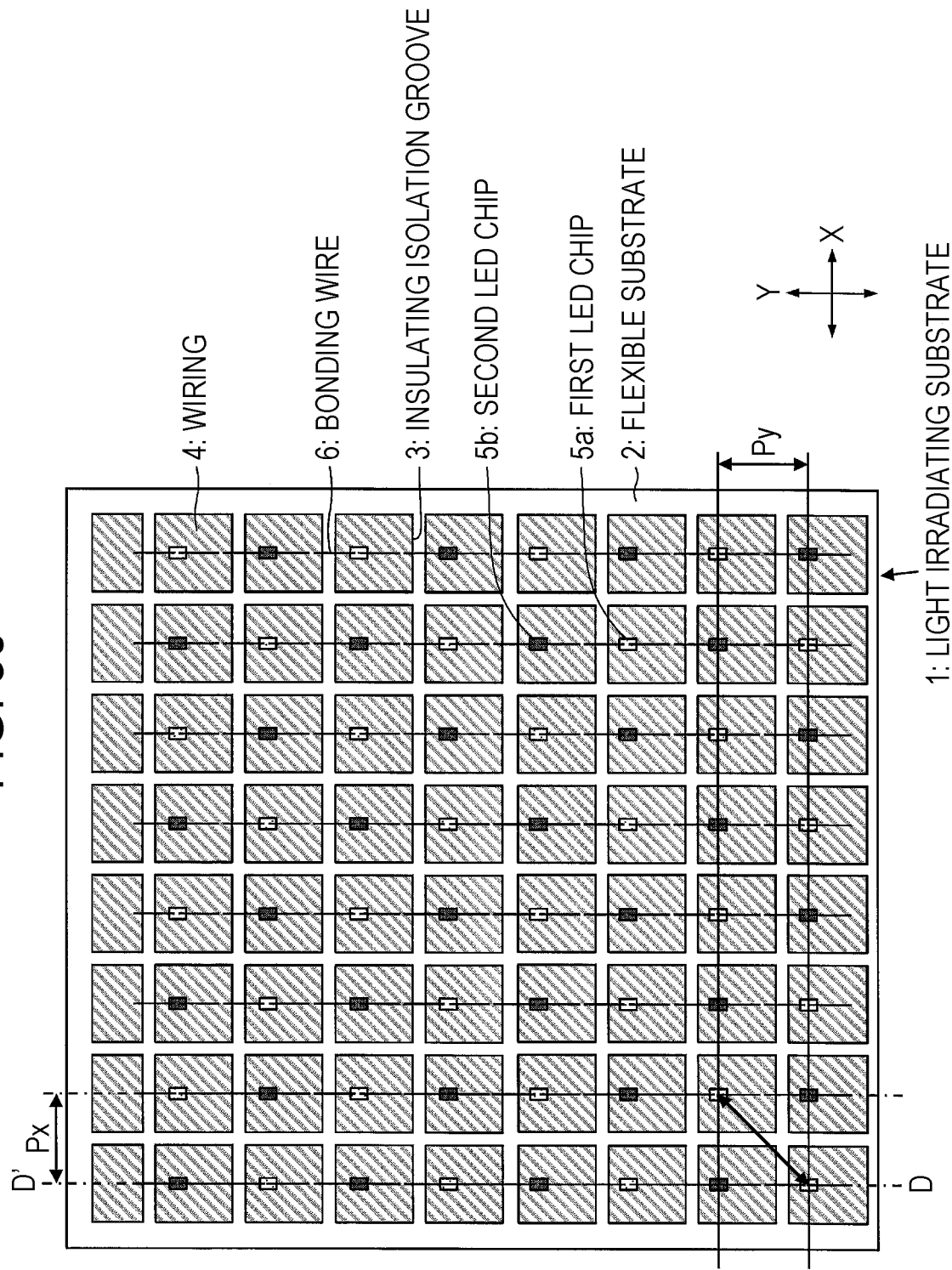
FIG. 30 is a schematic front surface view illustrating the configuration of the light irradiating substrate according to Embodiment 4 of the invention.
Figure 31:
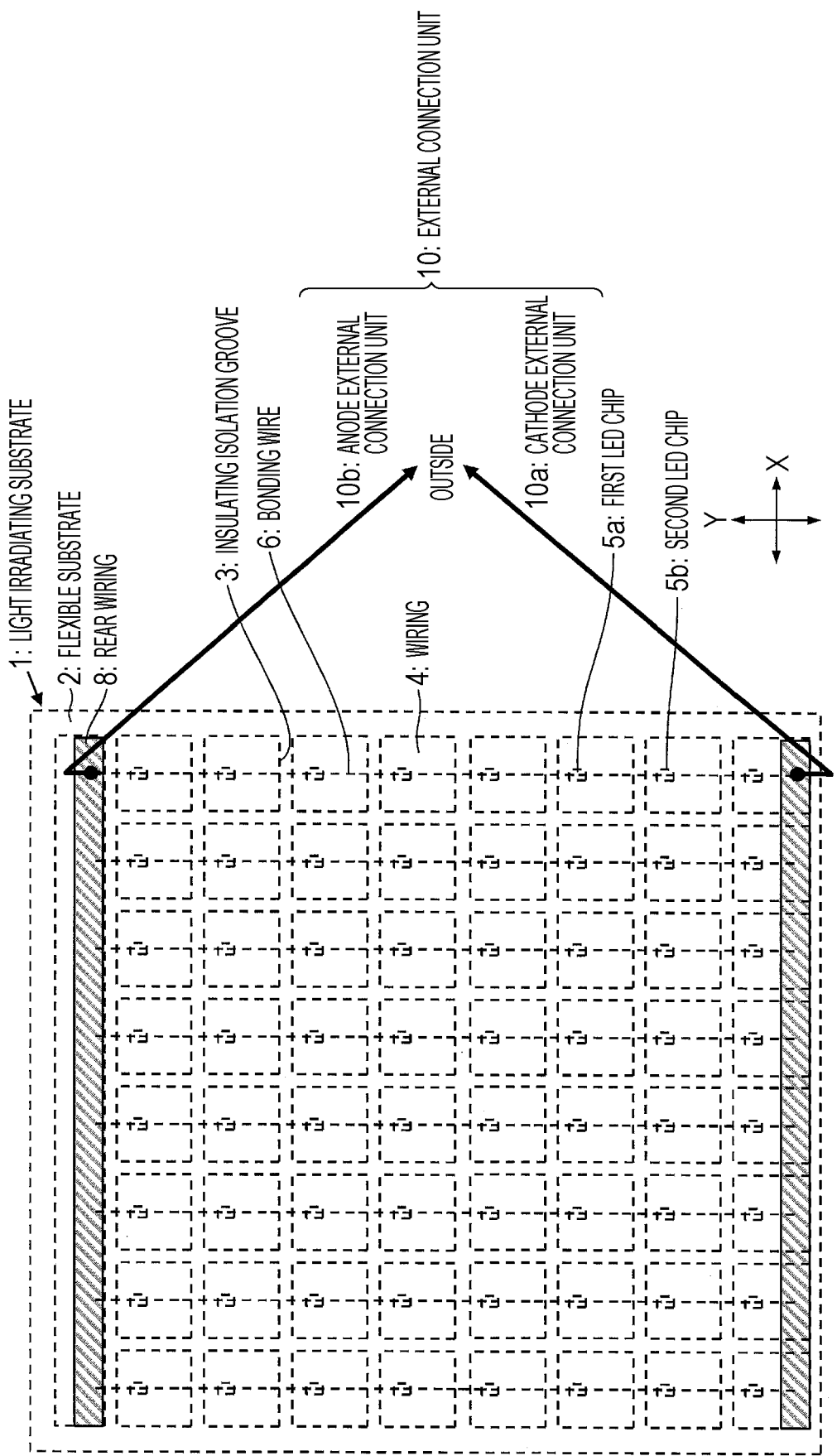
FIG. 31 is a schematic rear surface view illustrating the configuration of the light irradiating substrate according to Embodiment 4 of the invention.

Note that, FIG. 29 corresponds to a sectional view taken along a line D-D' of the light irradiating substrate 1, which is illustrated in FIG. 30.

The wirings 4 are formed on one main surface (front surface, first surface) of the flexible substrate 2. The first LED chips 5a and the second LED chips 5b each serving as a light source are mounted on the wirings 4. The respective wirings 4 are insulated and isolated by the insulating isolation groove 3, and one first LED chip 5a or one second LED chip 5b is mounted on one wiring 4. Each of the first LED chips 5a is connected by the bonding wires 6 to a wiring 4 on which the first LED chip 5a is mounted and to another wiring 4 which is adjacent to the wiring 4 in the Y direction via the insulating isolation groove 3. Each of the second LED chips 5b is connected by the bonding wires 6 to a wiring 4 on which the second LED chip 5b is mounted and to another wiring 4 which is adjacent to the wiring 4 in the Y direction via the insulating isolation groove 3.
(First LED Chip 5a and Second LED Chip 5b)

As illustrated in FIGS. 29 and 30, on the light irradiating substrate 1 according to the present embodiment, four first LED chips 5a and four second LED chips 5b are alternately arranged in a line in the Y direction (second direction), four first LED chips 5a and four second LED chips 5b are alternately arranged in a line on a right side thereof in inverse order, four first LED chips 5a and four second LED chips 5b are alternately arranged in a line in the Y direction on a right side thereof in inverse order, and four first LED chips 5a and four second LED chips 5b are alternately arranged in a line in the Y direction on a right side thereof in inverse order (two-dimensional arrangement). That is, a chip adjacent to the first LED chip 5a is the second LED chip 5b and a chip adjacent to the second LED chip 5b is the first LED chip 5a.

On the other hand, the rear wirings 8 are formed on the other main surface (rear surface, second surface) of the flexible substrate 2.

The connection holes 11 that pass through the flexible substrate 2 are formed in the flexible substrate. The wirings 4 and the rear wirings 8 are connected via the connection holes 11. The wirings 4 are electrically connected to the external connection unit 10 via the rear wirings 8. Wire connection parts between the external connection unit 10 and the rear wirings 8 are insulated and isolated by the connection part seal 9.

Next, each constituent of the light irradiating substrate 1 will be described in more detail.

In the present embodiment, as illustrated in FIG. 30, 32 LED chips each of which has a size of 440 μm×550 μm are mounted on the flexible substrate 2 as the first LED chips 5a in the same manner as Embodiment 1. As the second LED chips 5b, 32 LED chips each of which has a size of 440 μm×550 μm are mounted on the flexible substrate 2.

As illustrated in FIG. 30, the first LED chips 5a and the second LED chips 5b are arranged in a two-dimensional array (two-dimensional arrangement) in which 8 pieces×8 pieces are provided along the X direction (first direction) and the Y direction (second direction) which is in the same plane as the X direction and orthogonal to the X direction. As illustrated in FIG. 30, when it is set that each pitch between the first LED chip 5a and the second LED chip 5b that are adjacent to each other in the X direction is Px and each pitch between the first LED chip 5a and the second LED chip 5b that are adjacent to each other in the Y direction which is orthogonal to the X direction is Py, the first LED chips 5a and the second LED chips 5b are arranged in a two-dimensional array at almost constant pitch (Px, Py).
(External Connection Unit 10 and Rear Wiring 8)

Differently from Embodiment 3, four first LED chips 5a and four second LED chips 5b are connected in series in each of the columns, so that operating voltages in the respective columns are almost the same. As illustrated in FIG. 31, differently from Embodiment 3, the rear wirings are made into one system in the same manner as Embodiment 1.
(Emission Spectrum)

As illustrated in FIG. 28, similarly to Embodiment 3, light emission from the first LED chips 5a was observed when the wavelength was 405 nm and light emission from the second LED chips 5b was observed when the wavelength was 505 nm. LEDs that have both of the first wavelength region light and the second wavelength region light were achieved as intended.
(Spacer 21)

In the present embodiment, the average pitch D between the LED chips is a repetitive cycle of the first LED chips 5a and the second LED chips 5b and is $\sqrt{2}/2$ times that of Embodiment 3. Accordingly, the thickness T of the spacer 21 was reduced so as to be $\sqrt{2}/2$ times that of Embodiment 1.
(Effect)

In the present embodiment, $U_1$=0.74 and $U_2$=0.75 were obtained.

Embodiment 5

Another embodiment of the invention will be described as follows with reference to FIG. 32. In the present embodiment, a difference from Embodiment 4 will be mainly described, the same reference signs will be assigned to constituents having the same functions as those of the constituents described in Embodiment 4, and description thereof will be omitted.

Figure 32:
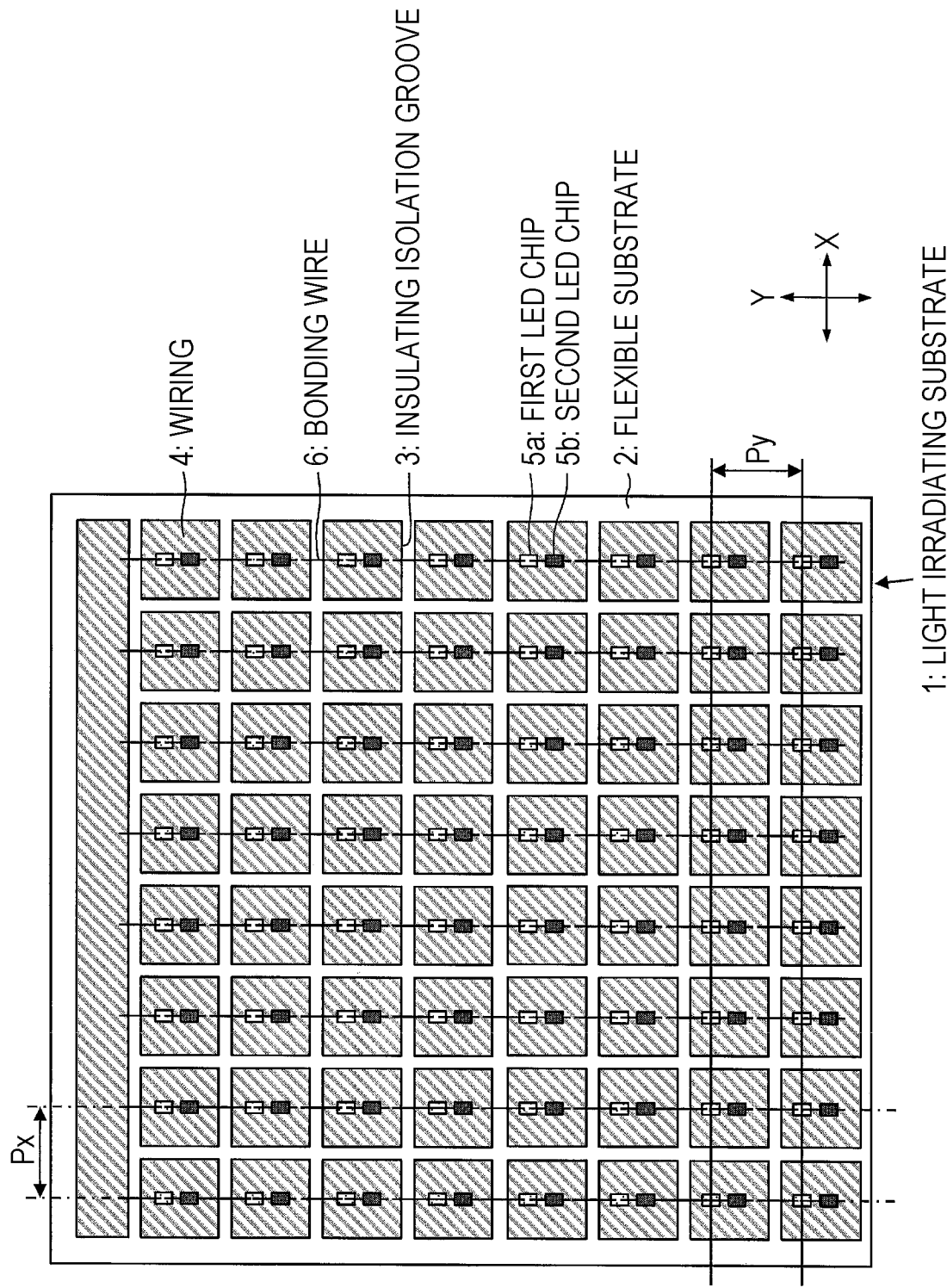
FIG. 32 is a schematic front surface view illustrating a configuration of a light irradiating substrate according to Embodiment 5 of the invention.

FIG. 32 is a schematic front surface view illustrating a configuration of the light irradiating substrate (light irradiating device) 1 according to the present embodiment.

The wirings 4 are formed on one main surface (front surface, first surface) of the flexible substrate 2. The first LED chips 5a and the second LED chips 5b each serving as a light source are mounted on the wirings 4. The respective wirings 4 are insulated and isolated by the insulating isolation groove 3, and one first LED chip 5a and one second LED chip 5b are mounted on one wiring 4. Each of the first LED chips 5a is connected by the bonding wires 6 to a second LED chip 5b and to a wiring 4 which is adjacent to a wiring 4, on which the first LED chip 5a is mounted, in the Y direction via the insulating isolation groove 3. Each of the second LED chips 5b is connected by the bonding wires 6 to a wiring 4 on which the second LED chip 5b is mounted and a first LED chip 5a.

(First LED Chip 5a and Second LED Chip 5b)

As illustrated in FIG. 32, in the light irradiating substrate 1 according to the present embodiment, one first LED chip 5a and one second LED chip 5b are set as one unit and units are arranged in eight rows in the X direction and eight columns in the Y direction (two-dimensional arrangement).

Next, each constituent of the light irradiating substrate 1 will be described in more detail.

As illustrated in FIG. 32, when it is set that each pitch between the first LED chips 5a in the X direction is Px and each pitch between the first LED chips 5a in the Y direction which is orthogonal to the X direction is Py, one first LED chip 5a and one second LED chip 5b are arranged as one unit in a two-dimensional array at almost constant pitch (Px, Py).

(Emission Spectrum)

As illustrated in FIG. 28, similarly to Embodiment 4, light emission from the first LED chips 5a was observed when the wavelength was 405 nm and light emission from the second LED chips 5b was observed when the wavelength was 505 nm. LEDs that have both of the first wavelength region light and the second wavelength region light were achieved as intended.

(Spacer 21)

In the present embodiment, the average pitch D between the LED chips is a repetitive cycle of the first LED chips 5a and the second LED chips 5b and is 2/√2 times that of Embodiment 4. Accordingly, compared to Embodiment 4, the thickness T of the spacer 21 was set to be the same as that of Embodiment 1.

(Effect)

In the present embodiment, $U_1$=0.75 and $U_2$=0.74 were obtained.

Embodiment 6

Another embodiment of the invention will be described as follows with reference to FIG. 33. In the present embodiment, a difference from Embodiment 5 will be mainly described, the same reference signs will be assigned to constituents having the same functions as those of the constituents described in Embodiment 5, and description thereof will be omitted.

Figure 33:
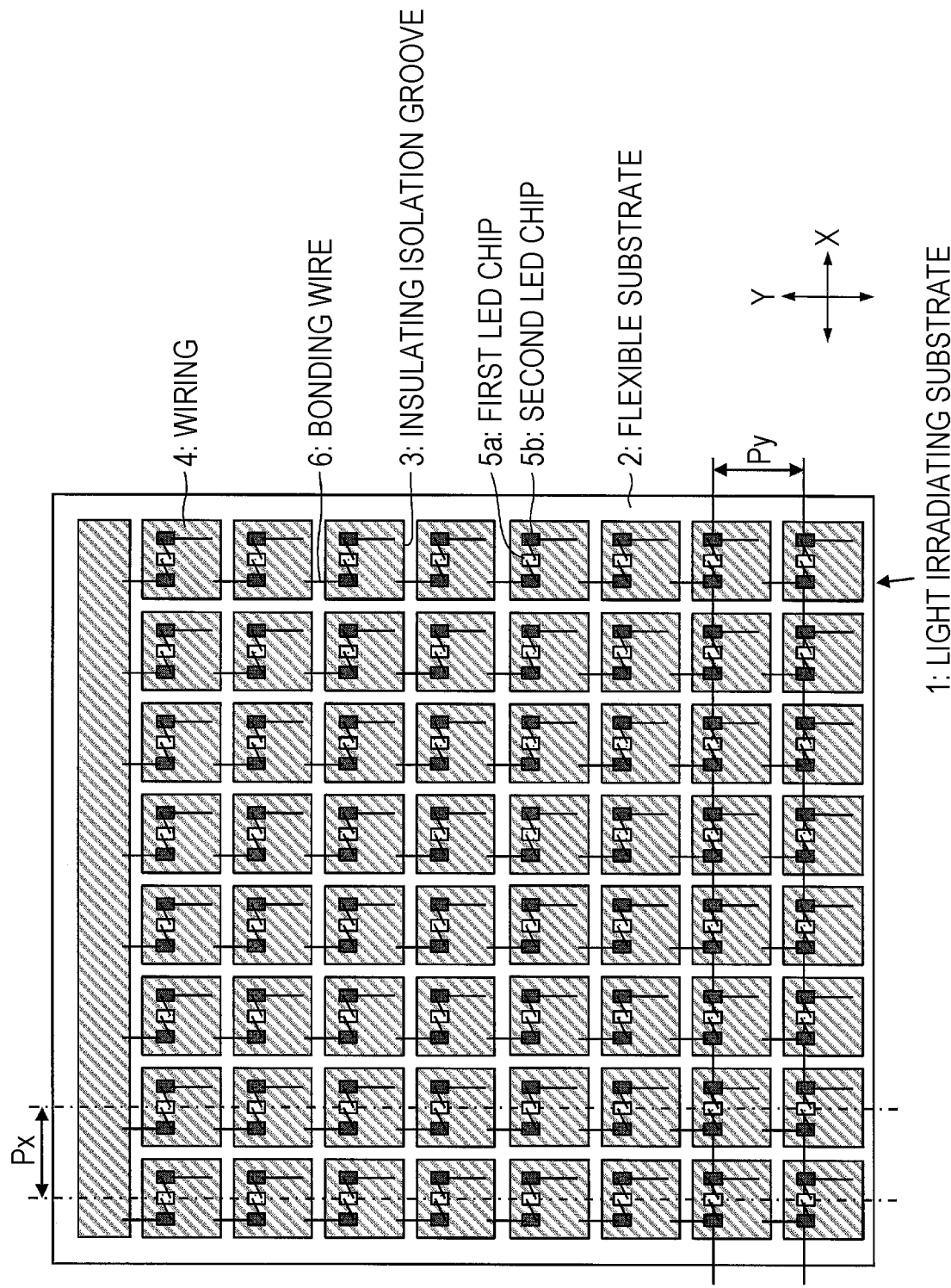
FIG. 33 is a schematic front surface view illustrating a configuration of a light irradiating substrate according to Embodiment 6 of the invention.

FIG. 33 is a schematic front surface view illustrating a configuration of the light irradiating substrate (light irradiating device) 1 according to the present embodiment.

Generally, in a case where the peak wavelength of the second LED chip 5b is 470 nm or more, light intensity of the second LED chip 5b is weak as compared to that of the first LED chip 5a at the same operating voltage. In this case, for example, two second LED chips 5b need to be mounted. However, since the second LED chip 5b absorbs light emitted from the first LED chip 5a, it is desired that the first LED chip 5a and the second LED chip 5b are arranged as far apart as possible. In order to almost uniformly radiate the first wavelength region light and the second wavelength region light, it is necessary to arrange one first LED chip 5a and two second LED chips 5b as one unit. Specifically, it is important that center of gravity of two second LED chips 5b matches a position of one first LED chip 5a.

The wirings 4 are formed on one main surface (front surface, first surface) of the flexible substrate 2. The first LED chips 5a and the second LED chips 5b each serving as a light source are mounted on the wirings 4. The respective wirings 4 are insulated and isolated by the insulating isolation groove 3, and one first LED chip 5a and two second LED chips 5b are mounted on one wiring 4. A wiring 4, a second LED chip 5b, a first LED chip 5a, a second LED chip 5b, and another wiring 4 which is adjacent to the wiring 4 in the Y direction via the insulating isolation groove 3 are connected by a bonding wire 6.

(First LED Chip 5a and Second LED Chip 5b)

As illustrated in FIG. 33, in the light irradiating substrate 1 according to the present embodiment, one first LED chip 5a and two second LED chips 5b are set as one unit and units are arranged in eight rows in the X direction and eight columns in the Y direction (second direction) (two-dimensional arrangement).

Next, each constituent of the light irradiating substrate 1 will be described in more detail.

As illustrated in FIG. 33, when it is set that each pitch between the first LED chips 5a in the X direction is Px and each pitch between the first LED chips 5a in the Y direction which is orthogonal to the X direction is Py, one first LED chip 5a and two second LED chips 5b are arranged as one unit in a two-dimensional array at almost constant pitch (Px, Py).

(Emission Spectrum)

Figure 34:
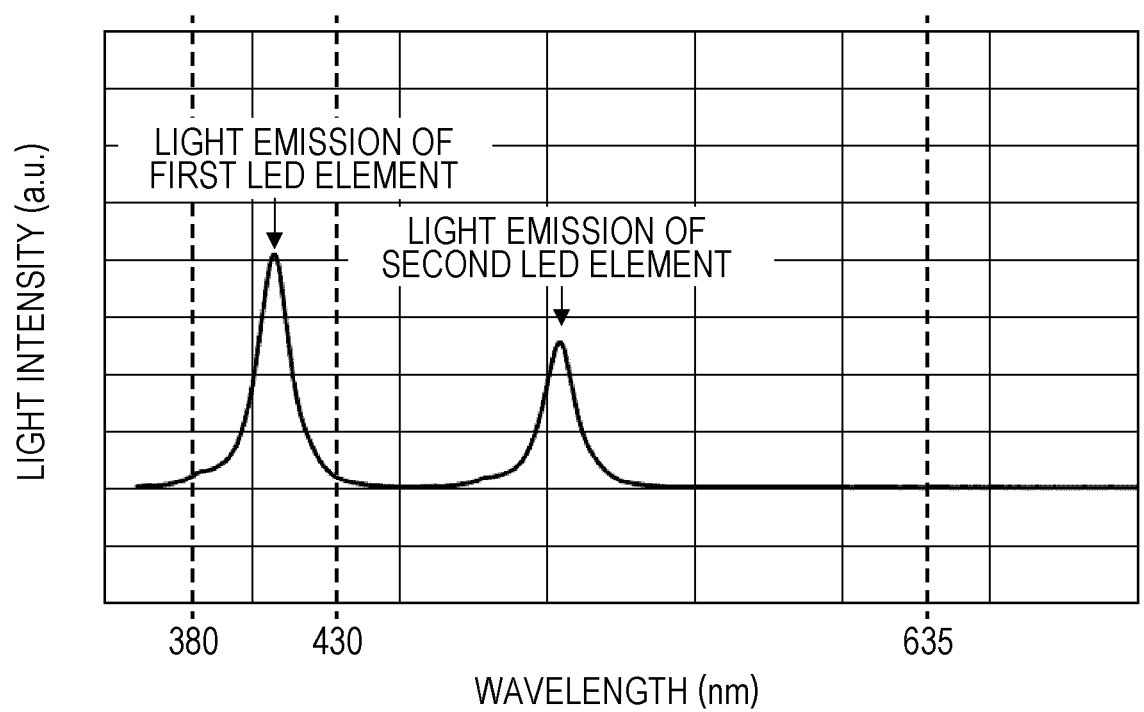
FIG. 34 is a graph illustrating an example of an emission spectrum of the light irradiating substrate according to Embodiment 6 of the invention.

As illustrated in FIG. 34, similarly to Embodiment 5, light emission from the first LED chips 5a was observed when the wavelength was 405 nm and light emission from the second LED chips 5b was observed when the wavelength was 505 nm. In addition, peak intensity of second wavelength region light increases as intended. An effect by arranging two second LED chips 5b was confirmed. LEDs that have both of the first wavelength region light and the second wavelength region light were achieved.

(Spacer 21)

In the present embodiment, the average pitch D between the LED chips is a repetitive cycle of one first LED chip 5a and two second LED chips 5b and is the same as that of Embodiment 5. Accordingly, the thickness T of the spacer 21 was set to be the same as that of Embodiment 5.

(Effect)

In the present embodiment, $U_1$=0.74 and $U_2$=0.73 were obtained.

Though an example in which two second LED chips 5b are mounted has been described in the present embodiment, more than two second LED chips 5b may be arranged. In this case, spatial arrangement is able to be devised on the basis of similar technical ideas.

According to the light irradiating substrate 1, it is possible to realize efficient and uniform light irradiation while suppressing a side effect due to the light irradiation to a minimum, so that a phototherapeutic effect with a burden of a patient and his/her family suppressed is able to be achieved. According to the light irradiating substrate 1, it is possible to provide a phototherapy machine capable of being cut in accordance with a size of an affected part.

Embodiment 7

Another embodiment of the invention will be described as follows with reference to FIG. 35. In the present embodiment, a difference from Embodiment 6 will be mainly described, the same reference signs will be assigned to constituents having the same functions as those of the constituents described in Embodiment 6, and description thereof will be omitted.

Figure 35:
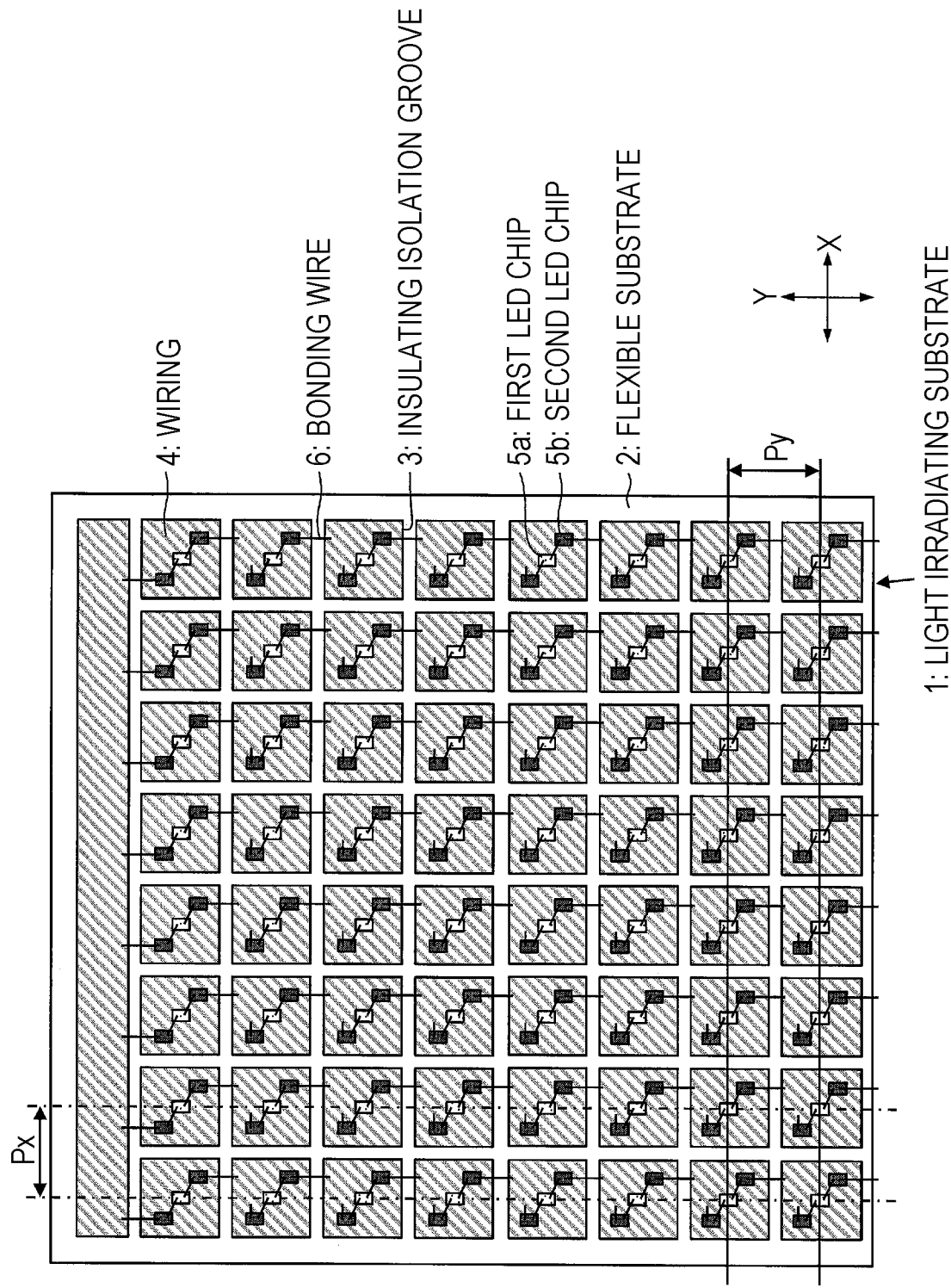
FIG. 35 is a schematic front surface view illustrating a configuration of a light irradiating substrate according to Embodiment 7 of the invention.

FIG. 35 is a schematic front surface view illustrating a configuration of the light irradiating substrate (light irradiating device) 1 according to the present embodiment.

Generally, in a case where each of the first LED chips 5a and each of the second LED chips 5b are in rectangular shapes in top view as illustrated in FIG. 35, light is output from four sides of a chip of each of the first LED chip 5a and the second LED chip 5b. The second LED chip 5b absorbs light emitted from the first LED chip 5a. In order to suppress such a phenomenon, one first LED chip 5a and two second LED chips 5b are shifted not only in the X direction but also in the Y direction. In other words, arrangement is performed so that each side of the rectangular shape of each of the two second LED chips 5b and each side of the rectangular shape of the first LED chip 5a do not face each other in each of the wirings 4. This makes it possible to further reduce the absorption. In order to almost uniformly radiate the first wavelength region light and the second wavelength region light in the same manner as Embodiment 6, it is necessary to arrange one first LED chip 5a and two second LED chips 5b as one unit. Specifically, center of gravity of two second LED chips 5b is caused to match a position of one first LED chip 5a.

As illustrated in FIG. 35, in the light irradiating substrate 1 according to the present embodiment, one first LED chip 5a and two second LED chips 5b are set as one unit and units are arranged in eight rows in the X direction and eight columns in the Y direction (second direction) (two-dimensional arrangement).

Next, each constituent of the light irradiating substrate 1 will be described in more detail.

As illustrated in FIG. 35, when it is set that each pitch between the first LED chips 5a in the X direction is Px and each pitch between the first LED chips 5a in the Y direction which is orthogonal to the X direction is Py, one first LED chip 5a and two second LED chips 5b are arranged as one unit in a two-dimensional array at almost constant pitch (Px, Py).

(Emission Spectrum)

Figure 36:
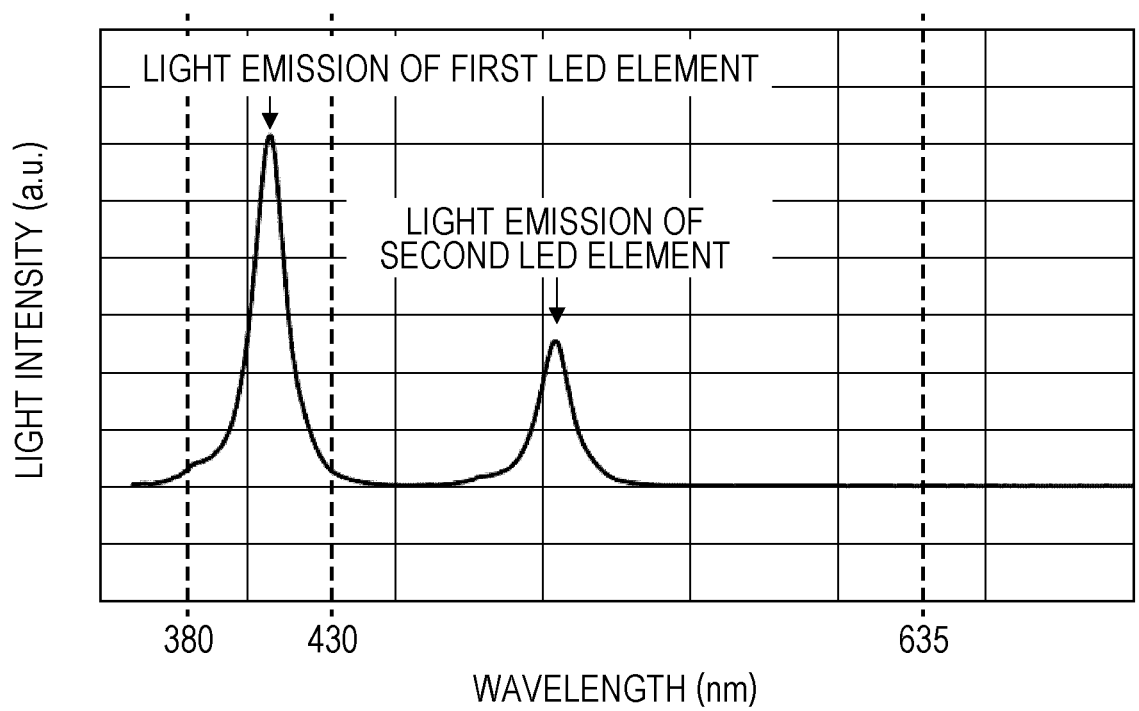
FIG. 36 is a graph illustrating an example of an emission spectrum of the light irradiating substrate according to Embodiment 7 of the invention.

As illustrated in FIG. 36, similarly to Embodiment 6, light emission from the first LED chips 5a was observed when the wavelength was 405 nm and light emission from the second LED chips 5b was observed when the wavelength was 505 nm. In addition, peak intensity of the first wavelength region light increases as intended. An effect by reduction in the light emitted from the first LED chip 5a to be absorbed by the second LED chips 5b was confirmed. LEDs that have both of the first wavelength region light and the second wavelength region light were achieved.

(Spacer 21)

In the present embodiment, the average pitch D between the LED chips is a repetitive cycle of one first LED chip 5a and two second LED chips 5b and is the same as that of Embodiment 7. Accordingly, the thickness T of the spacer 21 was set to be the same as that of Embodiment 7.

(Effect)

In the present embodiment, $U_1=0.8$ and $U_2=0.73$ were obtained.

Embodiment 8

Figure 37:
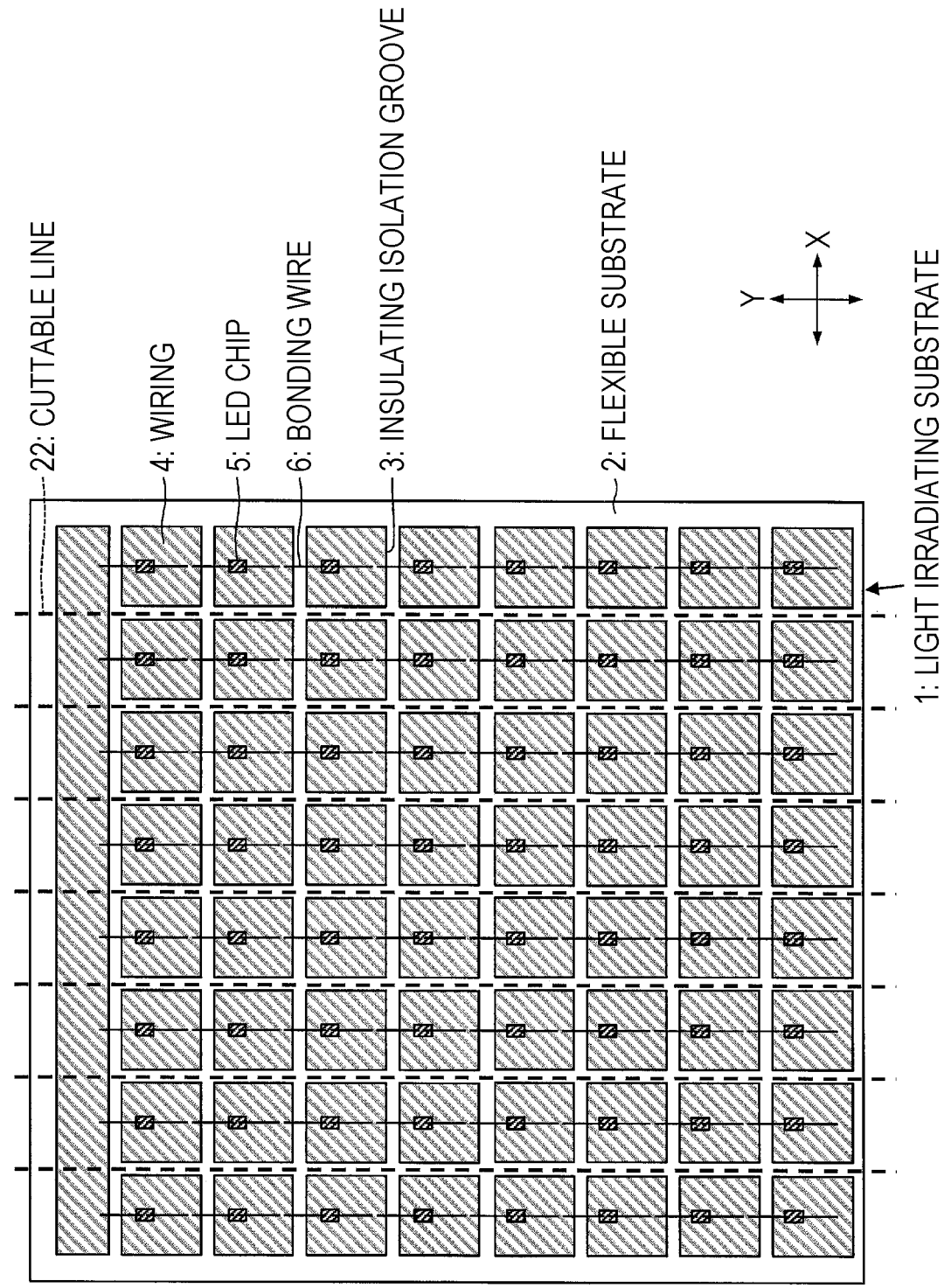
FIG. 37 is a schematic front surface view for explaining a light irradiating substrate according to Embodiment 8 of the invention.

Embodiment 8 will be described as follows with reference to FIGS. 37 and 38. Note that, the same reference signs will be assigned to constituents having the same functions as those of the constituents described in the aforementioned embodiments, and description thereof will be omitted.

The configuration of the light irradiating substrate 1 and the thickness of the spacer 21 are the same as those of Embodiment 1.

Figure 21:
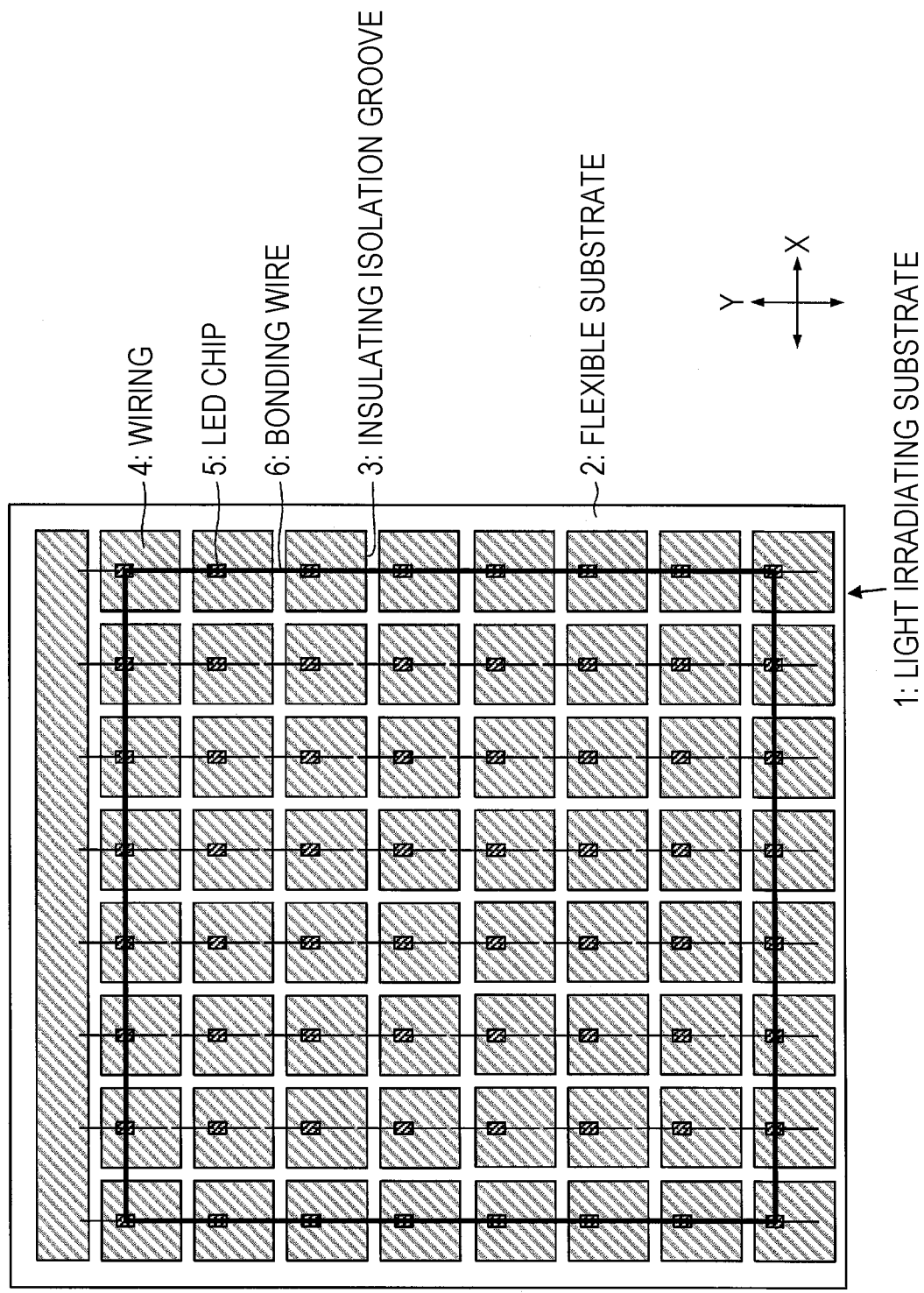
FIG. 21 is a schematic view for explaining definition of uniformity according to Embodiment 1 of the invention.

FIG. 21 is a schematic sectional view illustrating an example in which the light irradiating substrate 1 according to the present embodiment is applied as a phototherapy machine.

Meanwhile, the affected part 20 has various sizes. In a case where a size of the affected part 20 is apparently smaller than that of the light irradiating substrate 1 that has been already produced and there is an intention not to irradiate a part other than the affected part 20 with light, the light irradiating substrate 1 is able to be cut along a cuttable line 22 as illustrated in FIGS. 37 and 38. This is enabled for the first time when the light irradiating substrate 1 is able to be easily cut with scissors, in other words, is constituted by the flexible substrate 2, the wirings 4, the rear wirings 8, the LED protection resin 7, the spacer 21, and the like. In a case where the size of the affected part 20 is apparently larger than that of the light irradiating substrate 1 that has been already produced, the aforementioned intention is met by cutting the light irradiating substrate 1 and combining another light irradiating substrate 1 that is not cut with the light irradiating substrate 1 that is cut on the basis of similar technical ideas.

Figure 38:
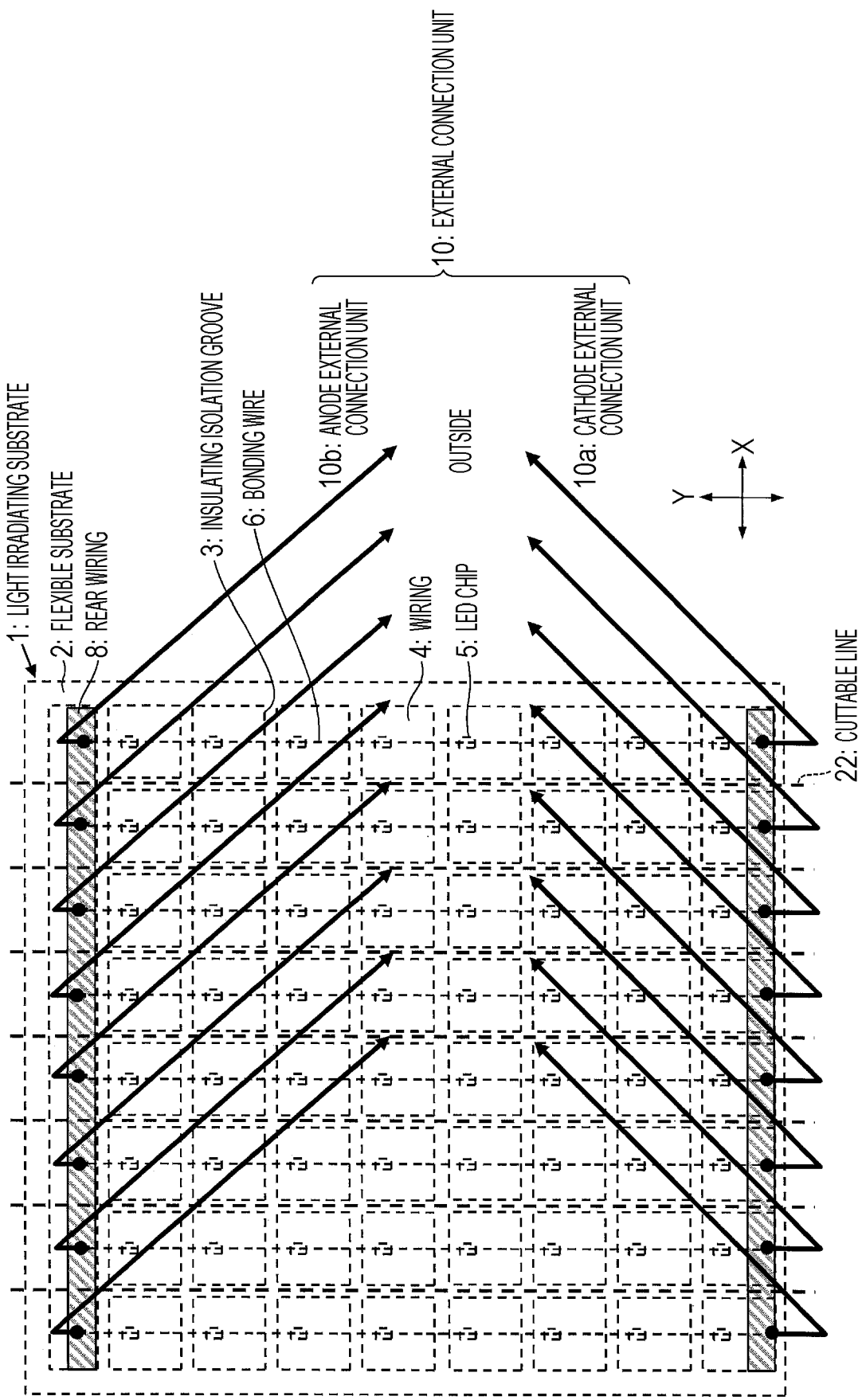
FIG. 38 is a schematic rear surface view for explaining the light irradiating substrate according to Embodiment 8 of the invention.

As illustrated in FIG. 38, in a case of the light irradiating substrate 1 to which the external connection unit 10 is attached in advance, the external connection unit 10 needs to be attached to appropriate rear wirings 8. A remarkable effect is achieved also when a plurality of external connection units 10 are attached in advance.

As above, the light irradiating substrate 1 according to the present embodiment is able to realize light irradiation that is suitable for treatment for a relatively small diseased part, does not force a patient to take an unnatural posture like in an irradiating device of a lamp type, and is performed almost uniformly and efficiently even for an affected part that is not flat. The same is applied to a phototherapy machine including the light irradiating substrate 1.

(Effect)

In the present embodiment, $U_1=0.8$ and $U_2=0.73$ were obtained in the same manner as Embodiment 7.

Embodiment 9

Another embodiment of the invention will be described as follows with reference to FIGS. 2 and 3, and FIGS. 39 to 42. In the present embodiment, a difference from Embodiment 1 will be mainly described, the same reference signs will be assigned to constituents having the same functions as those of the constituents described in Embodiment 1, and description thereof will be omitted.

Figure 39:
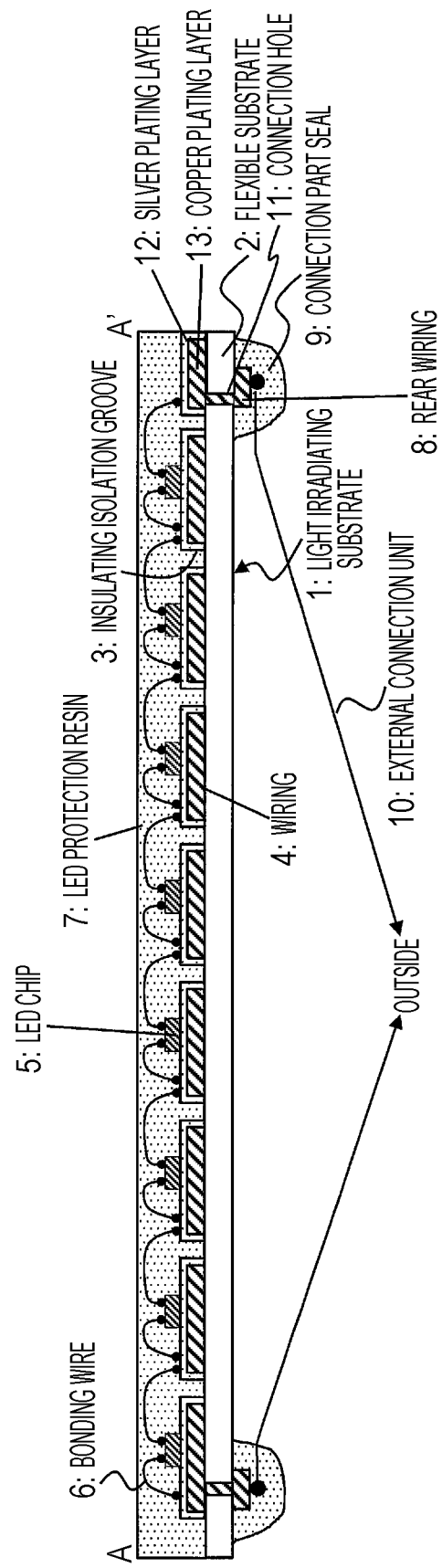
FIG. 39 is a schematic rear surface view for explaining a light irradiating substrate according to Embodiment 9 of the invention.

FIG. 39 is a schematic sectional view illustrating a configuration of the light irradiating substrate 1 according to the present embodiment. FIG. 2 is the schematic front surface view illustrating the configuration of the light irradiating substrate 1 according to the present embodiment. FIG. 3 is the schematic rear surface view illustrating the configuration of the light irradiating substrate 1 according to the present embodiment. Note that, FIG. 39 corresponds to the sectional view taken along the line A-A' of the light irradiating substrate 1, which is illustrated in FIG. 2.
(Schematic Configuration of Light Irradiating Substrate 1)

As illustrated in FIGS. 2, 3, and 39, the light irradiating substrate 1 includes the flexible substrate 2, the plurality of wirings 4 which are insulated and isolated from each other by the insulating isolation groove 3, the plurality of LED chips (LED elements) 5, the plurality of bonding wires 6, the LED protection resin 7, the external connection unit 10, the rear wirings 8, the connection holes 11, and the connection part seal 9.

A difference from Embodiment 1 lies in that the wavelength conversion member 15 is not included as illustrated in FIG. 39.

Figure 40:
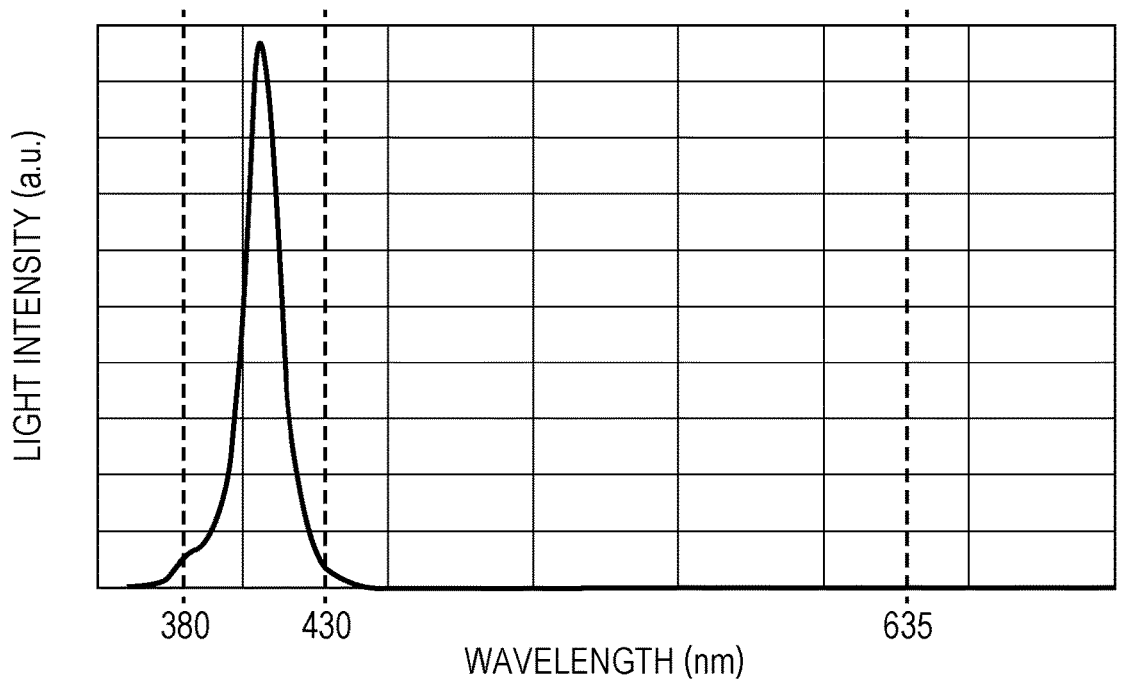
FIG. 40 is a graph illustrating an example of an emission spectrum of the light irradiating substrate according to Embodiment 9 of the invention.

An example of an emission spectrum of the light irradiating substrate 1 according to the present embodiment is illustrated in FIG. 40. Here, a case where only the first LED chips 5a are mounted as the LED chips 5 is illustrated. As illustrated in FIG. 40, it is found that output light includes only the first wavelength region light.

Figure 41:
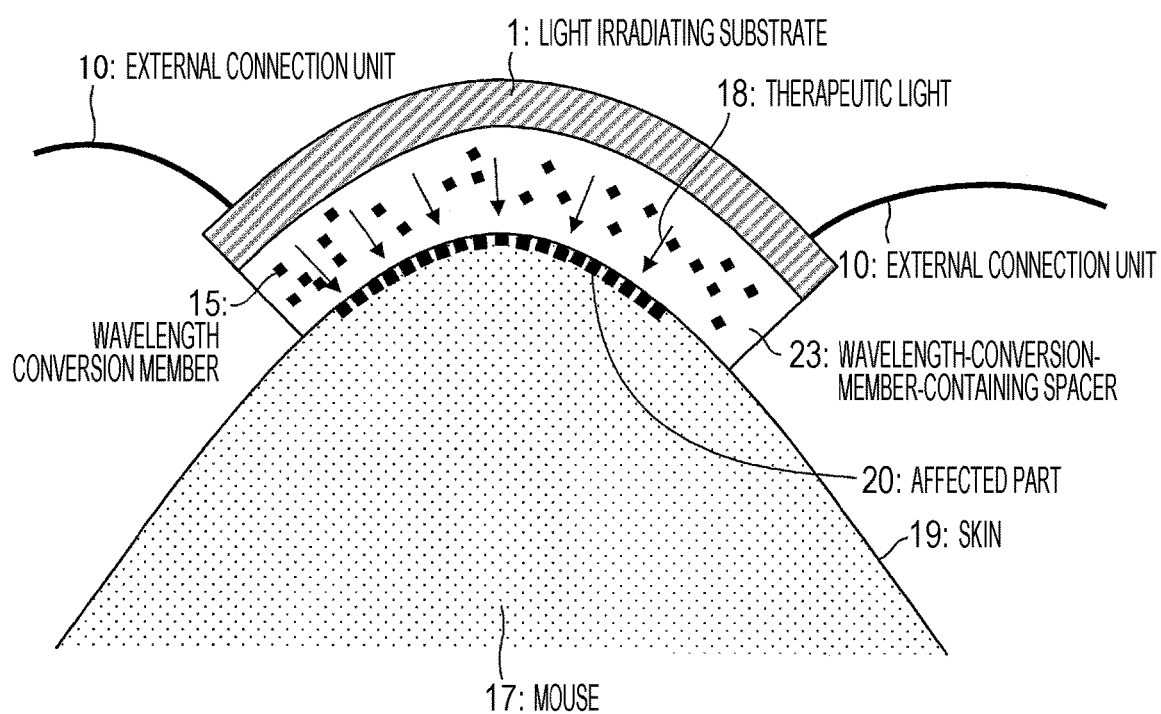
FIG. 41 is a schematic sectional view illustrating a form of the light irradiating substrate as a phototherapy machine, according to Embodiment 9 of the invention.

FIG. 41 is a schematic view illustrating an example in which the light irradiating substrate 1 according to the present embodiment is applied to treatment.

A difference from FIG. 20 of Embodiment 1 lies in that a wavelength-conversion-member-containing spacer 23 that contains the wavelength conversion member 15 is provided as illustrated in FIG. 41 instead of the spacer 21 that does not contain the wavelength conversion member 15. In this manner, the wavelength-conversion-member-containing spacer 23 includes the wavelength conversion member 15.
(Wavelength-Conversion-Member-Containing Spacer 23)

The wavelength-conversion-member-containing spacer 23 was produced by mixing the wavelength conversion member 15 with the spacer 21 illustrated in Embodiment 1. In the present embodiment, for example, one obtained by mixing and stirring silicone transparent resin and a phosphor of $(Ba,Sr)Si_2O_4$:Eu in advance and curing and molding the resultant was used. Note that, the thickness was set to be the same as that of Embodiment 1. Here, the silicone transparent resin was used as a material of the wavelength-conversion-member-containing spacer 23. However, there is no limitation thereto, and various forms such as one obtained by filling a plastic bag, which is processed so as to keep a constant thickness, with water or air, an epoxy or polyurethane resin plate which is transparent and flexible, and a water-absorbing polymer processed in a plate shape are able to be used as the spacer 21.

Note that, it is naturally possible to use any of the phosphors indicated in Embodiment 1 as the wavelength conversion member 15 contained in the wavelength-conversion-member-containing spacer 23. In this case, as indicated in Embodiment 1, it is also possible to change the wavelength of output light by changing a type of the LED chips 5 to be mounted on the light irradiating substrate 1.
(Emission Spectrum)

Figure 42:
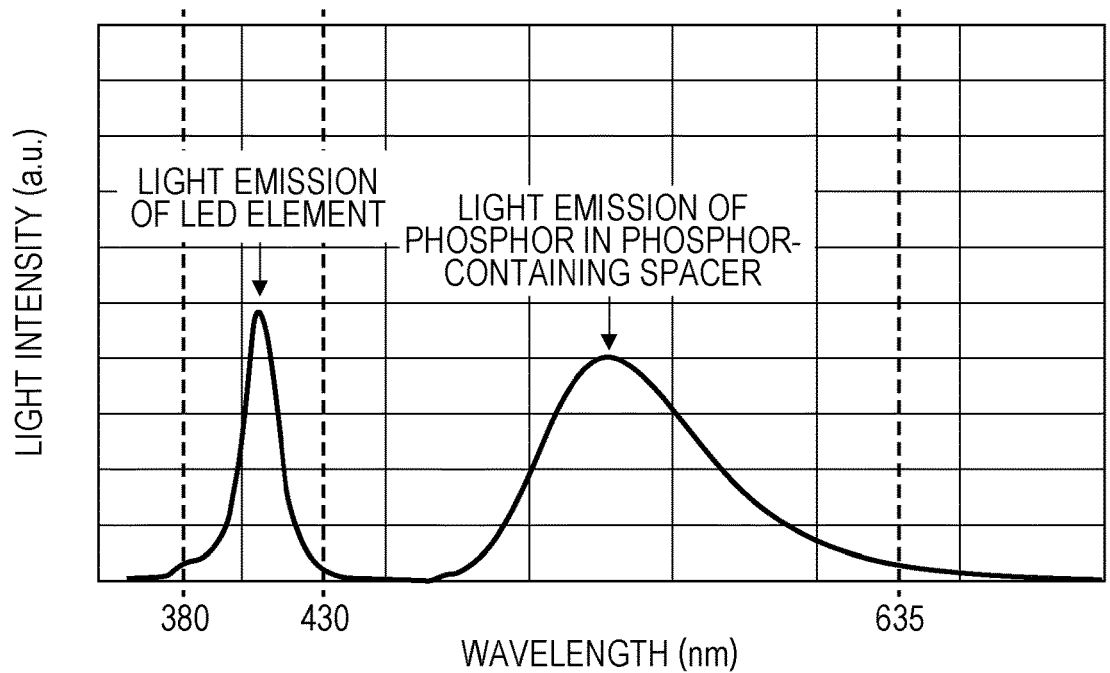
FIG. 42 is a graph illustrating an example of the emission spectrum when a wavelength-conversion-member-containing spacer is attached to the light irradiating substrate according to Embodiment 9 of the invention.

FIG. 42 illustrates an example of an emission spectrum when the wavelength-conversion-member-containing spacer 23 is attached to the light irradiating substrate 1 according to the present embodiment.

As illustrated in FIG. 42, it is found that output light includes first wavelength region light emitted from the LED chips 5 and second wavelength region light which is excited by the first wavelength region light and emitted by the phosphor of $(Ba,Sr)Si_2O_4$:Eu in the wavelength-conversion-member-containing spacer 23.

Note that, it is possible to freely change a ratio of the first wavelength region light and the second wavelength region light by changing a weight ratio of the phosphor of $(Ba,Sr)Si_2O_4$:Eu to the silicone transparent resin in the wavelength-conversion-member-containing spacer 23.

It is also possible to prepare in advance a wavelength-conversion-member-containing spacer 23 in which the weight ratio of the phosphor of $(Ba,Sr)Si_2O_4$:Eu to the silicone transparent resin to be mixed is changed. As a result, it is possible to freely change the ratio of the first wavelength region light and the second wavelength region light by using a desired wavelength-conversion-member-containing spacer 23 in combination.

For example, the light irradiating substrate 1 on which only first LED chips are mounted is prepared. Thereby, by preparing the wavelength-conversion-member-containing spacer 23 in which the weight ratio of the phosphor of $(Ba,Sr)Si_2O_4$:Eu to the silicone transparent resin is changed, it is possible to freely change the ratio of the first wavelength region light and the second wavelength region light in the same manner and light with various wavelengths is able to be emitted.

In other words, the wavelength-conversion-member-containing spacer 23 is able to be individually transferred as another product. This is advantageous also in terms of yield in mass production and ease of an operation.

In a place where photodynamic therapy is provided, the spectrum of the second wavelength region light is able to be appropriately selected in accordance with skin disease of a patient to provide customized treatment.
(Effect)

In the present embodiment, $U_1=0.85$ and $U_2=0.82$ were obtained.

Embodiment 10

Another embodiment of the invention will be described as follows with reference to FIG. 43. In the present embodiment, a difference from Embodiment 9 will be mainly described, the same reference signs will be assigned to constituents having the same functions as those of the constituents described in Embodiment 9, and description thereof will be omitted.

The configuration of the light irradiating substrate 1 according to the present embodiment is similar to that of Embodiment 9.

Figure 43:
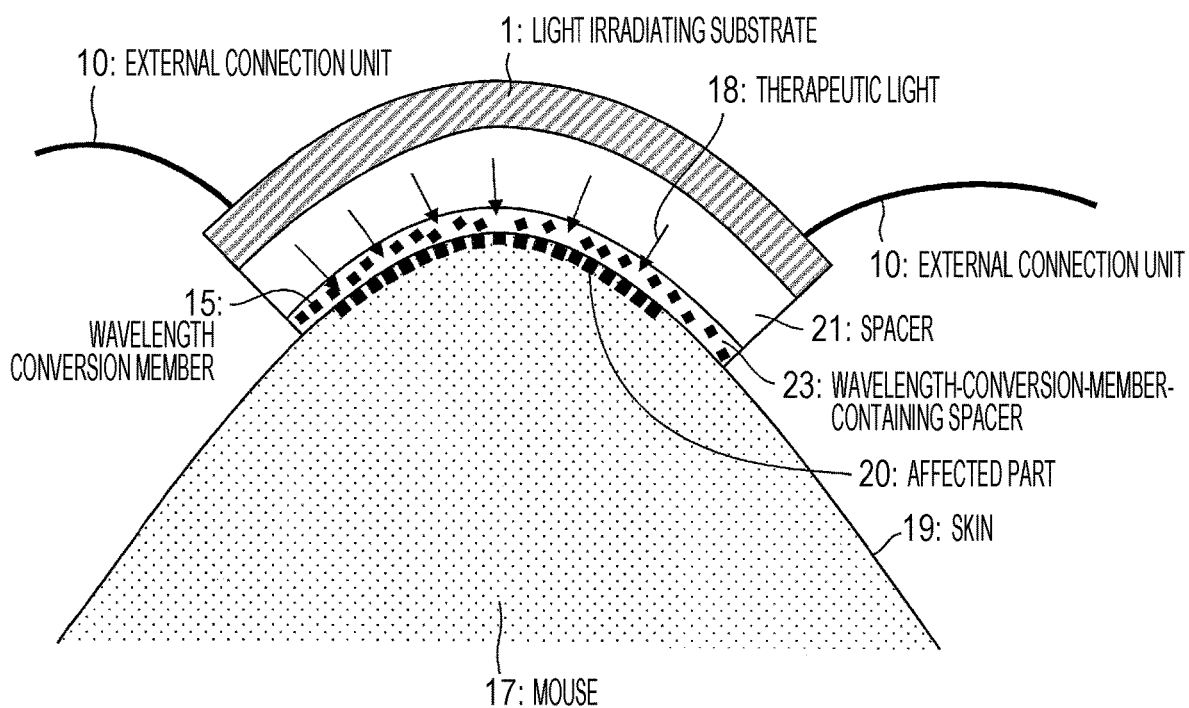
FIG. 43 is a schematic sectional view illustrating a form of a light irradiating substrate as a phototherapy machine, according to Embodiment 10 of the invention.

FIG. 43 is a schematic sectional view illustrating an example in which the light irradiating substrate 1 according to the present embodiment is applied to treatment.

A difference from Embodiment 9 lies in that both of the spacer 21 which does not contain the wavelength conversion member 15 and the wavelength-conversion-member-containing spacer 23 which contains the wavelength conversion member 15 are provided as illustrated in FIG. 43. The wavelength-conversion-member-containing spacer 23 whose configuration is the same as that of Embodiment 9 is used and a sum of the thickness of the spacer 21 and the thickness of the wavelength-conversion-member-containing spacer 23 is set to be the same as the thickness of the wavelength-conversion-member-containing spacer 23 of Embodiment 9.

(Emission Spectrum)

FIG. 42 is a graph illustrating an example of the emission spectrum when both of the spacer 21 and the wavelength-conversion-member-containing spacer 23 are attached to the light irradiating substrate 1 according to the present embodiment.

It is found that, when both of the spacer 21 and the wavelength-conversion-member-containing spacer 23 are provided, similarly to FIG. 42 indicated in Embodiment 9 described above, output light includes the first wavelength region light emitted from the LED chips 5 and the second wavelength region light which is excited by the first wavelength region light and emitted by the phosphor of $(Ba,Sr)Si_2O_4:Eu$ in the wavelength-conversion-member-containing spacer 23.

Note that, it is possible to freely change the ratio of the first wavelength region light and the second wavelength region light by changing the weight ratio of the phosphor of $(Ba,Sr)Si_2O_4:Eu$ to the silicone transparent resin in the wavelength-conversion-member-containing spacer 23.

Moreover, by preparing in advance a wavelength-conversion-member-containing spacer 23 in which the weight ratio of the phosphor of $(Ba,Sr)Si_2O_4:Eu$ to the silicone transparent resin to be mixed is changed, it is possible to freely change the ratio of the first wavelength region light and the second wavelength region light by using a desired wavelength-conversion-member-containing spacer 23 in combination.

For example, the light irradiating substrate 1 on which only first LED chips are mounted is prepared. Thereby, when the wavelength-conversion-member-containing spacer 23 in which the weight ratio of the phosphor of $(Ba,Sr)Si_2O_4:Eu$ to the silicone transparent resin is changed is prepared, it is possible to freely change the ratio of the first wavelength region light and the second wavelength region light in the same manner and light with various wavelengths is able to be emitted.

In other words, the wavelength-conversion-member-containing spacer 23 is able to be individually transferred as another product. This is advantageous also in terms of yield in mass production and ease of an operation.

In a place where photodynamic therapy is provided, the spectrum of the second wavelength region light is able to be appropriately selected in accordance with skin disease of a patient to provide customized treatment.

Note that, though the spacer 21 is arranged on the light irradiating substrate 1 and the wavelength-conversion-member-containing spacer 23 is arranged thereon in FIG. 43, the wavelength-conversion-member-containing spacer 23 may be arranged on the light irradiating substrate 1 and the spacer 21 may be arranged thereon in accordance with similar ideas. In this case, by considering that the spacer 21 directly contacts a skin, a material having so-called biocompatibility may be used.

Embodiment 11

Another embodiment of the invention will be described as follows with reference to FIG. 44. In the present embodiment, a difference from Embodiment 10 will be mainly described, the same reference signs will be assigned to constituents having the same functions as those of the constituents described in Embodiment 10, and description thereof will be omitted.

The configuration of the light irradiating substrate 1 according to the present embodiment is similar to that of Embodiment 10.

Figure 44:
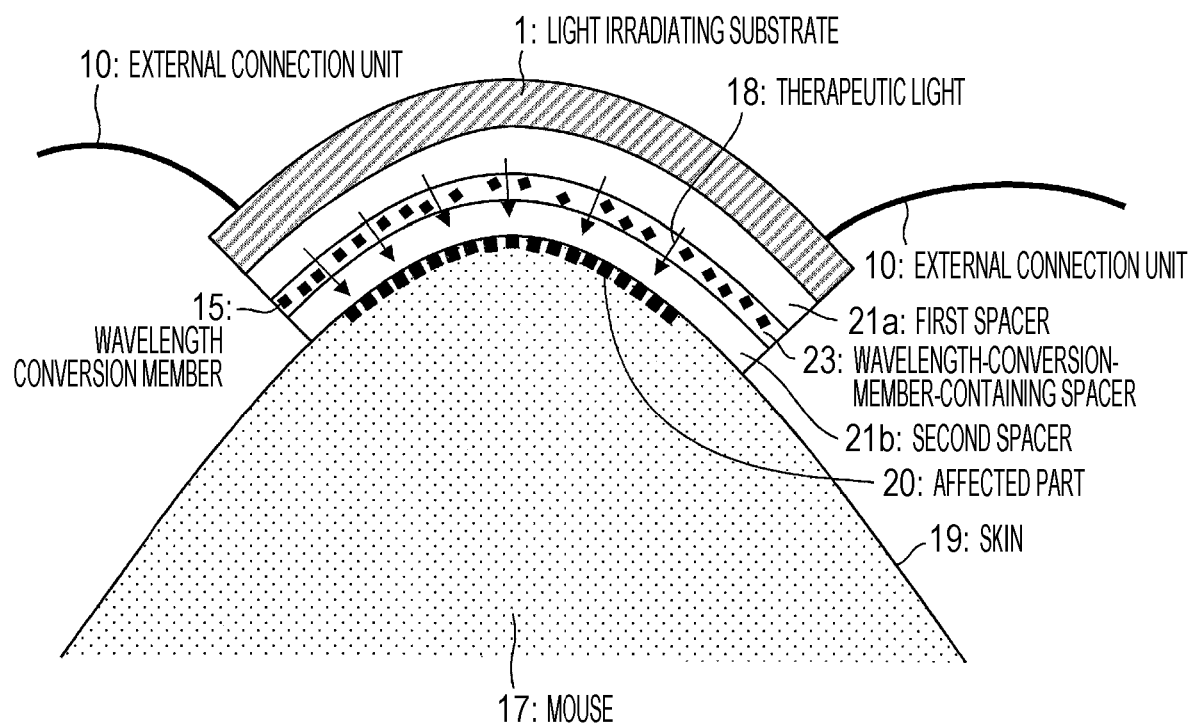
FIG. 44 is a schematic sectional view illustrating a form of a light irradiating substrate as a phototherapy machine, according to Embodiment 11 of the invention.

FIG. 44 is a schematic sectional view illustrating an example in which the light irradiating substrate 1 according to the present embodiment is applied to treatment.

A difference from Embodiment 10 lies in that the light irradiating substrate 1 includes a first spacer 21a, the wavelength-conversion-member-containing spacer 23, and a second spacer 21b as illustrated in FIG. 44. The wavelength-conversion-member-containing spacer 23 whose configuration is the same as that of Embodiment 10 is used and a sum of thicknesses of the first spacer 21a, the wavelength-conversion-member-containing spacer 23, and the second spacer 21b is set to be the same as a sum of the thickness of the spacer 21 and the thickness of wavelength-conversion-member-containing spacer 23 in Embodiment 10.

(Emission Spectrum)

FIG. 42 is a graph illustrating an example of the emission spectrum when the first spacer 21a, the wavelength-conversion-member-containing spacer 23, and the second spacer 21b are attached to the light irradiating substrate 1 according to the present embodiment.

It is found that, when the first spacer 21a, the wavelength-conversion-member-containing spacer 23, and the second spacer 21b are provided, similarly to FIG. 42 indicated in Embodiment 10 described above, output light includes the first wavelength region light emitted from the LED chips 5 and the second wavelength region light which is excited by the first wavelength region light and emitted by the phosphor of $(Ba,Sr)Si_2O_4:Eu$ in the wavelength-conversion-member-containing spacer 23.

Note that, it is possible to freely change the ratio of the first wavelength region light and the second wavelength region light by changing the weight ratio of the phosphor of $(Ba,Sr)Si_2O_4:Eu$ to the silicone transparent resin in the wavelength-conversion-member-containing spacer 23.

Moreover, by preparing in advance a wavelength-conversion-member-containing spacer 23 in which the weight ratio of the phosphor of $(Ba,Sr)Si_2O_4:Eu$ to the silicone transparent resin to be mixed is changed, it is possible to freely change the ratio of the first wavelength region light and the second wavelength region light by using a desired wavelength-conversion-member-containing spacer 23 in combination.

For example, the light irradiating substrate 1 on which only first LED chips are mounted is prepared. Thereby, when the wavelength-conversion-member-containing spacer 23 in which the weight ratio of the phosphor of $(Ba,Sr)Si_2O_4:Eu$ to the silicone transparent resin is changed is prepared, it is possible to freely change the ratio of the first wavelength region light and the second wavelength region light in the same manner and light with various wavelengths is able to be emitted.

In a place where photodynamic therapy is provided, the spectrum of the second wavelength region light is able to be appropriately selected in accordance with skin disease of a patient to provide customized treatment.

Further, when at least either the wavelength-conversion-member-containing spacer 23 or the second spacer 21b has an adhesive property, it is possible to prepare in advance a wavelength-conversion-member-containing spacer 23 to which the second spacer 21b is attached.

That is, the wavelength-conversion-member-containing spacer 23 to which the second spacer 21b is attached is able to be individually transferred as another product. This is advantageous also in terms of yield in mass production and ease of an operation.

Here, when intensity of adhesiveness between the first spacer 21a and the wavelength-conversion-member-containing spacer 23 to which the second spacer 21b is attached is reduced, the wavelength-conversion-member-containing spacer 23 to which the second spacer 21b is attached is able to be replaced more easily and appropriately compared to Embodiment 10 in a place where photodynamic therapy is provided. This makes it possible to customize the first wavelength region light and the second wavelength region light more easily.

Additionally, it is also possible to further add a spacer 21 or add a wavelength-conversion-member-containing spacer 23.

(Effect)

In the present embodiment, $U_1=0.83$ and $U_2=0.81$ were obtained.

The embodiments and exemplary embodiments disclosed herein are to be construed as illustrative and not limitative in all respects. The scope of the invention is indicated by the claims rather than the foregoing description, and is intended to encompass meanings equivalent to the claims and all modifications falling in the scope of the claims.

[Conclusion]

A light irradiating device according to an aspect 1 of the invention includes a group of LED light sources that has at least one LED light source two-dimensionally arranged on a flexible substrate, in which light output by the group of LED light sources includes first wavelength region light whose light-emission intensity peak is in a wavelength range of 380 nm or more and 430 nm or less, and second wavelength region light whose light-emission intensity peak is in a wavelength range of more than 430 nm and 635 nm or less, and the group of LED light sources has uniform in-plane intensity of light irradiation.

According to the aforementioned configuration, it is possible to provide the light irradiating device capable of realizing light irradiation that is suitable for treatment for a relatively small diseased part and is performed almost uniformly and efficiently even for an affected part that is not flat. According to the aforementioned configuration, it is possible to realize efficient and uniform light irradiation while suppressing a side effect due to the light irradiation to a minimum, so that a phototherapeutic effect with a burden of a patient and his/her family suppressed is able to be achieved. According to the aforementioned configuration, it is possible to provide a phototherapy machine that is able to be cut in accordance with a size of an affected part.

In the light irradiating device according to an aspect 2 of the invention, it is preferable that the at least one LED light source includes an LED element (LED chip 5) that outputs the first wavelength region light, and a wavelength conversion member that absorbs the first wavelength region light output from the LED element and outputs the second wavelength region light, in the aspect 1.

According to the aforementioned configuration, the light irradiating device is able to output both of the first wavelength region light and the second wavelength region light.

In the light irradiating device according to an aspect 3 of the invention, it is preferable that the wavelength conversion member is a phosphor and the phosphor is constituted by at least one material represented by general formulas of $BaSi_2(O,Cl)_2N_2:Eu$, $(Ba,Sr)MgAl_{10}O_{17}:Eu$, $Mn$, $(Ba,Sr)Si_2O_4:Eu$, $Sr_4Al_{14}O_{25}:Eu$, $SrAl_2O_4:Eu$, $(Sr,Al)_6(O,N)_8:Eu$, $(Lu,Y,Gd)_3(Al,Ga)_5O_{12}:Ce$, $La_3Si_6N_{11}:Ce$, $(Sr, Ca)AlSiN_3:Eu$, and $K_2SiF_6:Mn$, in the aspect 2.

According to the aforementioned configuration, it is possible to realize the wavelength conversion member by using the phosphor.

In the light irradiating device according to an aspect 4 of the invention, it is preferable that the group of LED light sources includes a first LED element (first LED chip 5a) that is one of the LED light sources and outputs the first wavelength region light, and a second LED element (second LED chip 5b) that is one of the LED light sources and is different from the first LED element, and outputs the second wavelength region light, in the aspect 1.

According to the aforementioned configuration, the light irradiating device is able to output both of the first wavelength region light and the second wavelength region light.

In the light irradiating device according to an aspect 5 of the invention, it is preferable that the group of LED light sources includes a plurality of first LED elements and a plurality of second LED elements, one of the second LED elements is arranged between two of the first LED elements and one of the first LED elements is arranged between two of the second LED elements in both a first direction and a second direction perpendicular to the first direction, in the aspect 4.

According to the aforementioned configuration, the first LED elements and the second LED elements are able to be alternately arranged, thus making it possible to realize more uniform light irradiation.

In the light irradiating device according to an aspect 6 of the invention, it is preferable that the first LED elements and the second LED elements are arranged on the same wiring pattern and constitute the LED light sources, in the aspect 5.

According to the aforementioned configuration, it is possible to output both of the first wavelength region light and the second wavelength region light.

In the light irradiating device according to an aspect 7 of the invention, it is preferable that center of gravity of each of the second LED elements matches a center position of each of the first LED elements, in the aspect 6.

According to the aforementioned configuration, the first LED element and the second LED element are able to be set as one unit and more uniform light irradiation is able to be realized.

In the light irradiating device according to an aspect 8 of the invention, it is preferable that the group of LED light sources includes at least two second LED elements, one first LED element and the two second LED elements are in rectangular shapes in top view, the one first LED element is arranged between the two second LED elements, and the one first LED element and the two second LED elements are arranged so that each side of the rectangular shape of each of the two second LED elements and each side of the rectangular shape of the one first LED element do not face each other, in the aspect 4.

According to the aforementioned configuration, absorption of light, which is emitted from the first LED elements, by the second LED elements is minimized, thus making it possible to further increase the first wavelength region light.

In the light irradiating device according to an aspect 9 of the invention, it is possible that at least one layer of a spacer is provided on a light-output-side surface of the flexible substrate in which the LED element is two-dimensionally arranged, the wavelength conversion member is a phosphor, and, of the at least one layer of the spacer, the phosphor is contained in at least one layer of a spacer, in the aspect 2.

According to the aforementioned configuration, by preparing one flexible substrate in which an LED element is two-dimensionally arranged, the spacer that contains the phosphor as the wavelength conversion member is able to be replaced.

As a result, in a case where it is intended to change a wavelength region of the second wavelength region light, by preparing spacers containing different types of phosphors, it is possible to easily obtain output light with a desired wavelength range by easily combining a flexible substrate in which an LED element is two-dimensionally arranged and a spacer that contains a phosphor.

In the light irradiating device according to an aspect 10 of the invention, it is preferable that the spacer is attachable to and detachable from the flexible substrate in which the LED element is two-dimensionally arranged, in the aspect 9.

According to the aforementioned configuration, for example, by preparing a plurality of types of spacers containing different types of phosphors, when a user attaches or detaches a spacer to or from the flexible substrate, output light with a desired wavelength region is able to be easily obtained.

A phototherapy machine according to an aspect 11 of the invention includes the light irradiating device according to any of the aspects 1 to 10.

According to the aforementioned configuration, it is possible to realize the phototherapy machine exerting a similar effect to that of each of the light irradiating devices described above.

The invention is not limited to each of the embodiments described above, and may be modified in various manners within the scope indicated in the claims and an embodiment achieved by appropriately combining technical means disclosed in each of different embodiments is also encompassed in the technical scope of the invention.

Further, by combining the technical means disclosed in each of the embodiments, a new technical feature may be formed.

REFERENCE SIGNS LIST 1 light irradiating substrate (light irradiating device)
2 flexible substrate
3 insulating isolation groove
4 wiring
5 LED chip (LED element)
5a first LED chip (first LED element)
5b second LED chip (second LED element)
6 bonding wire
7 LED protection resin
8 rear wiring
8a first-LED-chip rear wiring
8b second-LED-chip rear wiring
9 connection part seal
10 external connection unit
10a cathode external connection unit
10b anode external connection unit
10c first-LED-chip cathode external connection unit
10d first-LED-chip anode external connection unit
10e second-LED-chip cathode external connection unit
10f second-LED-chip anode external connection unit
11 connection hole
12 silver plating layer
13 copper plating layer
14 first electrical conducting material pattern
15 wavelength conversion member
16 LED protection resin dome
17 mouse
18 therapeutic light
19 skin
20 affected part
21 spacer
21a first spacer
21b second spacer
22 cuttable line
23 wavelength-conversion-member-containing spacer

The invention claimed is:

1. A light irradiating device comprising
a group of LED light sources that has at least one LED light source two-dimensionally arranged on a flexible substrate, wherein
light output by the group of LED light sources includes
first wavelength region light whose light-emission intensity peak is in a wavelength range of 380 nm or more and 430 nm or less, and
second wavelength region light whose light-emission intensity peak is in a wavelength range of more than 430 nm and 635 nm or less,
the at least one LED light source includes
a first LED element that outputs the first wavelength region light, and
a wavelength conversion member that absorbs the first wavelength region light output from the first LED element and outputs the second wavelength region light,
at least one layer of a spacer is provided on a light-output-side surface of the flexible substrate in which the first LED element is two-dimensionally arranged,
of the at least one layer of the spacer, at least one layer of a spacer is a spacer that contains the wavelength conversion member, and
a total value of thicknesses of constituents provided from the first LED element to an affected part is 0.5 times or more an average value of pitches between first LED elements.

2. The light irradiating device according to claim 1, wherein a total value of thicknesses of constituents provided from the first LED element to an affected part is 0.8 times or more an average value of pitches between first LED elements.

3. The light irradiating device according to claim 1, wherein the wavelength conversion member is a phosphor.

4. The light irradiating device according to claim 1, wherein the first LED element is covered with resin having transparency with respect to the first wavelength region light, and the spacer is attachable to and detachable from the resin.

5. The light irradiating device according to claim 1, wherein treatment is able to be performed by appropriately selecting a spectrum of the second wavelength region light according to skin disease of a patient.

6. The light irradiating device according to claim 1, wherein a ratio of the first wavelength region light and the second wavelength region light is able to be changed by using a spacer that contains the wavelength conversion member in combination.

7. A phototherapy machine comprising the light irradiating device according to claim 1.

8. A light irradiating device comprising
a group of LED light sources that has at least one LED light source two-dimensionally arranged on a flexible substrate, wherein
light output by the group of LED light sources includes
first wavelength region light whose light-emission intensity peak is in a wavelength range of 380 nm or more and 430 nm or less, and second wavelength region light whose light-emission intensity peak is in a wavelength range of more than 430 nm and 635 nm or less, the group of LED light sources includes
- a first LED element that is one of the LED light sources and outputs the first wavelength region light, and
- a second LED element that is one of the LED light sources and is different from the first LED element, and outputs the second wavelength region light, at least one layer of a spacer is provided on a light-output-side surface of the group of LED light sources, the group of LED light sources includes at least two second LED elements, one first LED element and the two second LED elements are in rectangular shapes in top view, the one first LED element is arranged between the two second LED elements, the one first LED element and the two second LED elements are arranged so that each side of the rectangular shape of each of the two second LED elements and each side of the rectangular shape of the one first LED element do not face each other, and a total value of thicknesses of constituents provided from the first LED element and the second LED element to an affected part is 0.5 times or more an average value of pitches between the LED light sources.

9. The light irradiating device according to claim 8, wherein a total value of thicknesses of constituents provided from the first LED element and the second LED element to an affected part is 0.8 times or more an average value of pitches between the LED light sources.

10. The light irradiating device according to claim 8, wherein a total value of thicknesses of constituents provided from the first LED element and the second LED element to an affected part is two times or less an average value of pitches between the LED light sources.

11. The light irradiating device according to claim 8, wherein a peak wavelength of the second LED element is 470 nm or more.

12. The light irradiating device according to claim 8, wherein center of gravity of each of the two second LED elements matches a position of the one first LED element.

13. The light irradiating device according to claim 8, wherein the first LED element and the second LED element are covered with resin having transparency with respect to the first wavelength region light and the second wavelength region light, and the spacer is attachable to and detachable from the resin.

14. A phototherapy machine comprising the light irradiating device according to claim 8.

15. A light irradiating device comprising
a group of LED light sources that has at least one LED light source two-dimensionally arranged on a flexible substrate, wherein light output by the group of LED light sources includes
- first wavelength region light whose light-emission intensity peak is in a wavelength range of 380 nm or more and 430 nm or less, and
- second wavelength region light whose light-emission intensity peak is in a wavelength range of more than 430 nm and 635 nm or less, the at least one LED light source includes
- a first LED element that outputs the first wavelength region light, and
- a wavelength conversion member that absorbs the first wavelength region light output from the first LED element and outputs the second wavelength region light, at least one layer of a spacer is provided on a light-output-side surface of the flexible substrate in which the first LED element is two-dimensionally arranged, and a total value of thicknesses of constituents provided from the first LED element to an affected part is two times or less an average value of pitches between first LED elements.

* * * * *